US008398668B2

(12) United States Patent
Makower et al.

(10) Patent No.: US 8,398,668 B2
(45) **Date of Patent: *Mar. 19, 2013**

(54) DEVICES AND METHODS FOR TREATMENT OF OBESITY

(75) Inventors: Joshua Makower, Los Altos, CA (US); Theodore M. Bender, Oakland, CA (US); Brian K. Shiu, Sunnyvale, CA (US); Pablo G. Acosta, Newark, CA (US); Shuji Uemura, San Francisco, CA (US); Josef L. Friedmann, Boulder Creek, CA (US); Crystine Lee, Vallejo, CA (US)

(73) Assignee: Vibrynt, Inc., Redwood City, CA (US)

( * ) Notice: Subject to any disclaimer, the term of this patent is extended or adjusted under 35 U.S.C. 154(b) by 1277 days.

This patent is subject to a terminal disclaimer.

(21) Appl. No.: 11/716,986

(22) Filed: Mar. 10, 2007

(65) Prior Publication Data

US 2007/0250103 A1 Oct. 25, 2007

Related U.S. Application Data

(63) Continuation-in-part of application No. 11/407,701, filed on Apr. 19, 2006, now Pat. No. 8,070,768.

(60) Provisional application No. 60/833,284, filed on Jul. 24, 2006, provisional application No. 60/877,595, filed on Dec. 28, 2006.

(51) Int. Cl.
*A61M 29/00* (2006.01)
*A61F 2/00* (2006.01)
*A61F 13/00* (2006.01)

(52) U.S. Cl. ........................... 606/192; 606/191; 600/37

(58) Field of Classification Search .................. 606/119, 606/151, 191, 192, 198, 200, 201, 202, 203; 600/37

See application file for complete search history.

(56) References Cited

U.S. PATENT DOCUMENTS

| | | | |
|---|---|---|---|
| 233,475 | A | 10/1880 | Cook et al. |
| 659,422 | A | 10/1900 | Shidler |
| 780,392 | A | 1/1905 | Wanamaker et al. |
| 789,467 | A | 5/1905 | West |
| 1,461,524 | A | 7/1923 | Goddard |
| 2,579,192 | A | 12/1951 | Kohl et al. |
| 2,646,298 | A | 7/1953 | Leary |
| 2,697,624 | A | 12/1954 | Thomas et al. |
| 2,734,299 | A | 2/1956 | Masson |

(Continued)

FOREIGN PATENT DOCUMENTS

| | | |
|---|---|---|
| EP | 1 016 377 A2 | 7/2000 |
| EP | 1 520 563 | 6/2005 |

(Continued)

OTHER PUBLICATIONS

About the Vertical Sleeve Gastrectomy. Mar. 24, 2006, pp. 1-1. http://obesityhelp.com/forums/VSG/about.html.

(Continued)

*Primary Examiner* — Gary Jackson
*Assistant Examiner* — Michael Mendoza
(74) *Attorney, Agent, or Firm* — Law Office of Alan W. Cannon

(57) ABSTRACT

Methods, devices, tools and assemblies for treating a patient to effect weight loss. One method embodiment involves passing a device including an expandable member in a collapsed configuration and a buoyancy member through an opening in the skin of a patient and into the abdominal cavity of the patient, and anchoring at least a portion of the expandable member, relative to at least one structure in the abdominal cavity. Devices including at least one expandable member and at least one buoyancy member are provided.

33 Claims, 36 Drawing Sheets

U.S. PATENT DOCUMENTS 2,825,592 A 3/1958 Semple
3,326,586 A 6/1967 Frost et al.
3,470,834 A 10/1969 Bone
3,521,918 A 7/1970 Hammond
3,571,864 A 3/1971 Oger
3,664,435 A 5/1972 Klessig
3,675,639 A 7/1972 Cimber
3,713,680 A 1/1973 Pagano
3,756,638 A 9/1973 Stockberger
3,873,140 A 3/1975 Bloch
3,931,667 A 1/1976 Merser et al.
3,976,079 A 8/1976 Samuels et al.
4,006,747 A 2/1977 Kronenthal et al.
4,060,089 A 11/1977 Noiles
4,133,315 A 1/1979 Berman et al.
4,210,148 A 7/1980 Stivala
4,246,893 A 1/1981 Berson
4,291,698 A 9/1981 Fuchs et al.
4,328,805 A 5/1982 Akopov et al.
4,416,267 A 11/1983 Garren et al.
4,458,681 A 7/1984 Hophins
4,472,226 A 9/1984 Redinger et al.
4,485,805 A 12/1984 Foster, Jr. et al.
4,493,323 A 1/1985 Albright et al.
4,558,699 A 12/1985 Bashour
4,592,339 A 6/1986 Kuzmak et al.
4,592,342 A 6/1986 Salmasian
4,621,640 A 11/1986 Mulhollan et al.
4,669,473 A 6/1987 Richards et al.
4,694,827 A 9/1987 Weiner et al.
4,696,288 A 9/1987 Kuzmak et al.
4,705,040 A 11/1987 Mueller et al.
4,714,281 A 12/1987 Peck
4,723,547 A 2/1988 Kullas et al.
4,738,255 A 4/1988 Goble et al.
4,739,758 A 4/1988 Lai et al.
4,744,364 A 5/1988 Kensey
4,750,492 A 6/1988 Jacobs
4,803,985 A 2/1989 Hill
4,823,794 A 4/1989 Pierce
4,899,747 A 2/1990 Garren et al.
4,955,913 A 9/1990 Robinson
5,002,550 A 3/1991 Li
5,033,481 A 7/1991 Heyler, III
5,041,129 A 8/1991 Hayhurst et al.
5,084,061 A 1/1992 Gau et al.
5,100,421 A 3/1992 Christoudias
5,112,310 A 5/1992 Grobe
5,123,914 A 6/1992 Cope
5,129,912 A 7/1992 Noda et al.
RE34,021 E 8/1992 Mueller et al.
5,151,086 A 9/1992 Duh et al.
5,188,104 A 2/1993 Wernicke et al.
5,217,470 A 6/1993 Weston
5,234,454 A 8/1993 Bangs
5,246,456 A 9/1993 Wilkinson
5,258,015 A 11/1993 Li et al.
5,259,399 A 11/1993 Brown
5,269,809 A 12/1993 Hayhurst et al.
5,292,344 A 3/1994 Douglas
5,334,200 A 8/1994 Johnson
5,354,271 A 10/1994 Voda
5,364,408 A 11/1994 Gordon
5,391,182 A 2/1995 Chin
5,405,352 A 4/1995 Weston
5,423,872 A 6/1995 Cigaina
5,428,123 A 6/1995 Ward et al.
5,433,723 A 7/1995 Lindenberg et al.
5,445,608 A 8/1995 Chen et al.
5,470,337 A 11/1995 Moss
5,472,446 A 12/1995 Torre
5,480,406 A 1/1996 Nolan et al.
5,496,311 A 3/1996 Abele et al.
5,507,754 A 4/1996 Green et al.
5,545,171 A 8/1996 Sharkey et al.
5,545,178 A 8/1996 Kensey et al.
5,549,621 A 8/1996 Bessler et al.
5,554,162 A 9/1996 DeLange
5,573,540 A 11/1996 Yoon
5,591,177 A 1/1997 Lehrer
5,601,604 A 2/1997 Vincent
5,626,614 A 5/1997 Hart
5,634,936 A 6/1997 Linden et al.
5,647,836 A 7/1997 Blake, III et al.
5,690,691 A 11/1997 Chen et al.
5,716,368 A 2/1998 Torre et al.
5,725,557 A 3/1998 Gattuma et al.
5,846,254 A 12/1998 Schulze et al.
5,888,196 A 3/1999 Bonutti
5,931,788 A 8/1999 Keen et al.
5,938,669 A 8/1999 Klaiber et al.
5,951,590 A 9/1999 Goldfarb
5,961,440 A 10/1999 Schweich, Jr. et al.
5,971,447 A 10/1999 Steck, III
5,993,473 A 11/1999 Chan et al.
6,013,053 A 1/2000 Bower et al.
6,067,991 A 5/2000 Forsell
6,080,160 A 6/2000 Chen et al.
6,097,984 A 8/2000 Douglas
6,102,922 A 8/2000 Jakobsson et al.
6,113,609 A 9/2000 Adams
6,143,006 A 11/2000 Chan
6,162,234 A 12/2000 Freedland et al.
6,186,149 B1 2/2001 Pacella et al.
6,270,530 B1 8/2001 Eldridge et al.
6,273,903 B1 * 8/2001 Wilk ............................ 606/219
6,420,452 B1 7/2002 Gunatillake et al.
6,437,073 B1 8/2002 Gunatillake et al.
6,447,533 B1 9/2002 Adams
6,454,785 B2 9/2002 De Hoyos Garza
6,475,136 B1 11/2002 Forsell
6,488,691 B1 12/2002 Carroll et al.
6,491,707 B2 12/2002 Makower et al.
6,494,888 B1 12/2002 Laufer et al.
6,500,148 B1 12/2002 Pinchuk et al.
6,506,196 B1 1/2003 Laufer
6,511,490 B2 1/2003 Robert et al.
6,535,764 B2 3/2003 Imran et al.
6,558,400 B2 5/2003 Deem et al.
6,656,182 B1 12/2003 Hayhurst
6,663,639 B1 12/2003 Laufer et al.
6,669,713 B2 12/2003 Adams
6,675,809 B2 1/2004 Stack et al.
6,736,793 B2 5/2004 Meyer et al.
6,746,460 B2 6/2004 Gannoe et al.
6,755,869 B2 6/2004 Geitz
6,773,441 B1 8/2004 Laufer et al.
6,790,213 B2 9/2004 Cherok et al.
6,821,285 B2 11/2004 Laufer et al.
6,835,200 B2 12/2004 Laufer et al.
6,869,395 B2 3/2005 Page et al.
6,900,055 B1 5/2005 Fuller
6,908,487 B2 6/2005 Cigaina
6,981,978 B2 1/2006 Gannoe
6,994,715 B2 2/2006 Gannoe et al.
7,033,373 B2 4/2006 de la Torre et al.
7,037,344 B2 5/2006 Kagan et al.
7,153,314 B2 12/2006 Laufer et al.
7,167,750 B2 1/2007 Knudson et al.
7,223,277 B2 5/2007 DeLegge
7,255,675 B2 8/2007 Gertner et al.
7,310,557 B2 12/2007 Maschino et al.
7,334,822 B1 2/2008 Hines, Jr.
7,338,433 B2 3/2008 Coe
7,354,454 B2 4/2008 Stack et al.
7,374,565 B2 5/2008 Hassler et al.
7,402,166 B2 7/2008 Feigl
7,416,554 B2 8/2008 Lam et al.
7,534,248 B2 5/2009 Mikkaichi et al.
7,618,426 B2 11/2009 Ewers et al.
7,666,195 B2 2/2010 Kelleher et al.
7,670,279 B2 3/2010 Gertner
7,775,967 B2 8/2010 Gertner
7,841,978 B2 11/2010 Gertner
7,988,617 B2 8/2011 Gertner
8,075,582 B2 * 12/2011 Lointier et al. ............... 606/192
2001/0010005 A1 7/2001 Kammerer et al.

2001/0011543 A1 8/2001 Forsell
2001/0044639 A1 11/2001 Levinson
2002/0055757 A1 5/2002 Torre et al.
2002/0128684 A1 9/2002 Foerster
2002/0161382 A1 10/2002 Neisz et al.
2002/0161414 A1 10/2002 Flesler et al.
2002/0188354 A1 12/2002 Peghini et al.
2003/0021822 A1 1/2003 Lloyd
2003/0055463 A1 3/2003 Gordon et al.
2003/0055465 A1 3/2003 Ben-Haim et al.
2003/0093117 A1 5/2003 Saadat Vahid
2003/0208212 A1 11/2003 Cigaina
2004/0006351 A1 1/2004 Gannoe et al.
2004/0024386 A1 2/2004 Deem et al.
2004/0030347 A1 2/2004 Gannoe
2004/0044353 A1 3/2004 Gannoe
2004/0044357 A1 3/2004 Gannoe
2004/0054352 A1 3/2004 Adams et al.
2004/0059289 A1 3/2004 Garza Alvarez
2004/0068224 A1 4/2004 Couvillon et al.
2004/0092892 A1 5/2004 Kagan et al.
2004/0097986 A1 5/2004 Adams
2004/0098060 A1 5/2004 Ternes
2004/0116949 A1 6/2004 Ewers et al.
2004/0122456 A1 6/2004 Saadat et al.
2004/0122473 A1 6/2004 Ewers et al.
2004/0148034 A1 7/2004 Kagan et al.
2004/0186503 A1 9/2004 Delegge
2004/0193194 A1 9/2004 Laufer et al.
2004/0194790 A1 10/2004 Laufer et al.
2004/0243178 A1 12/2004 Haut et al.
2004/0243179 A1 12/2004 Foerster
2004/0243180 A1 12/2004 Donnelly et al.
2004/0260345 A1 12/2004 Foerster
2004/0267378 A1 12/2004 Gazi et al.
2005/0022827 A1 2/2005 Woo et al.
2005/0049718 A1 3/2005 Dann et al.
2005/0096638 A1 5/2005 Starkebaum et al.
2005/0159769 A1 7/2005 Alverdy
2005/0197687 A1 9/2005 Molaei et al.
2005/0203344 A1 9/2005 Orban, III et al.
2005/0216040 A1 9/2005 Gertner et al.
2005/0216042 A1 9/2005 Gertner et al.
2005/0222638 A1 10/2005 Foley et al.
2005/0228415 A1 10/2005 Gertner
2005/0261712 A1 11/2005 Balbierz
2005/0267405 A1 12/2005 Shah
2005/0267406 A1 12/2005 Hassler, Jr.
2005/0267533 A1 12/2005 Gertner
2005/0267595 A1 12/2005 Chen et al.
2005/0267596 A1 12/2005 Chen et al.
2005/0277960 A1 12/2005 Hassler, Jr. et al.
2005/0277974 A1 12/2005 Hassler, Jr. et al.
2006/0009789 A1 1/2006 Gambale et al.
2006/0025789 A1 2/2006 Laufer et al.
2006/0025819 A1 2/2006 Nobis et al.
2006/0030884 A1 2/2006 Yeung et al.
2006/0058829 A1 3/2006 Sampson
2006/0089571 A1 4/2006 Gertner
2006/0089646 A1 4/2006 Bonutti
2006/0106288 A1 5/2006 Roth et al.
2006/0161186 A1 7/2006 Hassler, Jr. et al.
2006/0161256 A1 7/2006 Ziegler et al.
2006/0195139 A1 8/2006 Gertner
2006/0212053 A1 9/2006 Gertner
2006/0253131 A1 11/2006 Wolniewicz
2006/0264699 A1 11/2006 Gertner
2006/0265042 A1 11/2006 Catanese, III et al.
2006/0276871 A1 12/2006 Lamson et al.
2006/0282081 A1 12/2006 Fanton et al.
2007/0027358 A1 2/2007 Gertner et al.
2007/0049970 A1 3/2007 Belef et al.
2007/0060940 A1 3/2007 Brazzini et al.
2007/0073318 A1 3/2007 Carter et al.
2007/0073323 A1 3/2007 Carter et al.
2007/0088373 A1 4/2007 Baker
2007/0112363 A1 5/2007 Adams
2007/0112385 A1 5/2007 Conlon
2007/0129738 A1 6/2007 Kraemer et al.
2007/0167982 A1 7/2007 Gertner et al.
2007/0173869 A1 7/2007 Gannoe et al.
2007/0173888 A1 7/2007 Gertner et al.
2007/0179335 A1 8/2007 Gertner et al.
2007/0203517 A1 8/2007 Williams et al.
2007/0233170 A1 10/2007 Gertner et al.
2007/0235083 A1 10/2007 Dlugos
2007/0239284 A1 10/2007 Skerven et al.
2007/0250103 A1 10/2007 Makower
2007/0255308 A1 11/2007 Williams et al.
2007/0260259 A1 11/2007 Fanton et al.
2007/0270892 A1 11/2007 Makower
2007/0276293 A1 11/2007 Gertner
2007/0276432 A1 11/2007 Stack
2008/0009888 A1 1/2008 Ewers et al.
2008/0015501 A1 1/2008 Gertner
2008/0033488 A1 2/2008 Catanese, III et al.
2008/0039894 A1 2/2008 Catanese, III et al.
2008/0051823 A1 2/2008 Makower et al.
2008/0051824 A1 2/2008 Gertner
2008/0051850 A1 2/2008 Sparks et al.
2008/0058710 A1 3/2008 Wilk
2008/0071306 A1 3/2008 Gertner
2008/0082113 A1 4/2008 Bishop et al.
2008/0086082 A1 4/2008 Brooks
2008/0091237 A1 4/2008 Schwartz et al.
2008/0109027 A1 5/2008 Chen et al.
2008/0147002 A1 6/2008 Gertner
2008/0161717 A1 7/2008 Gertner
2008/0167519 A1 7/2008 St-Germain
2008/0167647 A1 7/2008 Gertner
2008/0167648 A1 7/2008 Gertner
2008/0172074 A1 7/2008 Baker et al.
2008/0172079 A1 7/2008 Birk
2008/0208240 A1 8/2008 Paz

FOREIGN PATENT DOCUMENTS

EP 1 602 392 A1 7/2005
EP 1 591 140 A1 11/2005
EP 1 547 642 B1 8/2007
EP 1 607 071 B1 8/2007
EP 1 670 361 B1 4/2008
FR 2 907 665 2/2008
WO WO 87/00034 1/1987
WO WO 99/25418 5/1999
WO WO 9925418 5/1999
WO WO 00/09049 2/2000
WO WO 00/18330 4/2000
WO WO 00/74573 A1 12/2000
WO WO 01/47435 7/2001
WO WO 02/035980 5/2002
WO WO 02071951 9/2002
WO WO 03/055420 7/2003
WO WO 03095015 11/2003
WO WO 2004004542 1/2004
WO WO 2004014237 2/2004
WO WO 2004019765 3/2004
WO WO 2004021894 3/2004
WO WO 2004/037064 5/2004
WO WO 2005007232 1/2005
WO WO 2005/009288 2/2005
WO WO 2005/018417 A2 3/2005
WO WO 2005/018417 A3 3/2005
WO WO 2005018417 3/2005
WO WO 2005018417 A2 3/2005
WO WO 2005018417 A3 3/2005
WO WO 2005020802 3/2005
WO WO 2005/094447 A2 10/2005
WO WO 2006/020370 2/2006
WO WO 2006/049725 A2 5/2006
WO WO 2006063593 A2 6/2006
WO WO 2006/108203 10/2006
WO WO 2006127431 11/2006
WO WO 2006134106 A1 12/2006
WO WO 2007017880 A2 2/2007
WO WO 2007/067206 A2 6/2007
WO WO 2007064906 A2 6/2007
WO WO 2007/110866 A2 10/2007

WO WO 2008/006084 A2 1/2008
WO WO 2008013814 1/2008
WO WO 2008/006084 A2 10/2008

OTHER PUBLICATIONS

Akira., JP63277063, Japanese and English Abstract, Nov. 15, 1988, pp. 1-4.
Abhyankar et al, Use of a tissue expander and a polyglactic acid (Vicryl) mesh to reduce radiation enteritis: case report and literature view, 21: pp. 755-757, Aug. 2005.
Buchwald, Overview of Bariatric Surgery, vol. 194, No. 3, Mar. 2002, pp. 367-375.
Burnett, et al., The Use of a Pelvic Displacement Prosthesis to Exclude the Small Intestine from the Radiation Field Following Radical Hysterectomy, 79, pp. 438-443, 2000. http://www.idealibrary.com.
Brolin, Robert E., Gastric Bypass. vol. 81, No. 5, Oct. 2001, pp. 1077-1095.
Cheng, Splenic Epidermoid Cyst, pp. 1-3, 1997.
Med-484P, Product Profile , Mar. 30, 2007, pp. 1-2.
DeMaria, Eric J., Laparoscopic Adjustable Silicone Gastric Banding. vol. 81, No. 5, Oct. 2001, pp. 1129-1143.
Deitel,Mervyn., Overview of Operations for Morbid Obesity. vol. 22, No. 9, Sep. 1998, pp. 913-918.
Doherty, Cornelius., Technique of Vertical Banded Gastroplasty. vol. 81, No. 5, Oct. 2001, pp. 1097-1111.
Foglia et al., Management of giant omphalocele with rapid creation of abdominal domain, 41, pp. 704-709, 2006.
Fried et al., Physical Principles of Available Adjustable Gastric Bands: How they Work. Obesity Surgery, 14, 2004, pp. 1118-1122.
Gertner MD, Stomach Restriction with an Extragastric Balloon, pp. 1, Abstract for 2007.
Geliebter et al; Extra-abdominal pressure alters food intake, intragastric pressure, and gastric emptying rate. 1986, pp. R549-R552.
Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, pp. 473-483, No. 7, vol. 60, Jul. 1994.
Hainaux et al., Laparoscopic adjustable silicone gastric banding: radiological appearances of a new surgical treatment for morbid obesity. 1999, Abdom Imaging 24: 533-537.
Konturek et al., Neuro-Hormonal Control of Food Intake; Basic Mechanisms and Clinical Implications, 2005, 56, Supp 6, 5-25. www.jpp.krakow.pl.
Lam et al., Huge Splenic Epidemoid Cyst: A Case Report, 1997; 60:113-6.
Laparoscopic Duodenal Switch, Mar. 24, 2006, http://wo-pub2.med.cornell.edu/chi.bin/WebObjects/PublicA.woa/5/w . . . p. 1-1.
Lee et al., Laparoscopic Vertical Sleeve Gastrectomy: A Novel Bariatric Procedure-superior to Estabilished Operations? pp. 1-27. 90th Annual Clinical Congress, New Orleans, LA, Oct. 10, 2004.
Malassagne, et al., Intra-abdonimal Sengstaken-Blakemore tube Placement for acute venous outflow obstruction in reduced-size Liver, Nov. 1996, 83, pp. 1086.
Marceau, et al., Malabsorptive Obesity Surgery. vol. 81, Oct. 2001, No. 5, pp. 1113-1127.
Mera, et al., Use of the Breast Implant for Liver Graft Malposition. vol. 5, No. 6, Nov. 1999, pp. 534-535.
Obesity Surgery Including Laparoscopy and Allied Care. vol. 16, No. 1, Jan. 2006, pp. 1-2. www.obesitysurgey.com.
Pomerri et al., Adjustable Silicone Gastric Banding of Obesity. , 1992, Gastrointest Radiol 17:207-210.
Schauer, et al., New applications for endoscopy: the emerging field of endoluminal and transgastric bariatric surgery, DOI:10.1007/s00464-006-9008-8, 2006.
The Sleeve Gastrectomy (or 2-Stage Procedure). 2006, pp. 1-2. http://surgicallyslim.com/sleeve.htm.
Walker, et al. Bladder Augmentation in Dogs Using the Tissue Capsule Formed Around a Perivesical tissue Expander, vol. 168, pp. 1534-1536, 2002.
Zwart et al., Gastric Motility: Comparison of Assessement with Real-Time MR Imaging or Barostat Experience1., 224: pp. 592-597, Aug. 2002.
Tucker, Diana, Medical Device Daily. vol. 10, No. 102, pp. 1-10, May 26, 2006.
Fried et al., Physical Principles of Available Adjustable Gastric Bands: How they Work. Obesity Surgery, 14, 2004, pp. 1118-1121.
Pomerri et al., Adjustable Silicone Gastric Banding of Obesity. , 1992, Gastrointest Radiol 17: pp. 207-210.
Schauer, et al., New applications for endoscopy: the emerging field of endoluminal and transgastric bariatric surgery, DOI: 10.1 007/s00464-006-9008-8, 2006.
McMillan, et al., Arthroscopic Knot-tying techiniques. pp. 81-95, 2003.
Buchwald—Overview of Barlatric Surgery. Journal of the American College of Surgeons. pp. 367-375, Mar. 2002.
Sharp, et al., The 4-S Modification of the Roeder Knot: How to Tie It. pp. 1004-1006, vol. 90, No. 6, Dec. 1997.
Schauer, et al., New application for Endoscopy: the emerging field of endoluminal and transgastric bariatric surgery. 10 pgs., Apr. 24, 2006.
Buchwald et al., "Bariatric Surgery: A Systematic Review and Meta-analysis", JAMA 2004, vol. 292, No. 14, pp. 1724-1737.
Buchwald et al., "Evolution of Operative Procedures for the Management of Morbid Obesity 1950-2000", Obesity Surgery 2002, 12:705-717.
Camerini et al., "Thirteen Years of Follow-up in Patients with Adjustable Silicone Gastric Banding for Obesity: Weight Loss and Constant Rate of Late Specific Complications" Obesity Surgery 2004, 14:1343-1348.
Cope et al., "Percutaneous Transgastric Technique for Creating Gastroenteric Anastomoses in Swine", Journal of Vascular and Interventional Radiology, 2004, 15:177-181.
Cummings et al., "Genetics and Pathophysiology of Human Obesity", An Annual Review of Medicine, 2003, 54:453-471/.
Johnston et al., "The Magenstrasse and Mill Operation for Morbid Obesity", Obesity Surgery 2003, 13:10-16.
Morino et al., "Laparoscopic Adjustable Silicone Gastric Banding Versus Vertical Banded Gastroplasty in Morbidly Obese Patients" Analysis Obesity Surgery vol. 238, No. 6, 2003, pp. 835-842.
Roman et al., "Intragastric Balloon of Non-Morbid Obesity: A Restrospective Evaluation of Tolerance and Efficacy", Obesity Surgery, 2004, 14:539-544.
Sallet et al., Brazillian Multicenter Study of the Intragastric Ballon: Obesity Surgery, 2004, 14, pp. 991-998.
Sjostrom et al., Lifestyle, Diabeters, and Cardiovascular Risk Factors 10 years after Bariatric Surgery, New England Journal of Medicine, 2004, 351, (6) 2683-2693.
Smith et al., "Modification of the Gastric Partitioning Operation for Morbid Obesity", Am. J. Surgery 142, Dec. 1981 pp. 725-730.
Smith et al., "Results and Complications of Gastric Partitioning: Four Years Follow-Up of 300 Morbidity Obese Patients", The American Journal of Surgery, 1983, (146) pp. 815-819.
Trumble et al., "Method for measuring long-term function of muscle-powered implants via radiotelemetry" J. Appl. Physiol. 2001,90: pp. 1977-1985.

* cited by examiner

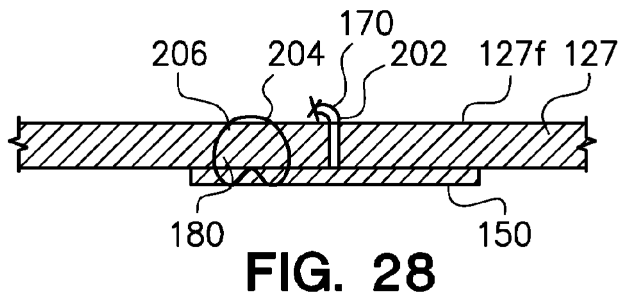
FIG. 28
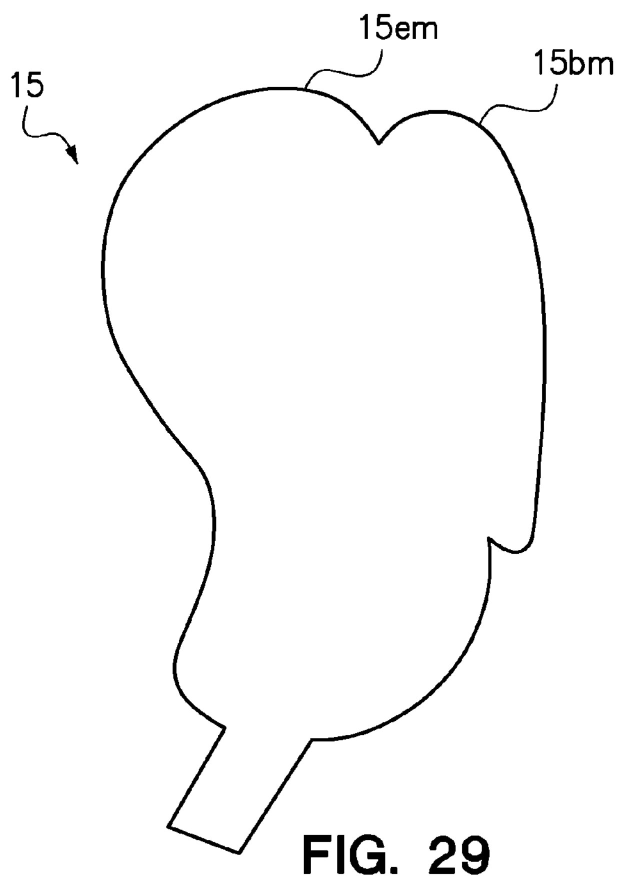
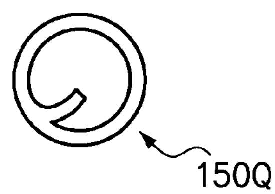
FIG. 26D
FIG. 29

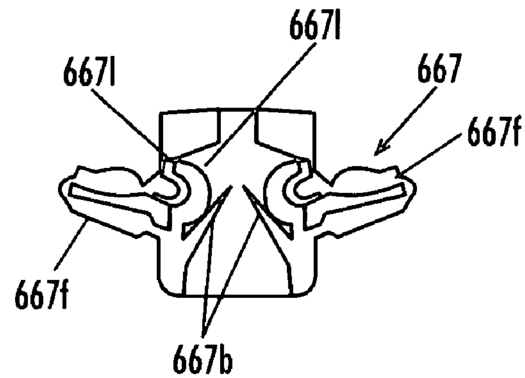
Fig. 36E
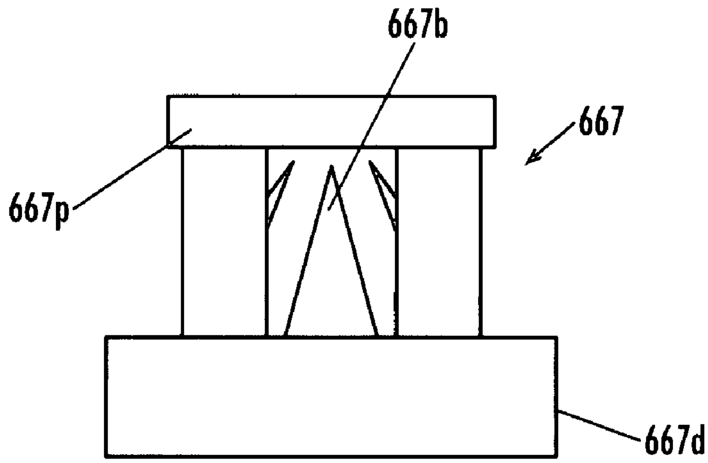
Fig. 36F
Fig. 36G
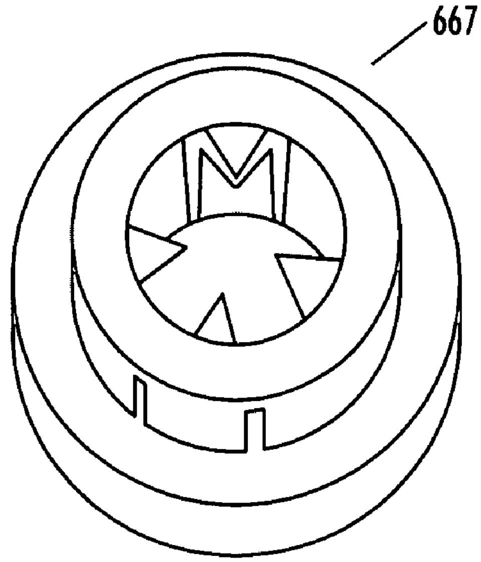

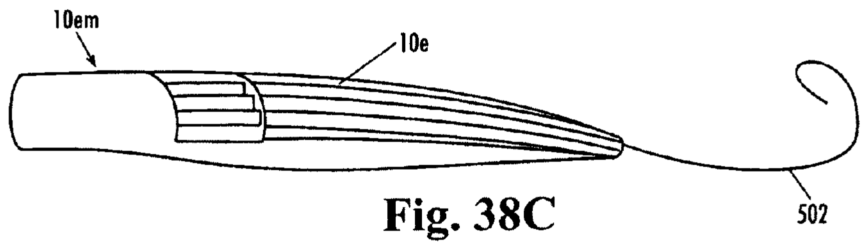
Fig. 38C
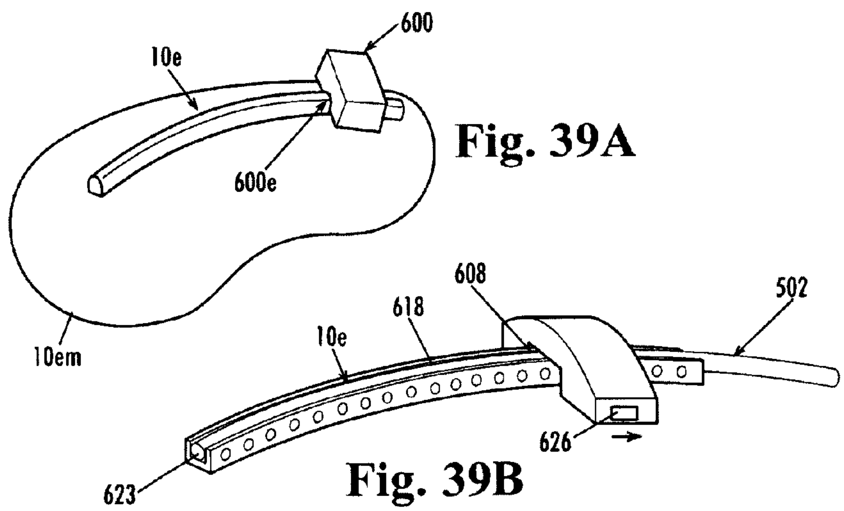
Fig. 39A
Fig. 39B
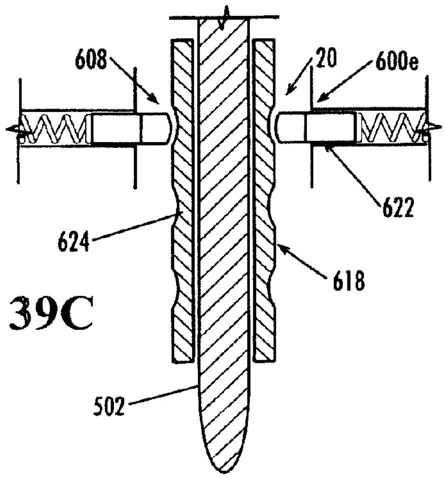
Fig. 39C

DEVICES AND METHODS FOR TREATMENT OF OBESITY

CROSS-REFERENCE

This application is a continuation-in-part application of application Ser. No. 11/407,701, now U.S. Pat. No. 8,070, 768, filed Apr. 19, 2006, which is incorporated herein by reference thereto, in its entirety, and to which application we claim priority under 35 USC §120.

This application claims the benefit of U.S. Provisional Application No. 60/833,284, filed Jul. 24, 2006, and U.S Provisional Application No. 60/877,595, filed Dec. 28, 2006, both of which applications are hereby incorporated herein, in their entireties, by reference thereto.

This application also hereby incorporates herein by reference thereto, in its entirety, co-pending application Ser. No. 11/716,985 filed on even date herewith, and titled "Devices and Methods for Treatment of Obesity".

FIELD OF THE INVENTION

The present invention relates to treatment of obesity, more particularly to implantable devices and methods of implanting the devices in the abdominal cavity to treat an obese patient.

BACKGROUND OF THE INVENTION

Obesity has become a major health concern, both nationally and internationally. The National Center for Health Statistics (NCHS) estimates that over 120 million Americans are overweight, including about 56% of the adult population. Of these, about 52 million are considered obese, as measured by a body mass index (BMI) of 30 or greater. In Europe, an estimated 77 million people are obese, as measured by the same standard. This problem is not limited to western nations, as many developing countries are reported to have obesity rates over 75% of the adult population.

Co-morbidities that are associated with obesity include, but are not limited to type II Diabetes, high blood pressure, sleep apnea, stroke and arthritis, the symptoms of which often tend to be lessened or alleviated upon loss of weight by a person so affected.

In the U.S., options for treatment of obesity are currently quite limited. Current treatment methodologies typically rely upon surgically introducing a "malabsorptive" environment in the gastro-intestinal tract, a restrictive environment, or a combination of these. One available treatment method is gastric bypass surgery and another is referred to as gastric banding (one of these techniques is referred to as the LAP-BAND™ procedure). These procedures are limited to only those patients with a BMI over 40 (or over 35, with co-morbidities present).

Gastric bypass procedures incur a great deal of morbidity and create a malabsorptive state in the patient by bypassing a large portion of the intestines. Serious side effects, such as liver failure have been associated with this procedure, as well as chronic diarrhea. Another surgical procedure that has a high degree of morbidity associated with it is known as the "Gastric Bypass Roux-en-Y" procedure. This procedure reduces the capacity of the stomach by creating a smaller stomach pouch. The small space holds only about one ounce of fluid. A tiny stomach outlet is also surgically created to slow the speed at which food leaves the stomach. Staples are used to create a small (15 to 20 cc) stomach pouch, with the rest of the stomach being stapled completely shut and divided from the stomach pouch. The small intestine is divided just beyond the duodenum, brought up, and connected to the newly formed stomach pouch. In addition to the considerable morbidity associated with this procedure, other disadvantages include "dumping syndrome", where stomach contents are literally "dumped" rapidly into the small intestine which may lead to nausea, weakness, sweating, faintness, and diarrhea; hernias resulting from the surgery; gallstones; leakage of the connection between the pouch and the intestine; stretching of the pouch that was formed; nutritional deficiencies; and possible dehiscence of the staples.

The LAPBAND™ is a band that, when placed, encircles the fundus-cardia junction and is inflatable to constrict the same. It does not reduce the volume of the stomach, but rather restricts passage of food into the stomach, the theory being that the patient will feel satiety with a much smaller volume of food than previously. Although the LAPBAND™ procedure is less invasive than a gastric bypass procedure, it also typically achieves less weight loss. Further, it is not a simple procedure and requires a substantial amount of training by a surgeon to become proficient in performing the procedure. Also, a substantial amount of dissecting and suturing is required because the pathway by which the band is introduced is not an existing pathway, and must be established by dissection. Great care is required to avoid blood vessels and nerves that may be in the intended pathway to be created by the dissection. After placing the band around the fundus-cardia junction, the ends of the band must be connected together and then it must be cinched down into place. Additionally, complications such as erosion at the fundus-cardia junction, slippage of the band from its intended location, nausea/vomiting, gastroesophageal reflux, dysphagia and lack of effectiveness in causing weight loss have been reported.

Intragastric balloons have also been placed, in an attempt to fill a portion of the volume in the stomach, with the theory being that it will then require less food than previously, to give the patient a sensation of fullness or satiety. This procedure involves delivery of a balloon (typically, transorally) to the interior of the stomach and inflation of the balloon to take up a portion of the volume inside the stomach. However, intragastric balloons may also lead to complications such as obstruction, vomiting and/or mucosal erosion of the inner lining of the stomach. The balloon can break down over extended exposure to the stomach's acids, and in some cases, after breaking down, the balloon translated through the intestines and caused a bowel obstruction.

Gastrointestinal sleeves have been implanted to line the stomach and/or a portion of the small intestines to reduce the absorptive capabilities of the small intestine and/or to reduce the volume in the stomach, by reducing the available volume to the tubular structure of the graft running therethrough. Although weight loss may be effective while these types of devices are properly functioning, there are complications with anchoring the device within the stomach/GI tract, as the stomach and GI tract function to break down things that enter into them and to move/transport them through. Accordingly, the integrity of the anchoring of the device, as well as the device itself may be compromised over time by the acids and actions of the stomach and GI tract.

A sleeve gastrectomy is an operation in which the left side of the stomach is surgically removed. This results in a much reduced stomach which is substantially tubular and may take on the shape of a banana. This procedure is associated with a high degree of morbidity, as a large portion of the stomach is surgically removed. Additionally, there are risks of complications such as dehiscence of the staple line where the staples are installed to close the surgical incisions where the portion of the stomach was removed. Further, the procedure is not reversible.

In the laparoscopic duodenal switch, the size of the stomach is reduced in similar manner to that performed in a sleeve gastrectomy. Additionally, approximately half of the small intestine is bypassed and the stomach is reconnected to the shortened small intestine. This procedure suffers from the same complications as the sleeve gastrectomy, and even greater morbidity is associated with this procedure due to the additional intestinal bypass that needs to be performed. Still further, complications associated with malabsorption may also present themselves.

An inflatable gastric device is disclosed in U.S. Pat. No. 4,246,893, in which a balloon is inserted anteriorly of the stomach and posteriorly of the left lobe of the liver. The balloon is then inflated to compress the stomach so that it fills with less food that would ordinarily be possible. Not only does this device compress the stomach, but it also compresses the liver, as seen in FIG. 5 of the patent, which may cause complications with the liver function. Additionally, the balloon is simply placed into this location, and there is no assurance that it will not migrate and lose its effectiveness in compressing the stomach to the degree intended. Still further, the balloon is of a simple spherical design, and, as such, extends pressure outwardly in all directions, 360 degrees, in all planes. Accordingly, the liver is compressed just as much as the stomach is. Also, the compression forces against the stomach are not ideal, as the spherical balloon conformation does not match the conformation of the expanding stomach. The stomach is not spherical when expanded, or concave with a constant radius of curvature, but expands into a designated space that allows the fundus to expand preferentially more than other parts of the stomach.

Brazzini et al. in WO2005/18417 discloses at least two or more expandable devices used to treat obesity, in which the devices are inserted through the abdominal wall and anchored against the external surface of the stomach wall by an anchoring mechanism that extends through the stomach wall and fixes to the internal surface of the stomach wall.

U.S. Patent Publication No. 2005/0261712 to Balbierz et al. describes capturing a device against the outer surface of the stomach wall to form a restriction that appears to function similarly to the restriction imposed by the LAPBAND™. The anchoring of the devices disclosed relies upon placement of features against the internal wall of the stomach to form an interlock with the device which is placed against the external wall of the stomach.

U.S. Patent Publication Nos. 2005/0267533 and 2006/0212053 to Gertner disclose devices for treatment of obesity that use one or more anchoring mechanisms that are passed through the wall of the stomach to establish an anchor.

U.S. Pat. No. 6,981,978 to Gannoe discloses devices for reducing the internal cavity of the stomach to a much smaller volume, which may be used to carry out a bypass procedure. Stapling is employed to isolate the smaller volume in the stomach, and thus the same potential disadvantages are present as with other stapling procedures described herein.

U.S. Pat. No. 6,186,149 to Pacella et al. describes an occluder device that can be used as a dietary control device (see FIG. 8C). The occluder device is placed against the wall of the stomach and inflated to press inwardly on the stomach wall. A frame is wrapped around the stomach wall and is inflated to press against the stomach wall. However, there is no disclosure of how the frame might be adjusted to maintain a position relative to the stomach wall as the size of the stomach varies.

Gastric reduction techniques have been attempted, such as by inserting instruments trans-orally and reducing the volume of the stomach by stapling portions of it together. However, this technique is prone to failure due to the staples pulling through the tissues that they are meant to bind.

Techniques referred to as gastric pacing endeavor to use electrical stimulation to simulate the normal feedback mechanisms of a patient that signal the brain that the patient is full, or satiated. While these techniques are less invasive than some of the other existing treatments, statistics to date have shown that the amount of weight lost by using such techniques is less than satisfactory.

Currently marketed drugs for weight loss, such as XENICAL®, MERIDIA® and Phen fen have largely failed, due to unacceptable side effects and complications, and sometimes to an ineffective amount of weight loss. Other drugs that are on the horizon include ACCOMPLIA® and SYMLIN®, but these are, as yet, unproven.

The risk and invasiveness factors of currently available surgeries are often too great for a patient to accept to undergo surgical treatment for his/her obesity. Accordingly, there is a need for less invasive, yet effective surgical treatment procedures for morbidly obese patients (patients having a BMI of 35 or greater). Also, since the current surgical procedures are currently indicated only for those patients having a BMI of 40 or greater, or 35 or greater when co-morbidities are present, it would be desirable to provide a surgical procedure that would be available for slightly less obese patients, e.g., patients having a BMI of 30 to 35 who are not indicated for the currently available surgical procedures. It would further be desirable to provide a surgical procedure that would be indicated for obese patients having a BMI in the range of 30-35, as well as for more obese patients.

SUMMARY OF THE INVENTION

The present invention provides methods, devices, tools and assemblies for treating a patient to assist with weight loss. One method embodiment involves passing a device including an expandable member in a collapsed configuration and a buoyancy member into the abdominal cavity of the patient, and anchoring at least a portion of the expandable member, relative to at least one structure in the abdominal cavity.

A method of treating a patient is provided that includes the steps of passing a device into the abdominal cavity of the patient, wherein the device includes at least one attachment member extending from a main body portion thereof; positioning an inferior portion of the device in the abdominal cavity; and anchoring that at least one attachment member to an inner surface of the abdominal wall.

A method of treating a patient is provided that includes steps of: passing a guide rail into the abdominal cavity of the patient; passing an anchoring frame, guided by the guide rail, into the abdominal cavity; anchoring the anchoring frame to at least one structure in the abdominal cavity; passing a device, guided by the guide rail, into the abdominal cavity; and attaching the device to the anchoring frame.

A method of treating a patient is provided that includes steps of: passing a guide rail into the abdominal cavity of the patient, wherein the guide rail is selected from one of: at least one guidewire; at least one flexible wire facilitating viewing out of a distal end portion thereof from a proximal end portion thereof; at least one rod; or a flexible steerable catheter; passing an anchoring frame, guided by the guide rail, into the abdominal cavity; anchoring the anchoring frame to at least one structure in the abdominal cavity; passing a device, guided by the guide rail, into the abdominal cavity; and attaching the device to the anchoring frame.

A method of treating a patient is provided, including steps of: passing an anchoring frame into the abdominal cavity of the patient; delivering anchoring members, attached to the anchoring frame, through at least one structure in the abdominal cavity that the anchoring frame is to be anchored to, through the skin and out of the patient; fixing the anchoring members externally of the abdominal cavity to anchor the anchoring frame to the at least one structure in the abdominal cavity; passing a device, into the abdominal cavity; and attaching the device to the anchoring frame.

A method of treating a patient is provided, including steps of: passing a buoyancy member into the abdominal cavity of the patient; anchoring the buoyancy member to at least one structure in the abdominal cavity; passing a device into the abdominal cavity; and attaching the device to the buoyancy member.

A method of treating a patient is provided, including steps of: passing a device including an expandable member having at least one trans-abdominally detectable marker; advancing the device into the abdominal cavity of the patient while tracking and guiding the advancing by trans-abdominally detecting the location of the at least one marker, relative to the patient's anatomy, as the device is advanced; and anchoring at least a portion of the expandable member, relative to at least one structure in the abdominal cavity.

A method of monitoring functionality of a device implanted in the abdominal cavity of a patient to enhance weight loss is provided, including: providing a handheld monitoring device outside of the patient; and wirelessly communicating with at least one sensor on the device located in the abdominal cavity.

A method of treating a patient is provided, including: providing a device implanted in the abdominal cavity of the patient, wherein the device occupies a space in the abdominal cavity to perform at least one of: prevention of expansion of the stomach of the patient into the space and compression of a portion of the stomach; wherein the device includes at least one electrode on a surface thereof in contact with the stomach of the patient, said at least one electrode being electrically connected to a stimulation signal controller; and delivering a stimulation signal from the controller to the at least one electrode to stimulate at least one contraction of at least one muscle in the stomach.

A method of treating a patient is provided, including: passing a device into the abdominal cavity of the patient; anchoring at least a portion of the device, relative to at least one structure in the abdominal cavity; and occupying a space in the abdominal cavity with the device to substantially restrict expansion of the fundus of the stomach, and restraining the stomach to a shape resembling a tube, but wherein at least a portion of the antrum is left unrestrained.

A method of treating a patient is provided, including: passing a device into the abdominal cavity of the patient; anchoring at least a portion of the device, relative to at least one structure in the abdominal cavity; and occupying a space in the abdominal cavity with the device to substantially restrict expansion of the fundus of the stomach, and restraining the stomach to a shape resembling a tube, but wherein a small pouch is left unrestrained at a superior end portion of the stomach.

An implantable device for treatment of a patient to assist weight loss is provided, wherein the device includes: an expandable member configured to be positioned in an abdominal cavity of the patient, the expandable member configured to be expanded from a contracted configuration to an expanded configuration after placement of the device in the abdominal cavity, and to substantially maintain a size and shape of the expanded configuration. The expandable member, in the expanded configuration, has a buoyancy characteristic relative to its surrounding when implanted in the abdominal cavity. The device further includes a buoyancy member having a buoyancy characteristic different from the buoyancy characteristic of the expandable member, to alter a combined buoyancy characteristic of the device.

A method of making an implantable device for treatment of a patient to assist weight loss is provided, wherein the device includes an expandable member configured to be positioned in an abdominal cavity of the patient, the expandable member configured to be expanded from a contracted configuration to an expanded configuration after placement of the device in the abdominal cavity, and to substantially maintain a size and shape of the expanded configuration, and a buoyancy member fixed to the expandable member and contained within an internal cavity of the expandable member. The method of making includes: providing a mold having a shape of the buoyancy member integral with a shape of the expandable member; molding a wall of polymeric material over the mold; removing the molded wall of material from the mold; inverting a molded buoyancy member portion of the wall into an internal cavity defined by a molded expandable member portion of the wall; and sealing a slit remaining from the inverting.

An anchoring frame deployment tool is provided that includes: a recess or cavity formed in a distal portion shaped and dimensioned to receive an anchoring frame therein; needles and a driving mechanism for driving the needles through the distal portion and the anchoring frame; wherein the needles have sufficient length to extend through an abdominal wall of a patient and out through the skin of the patient when the anchoring frame is contacted to an inner wall surface of the abdominal wall.

An anchoring frame for anchoring a device to an internal structure in a patient's body is provided, including: a plurality of beams linked to be compressed into a narrow configuration and expanded to an expanded configuration; and a mechanical linking feature on each of at least two of the beams, the mechanical linking features configured to mechanically engage with mating features on the device.

An assembly of mating engagement members for engaging an intra-abdominal, extra-gastric implant device with an anchoring frame is provided, wherein the assembly includes: a rail having a series of transversely placed openings along a length thereof; a channel configured to receive the rail and having at least one detent configured to pass through a wall of the rail through one of the openings; and an actuator for preventing the at least one detent from passing through the wall when in a first configuration; and allowing passage of the at least one detent through the wall when in a second configuration.

These and other features of the invention will become apparent to those persons skilled in the art upon reading the details of the methods, devices, tools and assemblies as more fully described below.

BRIEF DESCRIPTION OF THE DRAWINGS

FIG. 26D illustrates an example of a Q-ring that can be used in various embodiments of the present invention.

FIG. 28 schematically illustrates one suture having been tied down to anchor a portion of a tab to the inner surface of the abdominal wall.

FIG. 29 shows a mold that is three dimensionally shaped to form an expandable member and a buoyancy member integrally as a single molded product.

FIGS. 36D-36E illustrate another embodiment of a speed nut that is configured to assume undeployed (or extended) and deployed (or compressed) configurations or states.

FIGS. 36F-36G show side and perspective views of another embodiment of speed nut.

FIG. 37C shows a needle in a retracted configuration, and FIG. 37D shows the needle protruding through the arm or beam and ingrowth sheet.

FIG. 38C illustrates an expandable member in a compacted, low profile configuration for insertion into the abdominal cavity of a patient, with the central lumen of a rail having been threaded over a guidewire for sliding delivery and guidance of the device into the abdominal cavity.

FIGS. 39A-39C illustrate another embodiment of mating engagement members.

DETAILED DESCRIPTION OF THE INVENTION

Figure 1:
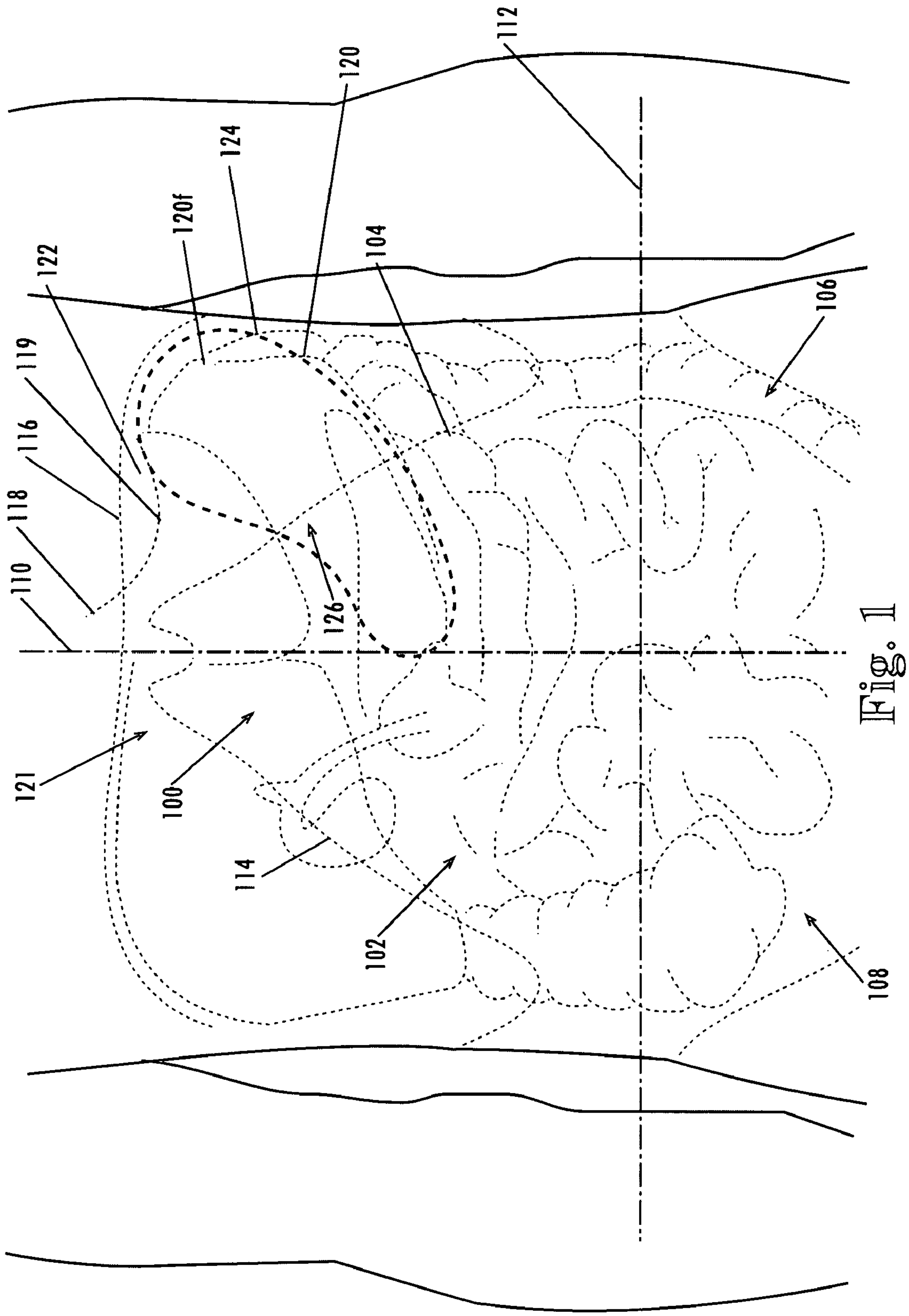
FIG. 1 illustrates the anatomy of the abdominal cavity and its contents, and surrounding features.

Before the present devices methods and instruments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a conduit" includes a plurality of such conduits and reference to "the expandable member" includes reference to one or more expandable members and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "compliant" material refers to a material that is stretchable or expandable. This expansibility allows the material to increase in dimension substantially more than a noncompliant or semi-compliant material, prior to failure. For example, when formed as a balloon structure, a compliant material comprises an expansibility property of being able to increase its radius, beyond its formed radius, under pressure applied into the balloon, by 100 percent or more, without rupturing.

A "noncompliant" material refers to a material that, when formed as a balloon structure, can increase its radius beyond its formed radius, under pressure applied into the balloon, only up to about 10 percent or less prior to rupturing.

A "semi-compliant" material refers to a material that, when formed as a balloon structure, can increase its radius beyond its formed radius, under pressure applied into the balloon, by an amount between about 10 percent and about 100 percent, prior to rupturing.

The "wall" of the stomach refers to all of the layers that make up the stomach wall, including the mucosa, submucosa, muscular layers and serosa. A "layer", "layer of the stomach wall" or "stomach wall layer" refers to a mucosal layer, submucosal layer, muscular layer or serosal layer.

A "proximal" end of an instrument is the end that is nearer the surgeon when the surgeon is using the instrument for its intended surgical application.

A "distal" end of an instrument is the end that is further from the surgeon when the surgeon is using the instrument for its intended surgical application.

An "internal body structure" when referred to as a structure to which a device is to be anchored, refers to a structure internal to the skin of a patient, and which can be within the abdominal cavity of the patient, or just outside of it, such as including the outer surface of a wall that partially defines the abdominal cavity. Structures to which a device can be anchored include, but are not limited to: one or more ribs, the intercostal muscles, the abdominal surface of the diaphragm, the stomach (but where the anchor does not pass through the wall of the stomach), the anterior abdominal wall, the posterior abdominal wall and the lateral abdominal wall, the esophagus, the angle of his in the stomach, the gastro-intestinal junction, the gastro-esophageal junction, the columnar ligaments of the diaphragm near the gastro-esophageal junction, the superior aspect of the omentum, peritoneum, liver, connective tissues, ligaments, and blood vessels.

An "internal abdominal structure" refers to an internal body structure that is within the abdominal cavity of the patient, including the abdominal wall. For example, attachment to an inner wall surface of the abdominal wall is an attachment to an internal abdominal structure.

The preferred embodiments of the present invention prevent the possible issue of erosion caused by an expandable member, by not requiring anchoring to the stomach, and further, by not requiring a substantial compression force to be applied when the stomach is not full of food. By allowing the stomach to move freely in the constrained spaced provided by the expandable member, the stomach's possible expansion size will be decreased, but there will be less opportunity for the formation of pressure necrosis since no one region will be subjected to concentrated forces. With the device in place, there is substantially no distensibility of the stomach as normal exists with an unconstrained stomach. With distensibility restricted and gastric volume reduced, as the patient ingests food, the intra-gastric pressure will rise to a level sufficient to produce satiety without distension or volume expansion of one or more regions of the stomach. The device occupies so much volume in the abdominal cavity that the stomach does not substantially depart from the shape set by the device even when filled with food. Another physiological benefit of the device is that the stomach's ability to relax in response to ingestion of food is reduced or eliminated, through producing earlier satiety. One additional physiological benefit of the expandable member may further be to substantially reduce the actual volume of the stomach itself, remodeling the organ as the muscle contracts into its new shape over the period of weeks or months (just as the heart remodels when constrained from over-expansion). Remodeling the stomach allows the expandable member to be implanted temporarily. The preferred embodiments also are positioned in a location to substantially fill the space normally occupied by the fundus, thus moving the stomach medially and wedging the stomach between the expandable member and the medial and anterior aspects of the liver, and the spine posteriorly. This position also ensures that the expandable member is almost entirely maintained underneath the diaphragmatic umbrella beneath the ribs on the left side, thus concealing the expandable member, and preventing it from producing an unsatisfactory cosmetic result. Further, the preferred embodiments can have elements for anchoring on one or more locations along the abdominal cavity wall to prevent migration. Further, the preferred embodiments are provided with an outer surface that is very atraumatic. Embodiments described may include at least one expandable member, preferably an inflatable member, made of a material or material composite that is impermeable to fluid, which may be substantially impermeable to gas and is at least impermeable to liquid, as well as embodiments having at least two expandable members, with one expandable member being inflated with a gas and another expandable member being inflated with a liquid. Other embodiments include an expandable member and a buoyancy member that may or may not be expandable, and which adds buoyancy to the device. For example, a buoyancy member may be included with a liquid-filled expandable member of a device, that by itself, has negative buoyancy, so that the buoyancy member provides positive buoyancy to bring the combined buoyancies of these components of the device nearer to a neutral buoyancy, when implanted into the abdominal cavity of a patient. It can be beneficial to make the combined buoyancy slightly positive in the abdominal cavity to help prevent the device from migrating down in the patient.

The devices described herein can be provided as versatile devices. For example, the same device with an expandable member can be implanted and attached to either in a laparoscopic surgical procedure, an oral trans-gastric procedure, or a variation of percutaneous procedures in which non general anesthesia and little or no insufflation are used. The device can be implanted and anchored directly to at least one internal abdominal structure, or alternatively, can be implanted by fixing to an anchoring frame having been anchored to at least one internal abdominal structure.

Abdominal Cavity Anatomy

Figure 2A:
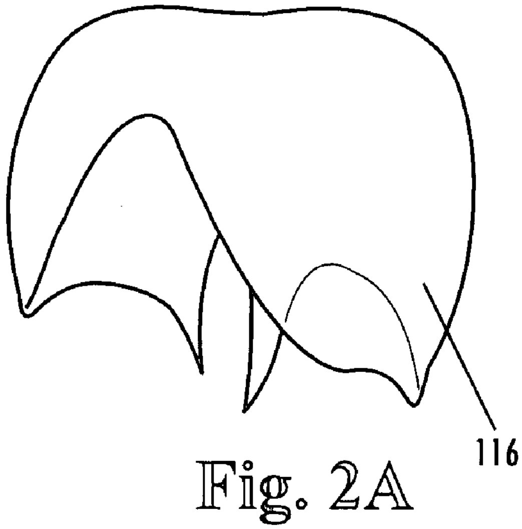
FIG. 2A is an illustration of a diaphragm in an isolated view, illustrating the conformation of the diaphragm as it exists in the body.
Figure 2B:
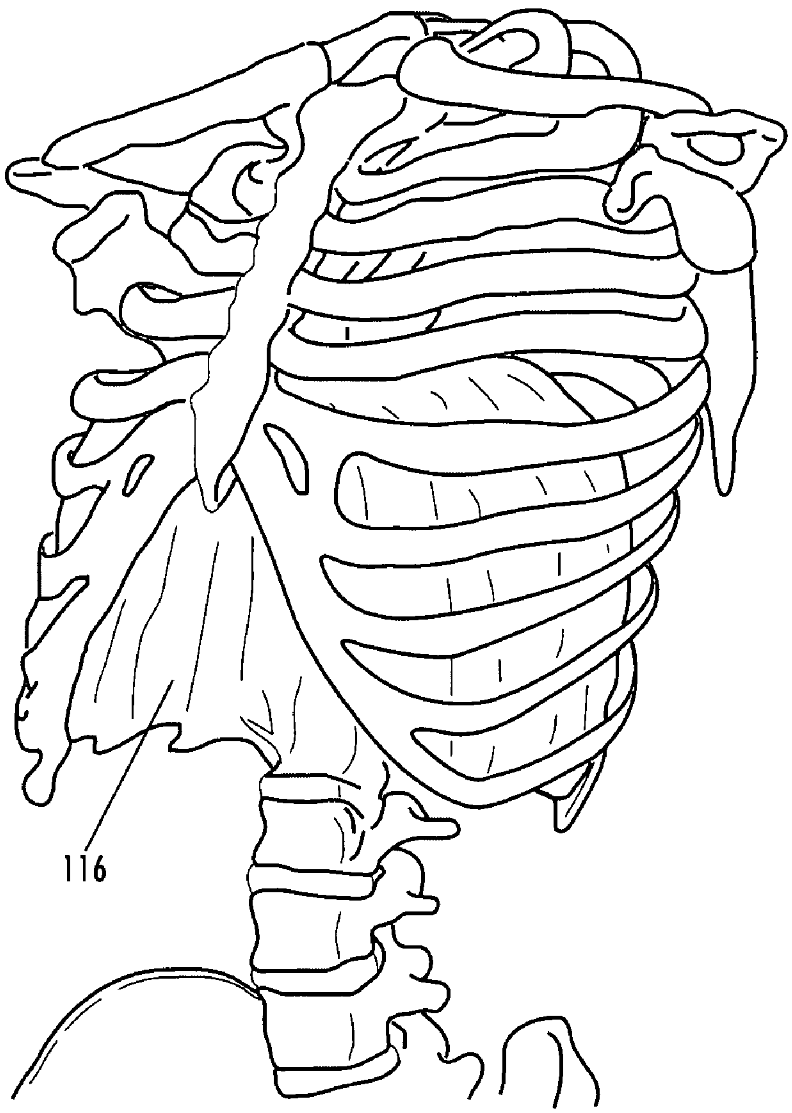
FIG. 2B illustrates the diaphragm in position relative to the rib cage.

FIG. 1 illustrates the anatomy of the abdominal cavity and its contents, and surrounding features. The abdominal cavity 100 is shown divided among four quadrants, the upper right quadrant 102, upper left quadrant 104, lower left quadrant 106 and lower right quadrant 108, as divided by the median axis 110 and transverse axis 112. The lower edge of the ribcage is illustrated by the dotted line 114 and the diaphragm is shown at 116. As seen in FIGS. 2A and 2B, the diaphragm 116 is shaped like a parachute and sits within the ribs. The esophagus 118 passes through the diaphragm 116 and joins with the stomach 120. The left lobe 122 of the liver 121 lies anteriorly of the esophagus 118 and the fundus-cardia junction 119. In one aspect of the invention, an expandable device is implanted in an extra-gastric location (i.e., outside of the stomach) generally indicated at 124, and then expanded to occupy a space that the fundus of the stomach would ordinarily expand into when the stomach is filled with food. The expanded device prevents this expansion by the fundus, thereby limiting the volume of the cavity in the stomach to a much smaller volume than if the fundus had been allowed to expand into the space. Alternatively, the device is expanded to apply pressure to the fundus of the stomach in a downward direction (e.g., in a direction toward the transverse axis 112 shown, with some transverse movement toward the median axis 110 shown), and optionally, additionally to the main body of the stomach, to reduce the volume inside the stomach to effect satiety in the patient with relatively less food ingested, relative to what the patient would require for satiety without the implant in place.

Devices

At least some embodiments of devices described herein can be implanted percutaneously, with a relatively quick and simple procedure that requires no general anesthesia and wherein only a single, small opening in a patient is required to deliver the device, which typically has a single expandable member that is self anchoring or can be easily anchored to maintain the simplicity and minimal invasiveness of the procedure.

In other embodiments, configurations of expandable members are provided, where a device can contain one or more expandable members and one or more steps of implantation and anchoring may be performed laparoscopically with remaining steps being performed percutaneously. Further alternatively, implantation and anchoring a device may be performed with most if not all steps being performed laparoscopically or orally through a trans-gastric procedure. Any of the devices described herein can, of course, be implanted using open surgical procedures. Devices that can be implanted percutaneously can alternatively be implanted using laparoscopic procedures.

Devices described herein can be implanted permanently, but are also configured for reversibility, to facilitate relatively simple removal procedures, should it be desired to remove a device. Alternatively, devices according to the present invention can be implanted temporarily, such as over a period of months, and then removed or disabled when further treatment is no longer required, or to allow an alternative treatment to be applied.

Device Body Configurations

Figure 3A:
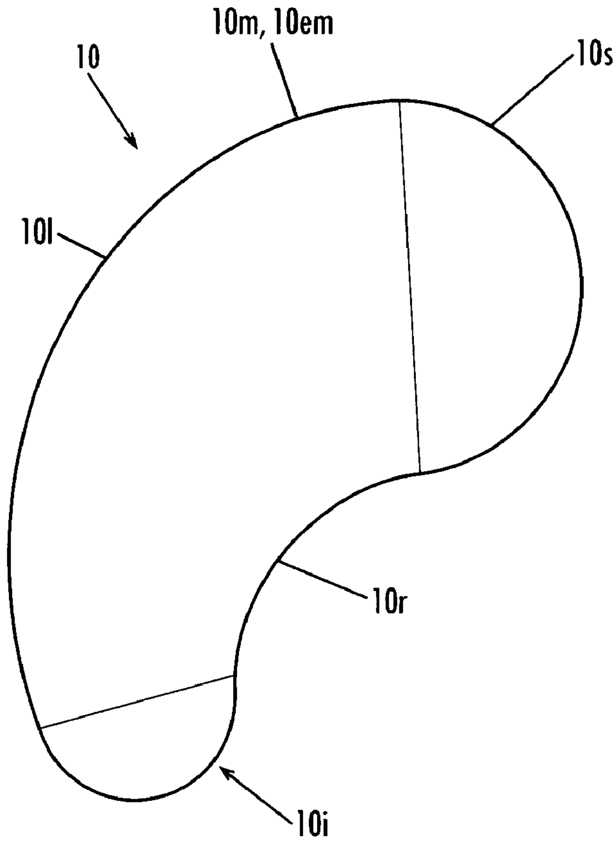
FIGS. 3A and 3B show views of a main body of a device with a shape and size approximating the shape and size of a full (post-prandial) stomach.
Figure 3B:
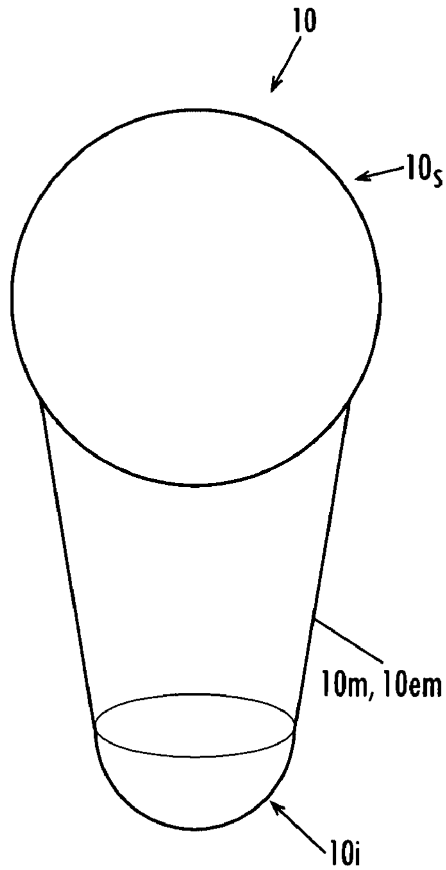

FIGS. 3A and 3B show views of a device 10 having a main body 10*m*,10*em* with a shape and size approximating the shape and size of the full (post-prandial) stomach 120. Although main body 10*m* need not be expandable/collapsible to perform restriction of stomach expansion, main body 10*m* is typically formed from one or more expandable members 10*em* as will be described in further detail below, for better performance of intended functions and to allow less invasive procedures for implanting the same.

Main body 10*m*,10*em* includes curved left and right sides 10*l* and 10*r*, respectively (FIG. 3A shows the posterior surface of main body 10*m*,10*em*), wherein the left side 101 is convex and the right side 10*r* is concave such that the main body 10*m*, 10*em* takes on the shape of a portion of the full stomach that expands from the shape of a substantially empty stomach. The superior portion 10*s* is substantially larger and more bulbous than the inferior portion 10*i*, since the fundus portion of the stomach 120 expands much more than the antrum upon receiving food. Thus, as seen in the right side view of FIG. 3B, the superior portion 10*s* is very bulbous and almost spherical, with a larger cross section than the inferior portion 10*i*, while the inferior portion is more nearly hemispherical, with the center portion of the main body tapering from the superior portion 10*s* to the inferior portion 10*i*. Configured as such, the main body 10*m*,10*em*, when implanted properly, will occupy the space that naturally exists from the stomach 120 to expand into when expanding from a pre-prandial configuration to a post-prandial configuration. By severely limiting this expansion capability, the patient is thereby able to consume only a significantly smaller volume of food than possible if the implant were not present.

Device 10 sizes will likely vary depending on the size of the skeletal system of the patient into which device 10 is to be implanted, particularly the size of the rib cage. Further variations may be made to tweak or adjust the amount of restriction along any desired location of the stomach that interfaces with device 10. One typical variation is in the length and/or size (diameter or expandability capacitance) of the inferior portion 10*i*. In some embodiments, the inferior portion 10*i* of the expandable member 10*em* may be made longer than shown in FIGS. 3A-3B to extend further inferiorly and medially than the inferior portion of the expandable member shown in FIGS. 3A-3C.

At least a portion of main body member 10*m* may be expandable. The entire main body 10*m* may be made of an expandable member 10*em*. When in an expanded configuration, expandable member 10*em* can optionally only abut or lie adjacent to the pre-prandial stomach wall, without imparting any significant deformation forces thereto. However, when the patient eats and the stomach begins to fill, expandable member 10*em* in this case prevents the stomach 120 from expanding into the volume occupied by expandable member 10*em*. In such a case, the stomach 120 becomes “deformed” as it attempts to expand and can only expand in a limited fashion, if at all, around a portion of the perimeter of expandable member 10*em*. Thus, upon expanding the device 10, the device 10 expands in the space(s) normally occupied by the stomach 120 as the stomach 120 expands when receiving food. Thus device 10 exerts pressure on, or at least prevents expansion of the fundus and optionally, the antrum. In embodiments where the expandable device 10 is not attached to the stomach, the stomach is free to perform its normal function of mixing food in the stomach for digesting and pushing food out of the stomach. During all of this movement the stomach may slip behind, beside or on top of the expandable device, but the internal volume of the stomach will be held to its smaller volume as the expandable device 10*em* is occupying the space into which the stomach would normally expand. Further details of methods for treatment of obesity, including procedures for implanting devices described herein are described below.

Figure 4:
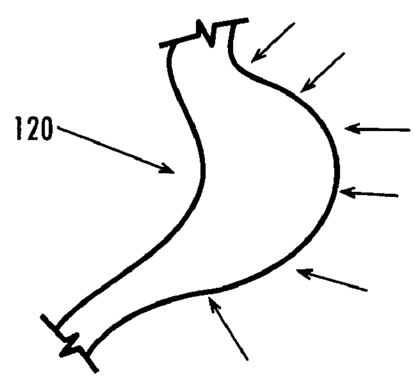
FIG. 4 illustrates (by arrows) potential locations on the stomach wall that can be displaced or compressed by one or more expandable devices as described herein.

As noted above, an expandable device 10 can be implanted adjacent a surface of the stomach wall, either in contact therewith or at a predetermined distance therefrom, to prevent expansion of the stomach 120 into a volume occupied by the expandable device 10. Alternatively, some embodiments of the devices described herein can be configured and placed to exert an external compression on one or more locations of the stomach to deform the stomach wall, thereby decreasing the internal volume of the cavity within the stomach that accepts food and liquid intake. FIG. 4 illustrates (by arrows) potential locations on the stomach 120 wall that can be compressed (or restricted from expanding) by one or more devices 10 as described herein.

In one embodiment, expandable member 10*em* shown in FIGS. 3A-3B is composed of an inflatable member 10*em*. Inflatable members described herein can be inflated with gas or liquid or both. Examples of gases or liquids that can be used to inflate inflatable members/devices 10 include, but are not limited to: carbon dioxide, helium, isotonic dextrose solution, iostonic saline solution, air.

At least a portion of the expandable member 10*em* shown in FIGS. 3A-3B may be inflated with one or more gases, to provide a relatively lighter, less dense implanted device 10, relative to an expandable member completely filled with liquid. The entire expandable member 10*em* may be inflated with one or more gases. Alternatively, the entire expandable member 103*m* may be inflated with one or more liquids. Further alternatively, devices 10 can be at least partially inflated with a porous gel that is porous or microporous to encapsulate air or other gas bubbles, thereby reducing the weight of the gel while still permitting it to apply volumetric pressure to expand an inflatable member. Such gels may be settable, such as ultra-violet (uv) curable or otherwise chemically curable, or, alternatively, can remain in the gel state, so that they can be readily removed or added to, to increase or decrease the amount of inflation/expansion of the expandable member. Gels can be made from a flowable viscoelastic substance made of a polymer mixture, such as silicone oil, boric acid, hyaluronic acid, polyacrylic acid or combinations thereof, for example. The gel, as delivered into the expandable member 10*em* (e.g., such as by injection or the like) can be aerated or infused with carbon dioxide or an inert gas to create a deformable or non-deformable cellular structure that encapsulates the gas in cells, and thus has relatively low mass but still has significant resistance to compression or deformation.

When an expandable member is inflated solely with a pressurized gas, although this reduces the overall weight and density of the device 10, it may tend to be overly buoyant when implanted in a patient. Because a patient is made up primarily of water, the air, carbon dioxide, or other pressurized gas in expandable member tends to be very buoyant relative to its surroundings in the abdominal cavity, which are primarily water. Depending upon the orientation of the patient's abdominal cavity at any particular time, the buoyancy of such a device 10 may establish a force that tends to drive device 10 toward a location away from its intended, predefined location, and may cause the device 10 to tend to migrate away from its intended location to a less desirable position. Also, in the case of a device 10 having multiple expandable members where one is gas filled and one is liquid filled, the buoyancy of the gas filled expandable member may cause it to pull away from a liquid filled expandable member, particularly if the liquid filled expandable member is anchored to an internal structure, and this may cause undesirable results such as unwanted separation of the expandable members and/or failure of one or more of the expandable members.

Accordingly, it may be desirable to provide a device that has a density that is closely matched to the density of its surroundings when implanted in the abdominal cavity. Assuming that the abdominal cavity has a density of saline and is made entirely of saline, then an expandable member 10*em* filled with saline would be substantially neutrally buoyant when implanted within the abdominal cavity and would not exert any positive or negative buoyancy forces when implanted therein. At the other end of the spectrum, if the abdominal cavity were completely filled with fat, then a device having an expandable member 10*em* inflated with an oil matching the density of the fat could be implanted so as not to create any negative or positive buoyancy forces when implanted in the abdominal cavity. In reality, a typical abdominal cavity of a patient will include both water(saline) and fat, with relative amounts (percentages) of fat varying from patient to patient. Accordingly, device 10 can be designed to have a density somewhere in between the density of saline and that of fat, with the amount of buoyancy being relatively greater for those abdominal cavities having relatively more fat that those having relatively less fat.

Figure 5A:
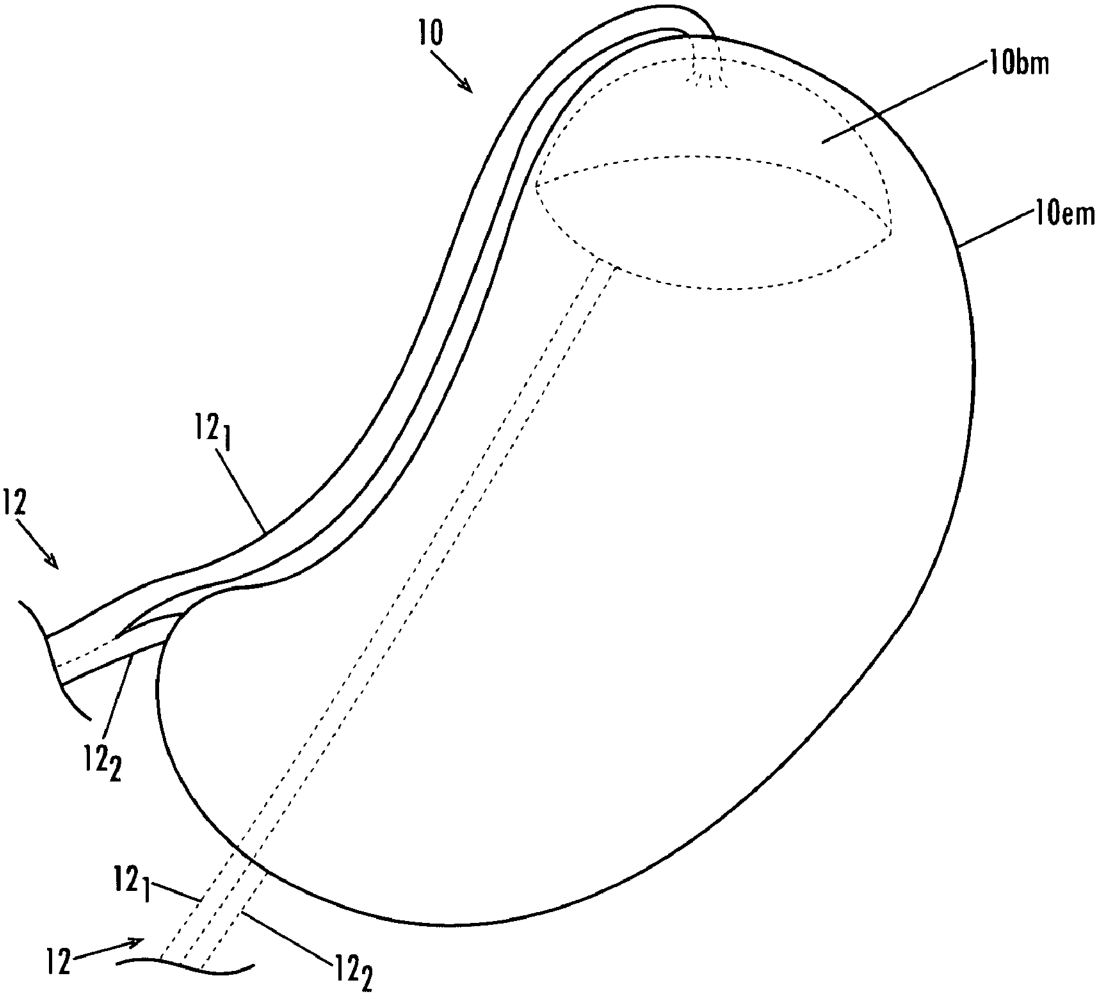
FIG. 5A shows an embodiment of a device having a buoyancy member contained in an internal chamber of an expandable member.

FIG. 5A shows an embodiment of device 10 having a buoyancy member 10*bm* contained in the internal chamber of expandable member 10*em*. For example, buoyancy member 10*bm* may be formed of a substantially gas impermeable material and can be inflated with air, $CO_2$, or other inert gas to reduce the overall density of device 10 in the expanded configuration shown in FIG. 5A. Expandable member 10*em* can be filled with a liquid, such as saline, dextrose solution, or other biocompatible liquid, for example, and this liquid interfaces with the external surface of buoyancy member 10*bm* in the expanded configuration shown. Buoyancy member 10*bm* can be shaped such that a superior portion thereof has a curvature that substantially matches the curvature of the superior end portion of expandable member 10*em*, such as shown in FIG. 5A, to that when inflated and when device 10 is implanted in the patient in the intended orientation and the patient is upright, buoyancy member 10*bm* floats to the superior end portion of expandable member 10*em* and fits in the apex of the superior portion to help secure buoyancy member 10*bm* at this location and minimize movement. The position of buoyancy member 10*bm* within expandable member 10*em* orients expandable member 10*em* such that the superior end of expandable member 10*em* is against or near the undersurface of the umbrella-shaped diaphragm 116, due to the buoyant effect of buoyancy member 10*bm* on expandable member 10*em*. Alternatively, buoyancy member 10*bm* may be fixed to the inner surface of expandable member 10*em*, by adhesives, or buoyancy member 10*bm* can be co-molded with expandable member 10*em*. Buoyancy member 10*bm* can be fixed in the position shown in FIG. 5A in at least one embodiment.

A conduit $\mathbf{12}_1$ can be provided in fluid communication with buoyancy member 10*bm* as shown in FIG. 5A, which has a length to allow a proximal end portion thereof to extend out of the body of the patient when device 10 is implanted in the desired location and orientation in the abdominal cavity of a patient and expanded. A conduit $\mathbf{12}_2$ can also be provided in fluid communication with expandable member 10*em*, and this conduit also has a length to allow a proximal end portion thereof to extend out of the body of the patient when device 10 is implanted in the desired location and orientation in the abdominal cavity of a patient and expanded. As shown, conduits $\mathbf{12}_1$ and $\mathbf{12}_2$ are integrated into a single tube 12 having two lumens $\mathbf{12}_1$ and $\mathbf{12}_2$ until the location where conduit $\mathbf{12}_2$ splits off to feed into expandable member 10*em* as conduit $\mathbf{12}_1$ continues on to join in fluid communication with buoyancy member 10*bm* after passing through the wall of expandable member 10*em*. The wall of conduit $\mathbf{12}_1$ is sealed with expandable member 10*em* to maintain expandable member 10*em* at least liquid impervious (and may optionally be substantially gas impervious). Likewise, conduit $\mathbf{12}_1$ is substantially gas impervious and joins in a sealed connection with buoyancy member 10*bm* to maintain it as a substantially gas impervious chamber. Conduit $\mathbf{12}_2$ is at least substantially liquid impervious joins in a sealed connection with expandable member 10*em* to maintain it as a substantially liquid impervious chamber, optionally as a substantially gas impervious chamber. Conduit $\mathbf{12}_1$ may run along the surface of expandable member 10*em* as shown and may be free of the surface of expandable member 10*em* except for where it inserts through the wall of expandable member 10*em*. Alternatively, conduit $\mathbf{12}_1$ may be fixed at one or more locations along its length that is adjacent to expandable member 10*em*, or the entire adjacent length may be fixed to the surface of expandable member 10*em*, such as by adhesive, taping, or other mechanical fixation.

Further alternatively, conduit $\mathbf{12}_1$ may extend inside of expandable member 10*em*, as illustrated in phantom lines in FIG. 5A. In this case, conduit $\mathbf{12}_1$ (as well as conduit $\mathbf{12}_2$) may connect with expandable member 10*em* at an inferior location, such as one that is closest to an opening though which device 10 is inserted during implantation, for example. Further alternatively, conduits $\mathbf{12}_1$ and $\mathbf{12}_2$ may be provided as completely separate conduits along the full lengths thereof.

In one particular embodiment, expandable member 10*em* is formed of silicone and buoyancy member 10*bm* is formed of silicone. However, buoyancy member may include at least one layer, or may be coated with a material that reduces the permeability of buoyancy member 10*bm* to gas when buoyancy member 10*bm* is in the expanded configuration shown in FIG. 5A. For example, buoyancy member may include a metallic layer or coating, such as titanium, silver, or other relatively inert, biocompatible metal. Alternatively, a silicone buoyancy member 10*bm* can be coated with parylene to appreciably reduce gas permeability of the buoyancy member 10*bm*. As another alternative, buoyancy member 10*bm* may be formed by co-extrusion, e.g., co-extruding EVOH (ethylene-vinyl alcohol copolymer) and polyurethane to form the buoyancy member 10*bm*, with or without a metallic coating as described above. As another alternative embodiment, buoyancy member 10*bm* may be formed of a blend of silicone and polyurethane. Further alternatively, the buoyancy member 10*bm* can be formed from or include one or more semi-compliant or non-compliant materials. Examples of useable semi-compliant materials include, but are not limited to: nylon, polyethylene, polyester, polyamide and polyurethane, see for example, U.S. Pat. No. 6,500,148, which is hereby incorporated herein, in its entirety, by reference thereto. Polyurethane, nylon, polyethylene and polyester can be compliant or semi-compliant materials, depending upon the specific formulation and hardness or durometer of the material as produced. Examples of noncompliant materials that can be used in the construction of inflatable members described herein include, but are not limited to: polyethylene terepthalate (PET) and urethane. Expandable member 10*em* can optionally be formed in any of the manners described above with regard to buoyancy member 10*bm*.

Figure 5B:
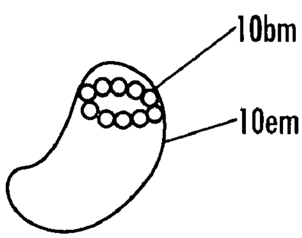
FIGS. 5B-5C schematically illustrate alternative embodiments of buoyancy members.
Figure 5C:
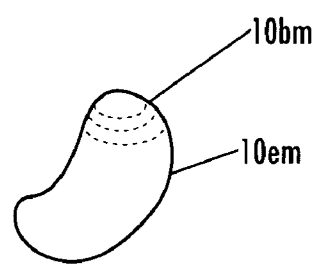

FIGS. 5B-5C schematically illustrate alternative embodiments of buoyancy members 10*bm*, wherein in FIG. 5B, buoyancy member 10*bm* comprises a ring of gas-filled beads, and in FIG. 5C, buoyancy member 10*bm* comprises a gas-filled coil.

Figure 6A:
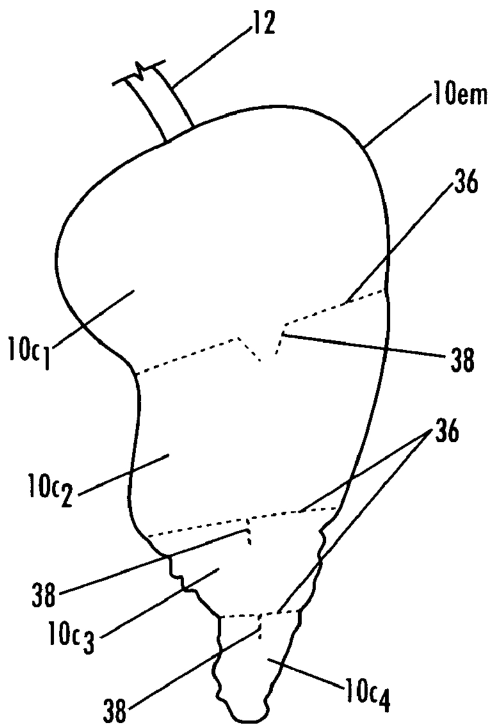
FIGS. 6A-6C illustrate a nested chamber configuration of a buoyancy member.
Figure 6B:
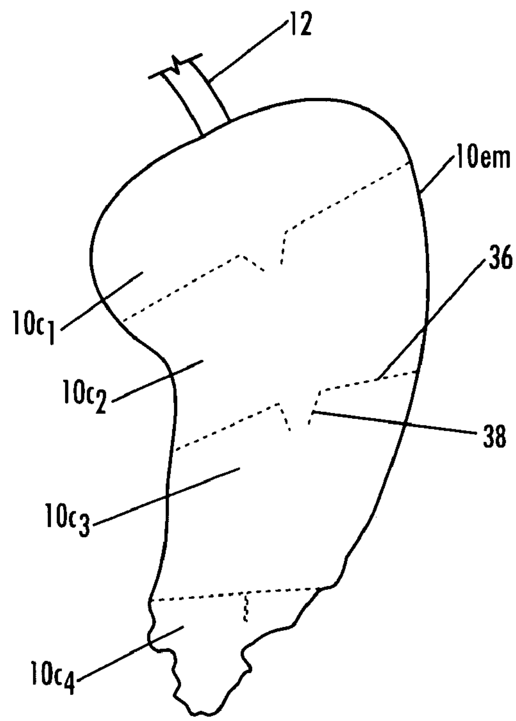
Figure 6C:
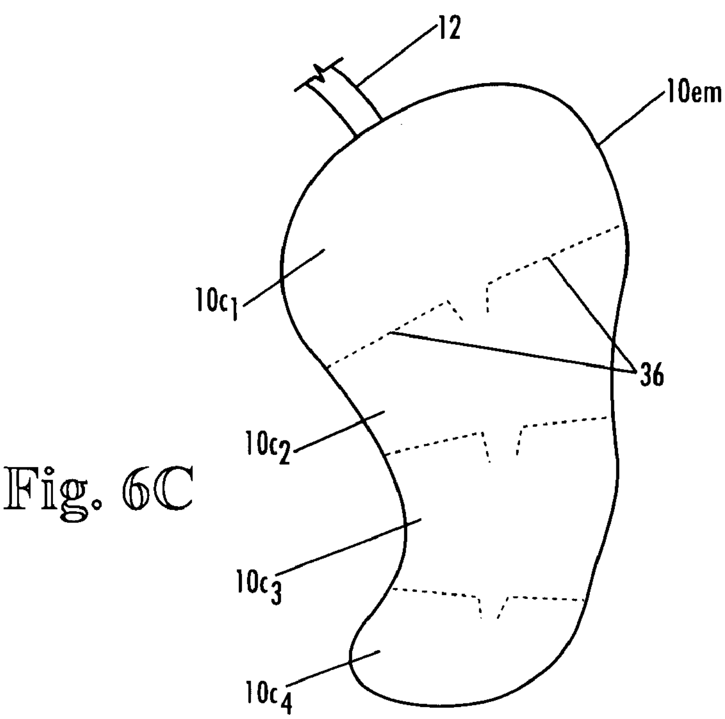

As shown in FIG. 5A, buoyancy member, although it may be variably expandable in volume in an expanded configuration, particularly when it is formed of a compliant material, is still somewhat predetermined as to its volume, within a given range, as it will typically be inflated to a predetermined pressure that has been calculated to not stretch the walls of the buoyancy member to a point where they are unacceptably porous to gas leakage. Optionally, a buoyancy member 10*bm* may be provided that is more adjustable in the volume that it can contain, giving the user the ability to adjust the buoyancy member over a larger range of volumes so as to adjust the overall buoyancy/density of device 10 in the expanded configuration. FIGS. 6A-6C illustrate one version of an adjustable volume buoyancy member 10*bm* that is provided with a "nested chamber" configuration, in which chambers 10*c*1-10*c*4 (although different numbers of chambers can be provided, which number may be two, three, or more than four) can be sequentially expanded, to vary the size of the buoyancy member 10*bm* and thus the volume of gas and amount of buoyancy added to the overall device 10 that buoyancy member forms a part of. Adjacent chambers can be separated by a baffle or membrane 36 that may be formed of the same material as the wall of buoyancy member 10*bm*, for example, with each baffle or membrane 36 containing at least one one-way valve 38 therein. Valves 38 are configured to open at progressively greater pressures, so that the chambers can be opened sequentially and only to the extent desired, based on the amount of pressure applied through conduit 12.

Figure 7:
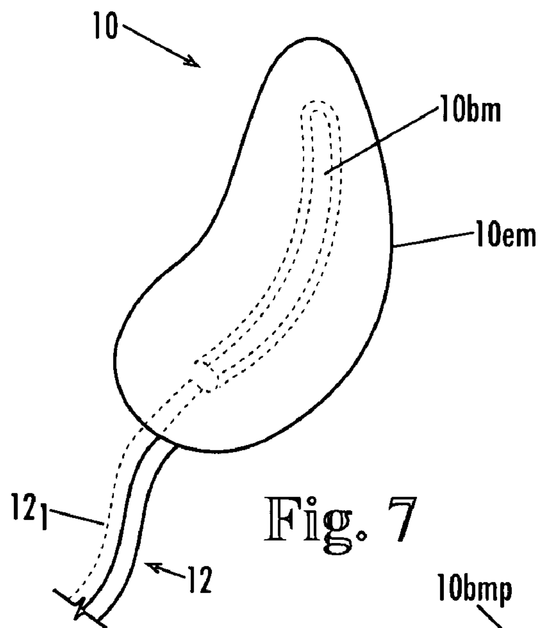
FIG. 7 illustrates an embodiment of a device that includes a buoyancy member within an expandable member, where the buoyancy member is formed in the shape of an elongated spine.

FIG. 7 illustrates an embodiment of device 10 that includes a buoyancy member 10*bm* within expandable member 10*em* where buoyancy member 10*bm* is formed in the shape of an elongated spine. In this particular embodiment, buoyancy member 10*bm* is an elongated tubular member having a curvature that generally corresponds to the curvature of expandable member 10*em* in the expanded configuration, to follow the contour thereof. Alternatively, buoyancy member 10*bm* could be formed as a straight tubular member. In either conformation, the length dimension of buoyancy member is such to extend over at least half the length of expandable member 10*em* or at least two thirds of the length of expandable member 10*em* or at least three quarters of the length of expandable member 10*em*. In either the straight or the curve conformation, the length of buoyancy member distributes the buoyancy more equally over the volume of the expanded expandable member, compared to a buoyancy member 10*bm* that is allowed to float to one particular location of an expandable member. The embodiment having a curvature that somewhat conforms to the curvature of the expanded expandable member 10*em* has been found to distribute the buoyant forces even better than a buoyancy member having a straight conformation. This distribution of the buoyancy forces helps to maintain the expanded expandable member 10*em* in the desired location, as well as orientation that it is implanted in, as it minimizes any torquing forces or other uneven forces that a less well distributed buoyancy member may place on the expanded expandable member. In this embodiment, like all other embodiments described herein, buoyancy member 10*bm* can be sized to provide an amount of buoyancy that, when combined with expandable member 10*em*, provides a substantially neutral buoyancy when implanted in the abdominal cavity of the patient. Neutral buoyancy refers to device 10 having a density about the same as the density of the surrounding environment in the abdominal cavity in which the device is implanted. Accordingly, device 10 will thus not tend to either sink or float in the abdominal cavity, but have a tendency to remain substantially in the location implanted.

Alternatively, this embodiment, or any other embodiment described herein, may be configured to have a slightly positive buoyancy. This slight (e.g., less than 0.2 pounds positive buoyancy when implanted, typically much less than 0.2 pounds but greater than zero pounds) buoyancy tends to right the device in a situation where the positive buoyancy is applied in a superior portion of the expandable member and the patient is in an upright sitting or standing position, for example. An alternative technique for adding buoyancy, such as to adjust a displaced device, or that can even be utilized at the original implantation of the device, is to input a small quantity of gas into the liquid filled expandable member 10*em*. This can be done at the time that the expandable member 10*em* is filled with liquid, or, for example, on a subsequent patient visit. When done subsequently, the physician may optionally withdraw a small amount of liquid to provide space to be occupied by the small gas volume.

Accordingly, depending on the relative volumes and densities of expandable member 10*em* and buoyancy member 10*bm*, device 10 can: 1) reduce the overall density to reduce the relative "weight" of the implant within the abdomen (i.e., a neutrally buoyant implant will neither sink nor float but maintain a relatively stable position relative to the surroundings in the abdominal cavity); 2) achieve neutral buoyancy within the abdomen; or 3) achieve a slightly positive buoyancy that helps orient the device 10 upwards into a desired position and orientation (e.g., located against the fundus and the diaphragm).

In one particular embodiment, the buoyancy member 10*bm* of FIG. 7 is an inflatable tube that can be inflated with gas to provide buoyancy. In one particular embodiment, buoyancy member is a silicone tube that is inflatable with about five to about twenty cc volume of gas. In one specific embodiment, buoyancy member 10*bm* was inflated with ten cc air. Buoyancy member 10*bm* may be left free floating within expandable member 10*em* or may be fixed to an inner wall of expandable member 10*em*. Further alternatively, buoyancy member 10*bm* may be co-molded with expandable member 10*em*. When buoyancy member 10*bm* is not allowed to free float, but is fixed in some manner relative to expandable member 10*em*, this may reduce the risk of failure due to wear that might possibly be caused by repetitive contact between buoyancy member 10*bm* and expandable member 10*em* when buoyancy member 10*bm* is allowed to free float. Buoyancy member 10*bm* may be pre-inflated prior to insertion through the body of the patient, or even prior to assembly within the expandable member. Alternatively, a conduit $\mathbf{12}_1$ (shown in phantom lines in FIG. 7) may be provided in fluid communication with buoyancy member 10*bm* so that buoyancy member can be inflated after device 10 is inserted into the patient, either before or after inflation of expandable member 10*em*.

Figure 8:
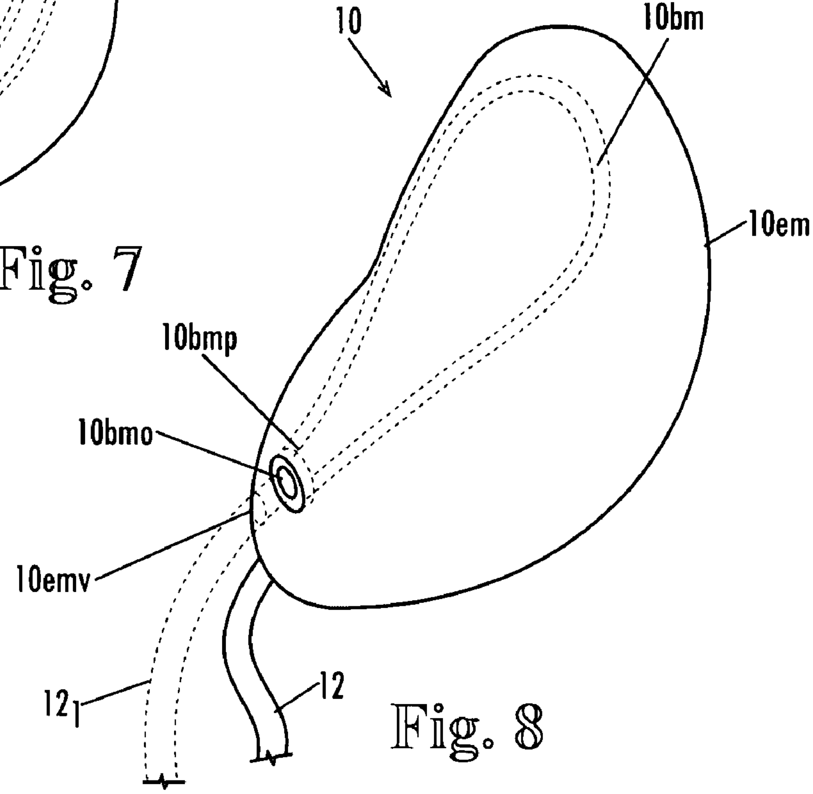
FIG. 8 illustrates an arrangement in which a self-expanding buoyancy member is provided within an expandable member of the device.

FIG. 8 illustrates an arrangement in which a self-expanding buoyancy member 10*bm* is provided within expandable member 10*em* of device 10. Self-expanding buoyancy member 10*bm* can be formed of silicone, or other biocompatible elastomer, for example, and can be molded in the expanded configuration shown in FIG. 8, with an open inferior end 10*bmo*. Since buoyancy member 10*bm* has an internal chamber or space, the buoyancy member can be compressed or flattened to a much reduced configuration, with a much smaller cross-sectional dimension to facilitate insertion though a small opening in the patient for percutaneous delivery. Buoyancy member 10*bm* has walls of sufficient thickness and elasticity that when compressive forces are withdrawn, buoyancy member 10*bm* automatically returns to the expanded configuration shown in FIG. 8 without the need to input pressurized gas or liquid into the chamber, as the walls elastically return to the expanded configuration that they were formed in. This elastic driving force also draws air (or any fluid medium that opening 10*bmo* is in fluid communication with at the time of the expansion of the walls) into the chamber of buoyancy member 10*bm*.

Accordingly, buoyancy member can be compressed to its compressed configuration and expandable member 10*em* can be compressed around buoyancy member 10*bm* where expandable member 10*em* is also in a compressed, non-expanded configuration, so that device 10 is reduced significantly in cross-sectional dimension for insertion into a patient. For example, device 10 in the compressed configuration may resemble a cylinder. After passing device 10 through a small opening in the patient and into the abdominal cavity (such as through a sheath, for example, or by manually inserting the device 10, while maintaining compression on the device as it is being stuffed through the small opening) conduit 12 that is in fluid communication with expandable member 10*em* has a proximal end portion that remains extending out of the patient. Also, a removable conduit $\mathbf{12}_1$ (shown in phantom lines in FIG. 8) is in fluid communication with, and seals off the opening 10*bmo* of buoyancy member 10*bm*. A proximal end portion of conduit $\mathbf{12}_1$ also remains outside of the patient when device 10 has been inserted into the abdominal cavity and placed in a desired location and orientation for implantation. However, the proximal end of conduit $\mathbf{12}_1$ need not be connected to a pressurized source of gas (although it can be), but can simply be open to the atmosphere (with or without a filter). Thus, when the compressive forces are removed from device 10, buoyancy member 10*bm* self-expands, thereby drawing gas through conduit $\mathbf{12}_1$ which fills the inner chamber of buoyancy member 10*bm*. Conduit $\mathbf{12}_1$ can then be detached from buoyancy member 10*bm* and withdrawn from expandable member 10*em* and from the body of the patient. A one-way valve 10*emv* is provided in the wall of expandable member 10*em* to seal off the opening through which conduit $\mathbf{12}_1$ is removed. Optionally, a one-way valve 10*bmv* may be provided in the open end of buoyancy member 10*bm* to prevent gas from migrating into expandable member 10*em*. Further optionally, the open end 10*bmo* and valve 10*emv* can be integrated at the wall of expandable member 10*em*. Buoyancy member 10*bm* may be free floating or fixed according to any of the techniques described above. In one particular embodiment, buoyancy member is bulb-shaped, like the shape of a bulb on a turkey baster, with the bulb portion oriented toward the superior end portion of expandable member 10*em*.

Figure 9:
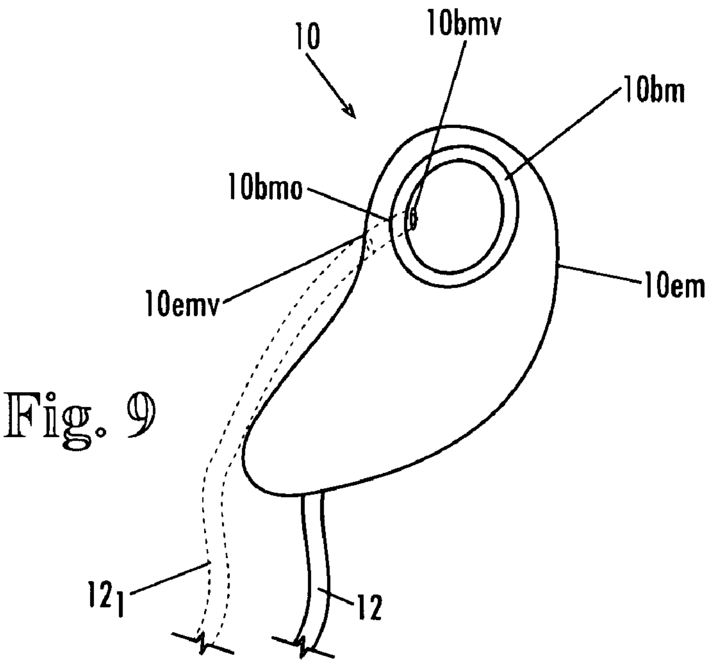
FIG. 9 illustrates another arrangement of a device including a self-expanding buoyancy member.
Figure 10:
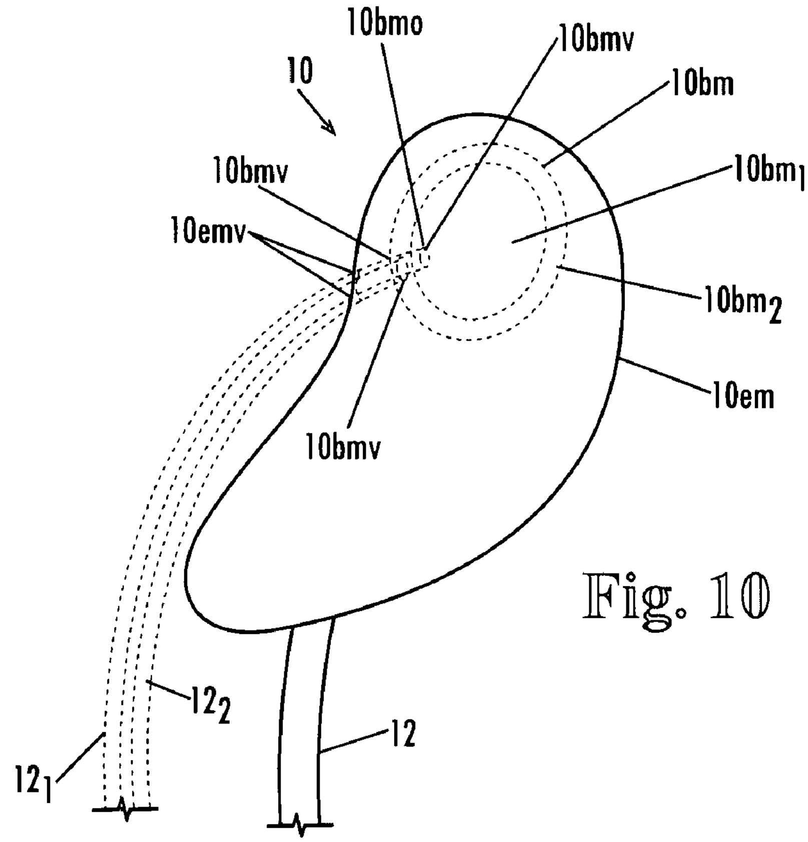
FIG. 10 shows a device having a buoyancy member that has inner and outer chambers.

FIG. 9 illustrates another arrangement of a device 10 including a self-expanding buoyancy member 10*bm*. In this example buoyancy member 10*bm* is a spherical member that operates in any of the same manners described above with regard to the embodiment of FIG. 8. The device 10 shown in FIG. 10 has a buoyancy member 10*bm* that has inner and outer chambers 10*bm*1 and 10*bm*2, respectively. After insertion of device 10 into the abdominal cavity, internal chamber 10*bm*1 can be allowed to self-expand or, alternatively, pressurized gas may be inputted to expand the inner chamber. In either case, gas is inputted through removable conduit $\mathbf{12}_1$. In either case, inner chamber 10*bm*1 is provided with a one-way valve 10*bmv* to close off opening 10*bmo* after removal of conduit $\mathbf{12}_1$ to prevent loss of gas to the external chamber 10*bm*2. Conduit $\mathbf{12}_2$ is used to deliver pressurized fluid (e.g., pressurized saline or the like) to external chamber 10*bm*2 and then conduit $\mathbf{12}_2$ can be removed. All openings in device 10 that conduits $\mathbf{12}_1$ and $\mathbf{12}_2$ pass through are closed off by one way valves 10*bmv*, 10*emv* when conduits $\mathbf{12}_1$, $\mathbf{12}_2$ are removed. Alternatively, the conduits and valves can be maintained so that the gas pressure within buoyancy member 10*bm* can be adjusted at a later time. The pressurized liquid in external chamber 10*bm*2 helps to maintain the gas within internal chamber 10*bm*1 and prevent it from migrating out into pressurized chamber 10*bm*2. This is achieved because the pressure within buoyancy member 10*bm*2 creates a "structural shell" around buoyancy member 10*bm*1. As this shell 10*bm*2 is pressurized and takes form, the gas is inputted through conduit $\mathbf{12}_1$ into the cavity (inner chamber) of buoyancy member 10*bm*1 so that there is not a vacuum in the inner chamber, thereby helping prevent shell 10*bm*2 from collapsing. Cooperatively, buoyancy member 10*bm*2, once pressurized, hold open the cavity/inner chamber of buoyancy member 10*bm*1. Depending on the material properties of buoyancy member 10*bm*2, gas may be able to permeate out of the cavity of buoyancy member 10*bm*1. However, because of the structure of buoyancy member 10*bm*2, the gas will not permeate out to an extent that would create a negative pressure, since energy would have to be expended to force the gas out and create a negative pressure. Expandable member 10*em* can be expanded by inputting pressurized liquid through conduit 12.

In general, for devices 10 described herein, the pressure within expandable member 10*em* will vary depending upon the material used to form the wall of the expandable member 10*em*, as well as the geometry of the expandable member 10*em*, and whether gas or liquid is used to inflate the expandable member 10*em*. For example, an expandable member 10*em* made of silicone that is inflated with saline typically has an internal pressure ranging from about 0.25 pounds per square inch (psi) to about 1.0 psi, depending upon the degree of inflation. Because saline is relatively incompressible, expandable member 10*em* will hold its volume under the pressures of the abdomen. Alternatively, if expandable member 10*em* is filled with a gas, the pressure may be increased to ensure that the abdominal pressures do not compress the shape of expandable member 10*em*, thereby deforming it. The means pressures in the abdomen typically range between about 0 psi to about 0.4 psi. If a person is jumping or coughing, abdominal pressures may spike as high as about 4.0 psi. The buoyancy member 10*bm* needs to be designed to that its shape can withstand the sum of the pressure of expandable member 10*em* and the at least the mean abdominal pressure (or, preferably, peak abdominal pressure). This can be achieved by designing buoyancy member 10*bm* to have sufficient structural strength to withstand the sum of these pressures. One approach in such design is to provide buoyancy member 10*bm* with a hard plastic shell that is structurally strong enough to withstand about 5 psi compression forces. Another approach is to design buoyancy member 10*bm* as flexible membrane that self expands via a compressible foam. In this case, the foam, upon expanding the flexible membrane of buoyancy member 10*bm*, draws air into a chamber defined by the flexible membrane as the foam expands into it. In this type of design, the structure of buoyancy member 10*bm* needs to withstand the means pressures (e.g., about 2 psi) and, during pressure spikes, buoyancy member 10*bm* may deform and rebound after expiration of the spike, due to the elastic properties of the foam. Further alternatively, buoyancy member 10*bm* may be inflated with a gas. In this arrangement, the gas within buoyancy member 10*bm* needs to be able to maintain a pressure to withstand the peak sums of pressures within expandable member 10*em* and the abdomen, for example, about 5 psi.

Figure 11A:
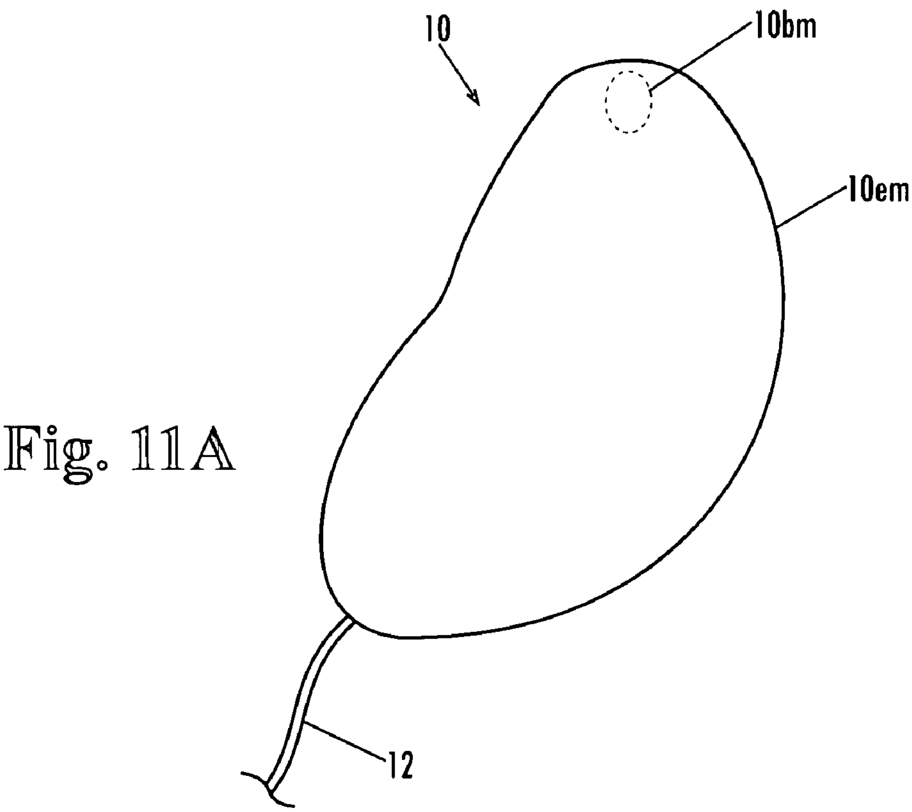
FIGS. 11A-11B illustrate devices that include a substantially rigid buoyancy member.
Figure 11B:
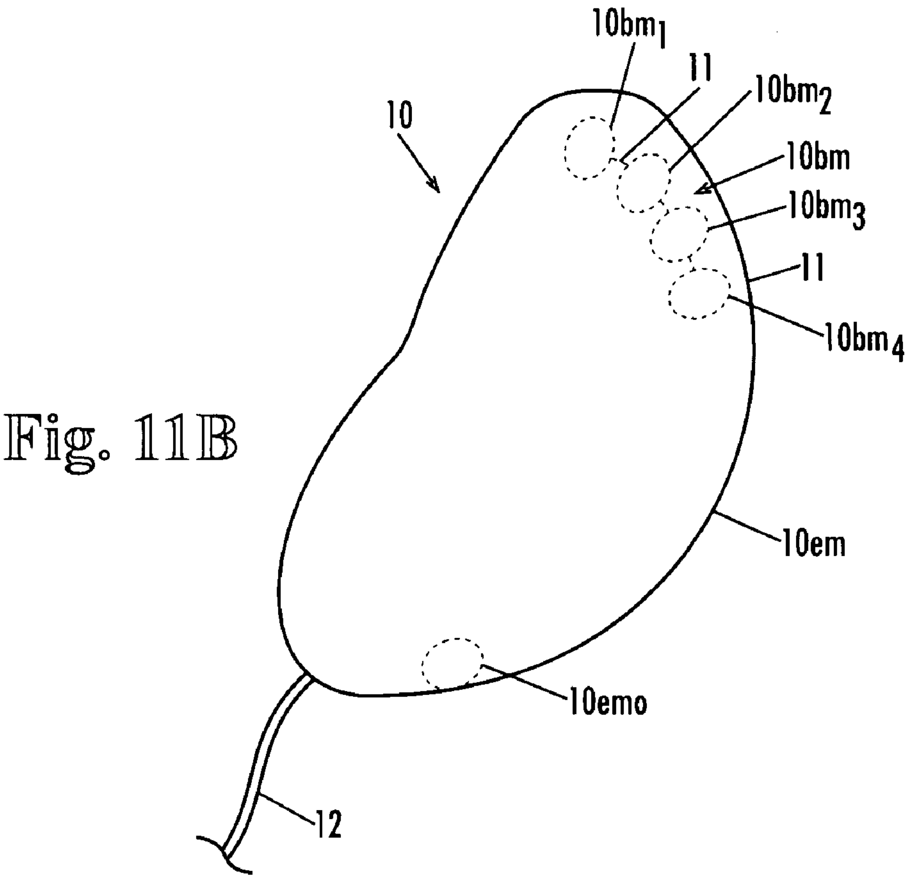

FIGS. 11A-11B illustrate devices 10 that include a substantially rigid buoyancy member 10*bm*. For example, in FIG. 11A, buoyancy member 10*bm* is a hollow, substantially rigid sphere, somewhat like a ping pong ball. As long as the outside diameter of buoyancy member 10*bm* is less than or possibly slightly greater than (since tissue is stretchable) a cross sectional dimension of an opening in the patient that device 10 is delivered through, then the buoyancy member does not need to be compressible. For example, the outside diameter of buoyancy member may be less than about 50 mm. For example, buoyancy member 10*bm* may be made from polyethylene, or other relatively low density, biocompatible polymer or even thin-walled biocompatible metal. Buoyancy member 10*bm* may be free floating within expandable member 10*em* or fixed to an inner wall surface of expandable member 10*em* according to any of the techniques described above. To increase the buoyancy effect, additional balls or other substantially rigid buoyancy structures may be added, since the overall size of the single buoyancy member 10*bm* cannot be substantially increased in this case, for reasons noted above. FIG. 11B shows a device 10 that includes a buoyancy member 10*bm* having four substantially rigid buoyancy members 10*bm*1-10*bm*4, which are spherical in this case, although different shapes may be used, as noted. The buoyancy members 10*bm*1-10*bm*4 are linked in the example shown in FIG. 11B by linking members 11, which may be polymeric or metallic strands, wires or threads, for example. The chain thus forming the buoyancy member 10*bm* may be free floating as a chain, or fixed relative to the expandable member 10*em* in any of the ways described previously. Alternatively, buoyancy members 10*bm*1-10*bm*4 may be left separate from one another and may be free floating, or these separate members may be individually fixed relative to expandable member 10*em* according to any of the previously described techniques.

It is further noted that none of the alternative arrangements described with regard to FIGS. 11A-11B are limited to either use of either one or four buoyancy members 10*bm*, as two, three or any number greater than four can be used to vary the relative buoyancy, up to a maximum number that would substantially completely fill expandable member 10*em* in the expanded configuration. Even with the completely filled arrangement, liquid can still be inputted into expandable member 10*em* to fill the interstices between buoyancy members 10*bm*1-10*bm*N (where N equals the total number of buoyancy members used). In cases where the number of buoyancy members 10*bm* used is greater than a maximum number that can be aligned in a single row so that expandable member 10*em* can be compressed therearound to form a substantially cylindrical shape for delivery through a percutaneous opening, the additional number of the buoyancy members 10*bm* over and above that maximum number (or alternatively, all buoyancy members 10*bm*) may need to be loaded into expandable member after inserting the expandable member (with or without a portion of the buoyancy members already loaded therein) into the abdominal cavity. In such case, expandable member 10*em* can be provided with a valve or otherwise closable opening 10*emo* having a sufficient diameter to allow buoyancy members 10*bm* to be inserted therethrough. After inserting buoyancy members through the incision in the patient (which may include insertion through a sheath or cannula) and into expandable member 10*em*, expandable member can be sealed to provide a liquid impermeable chamber.

Figure 11C:
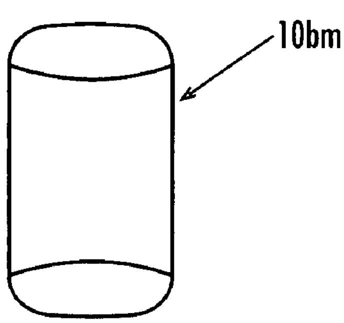
FIG. 11C shows a buoyancy member having a substantially cylindrical shape.
Figure 11D:
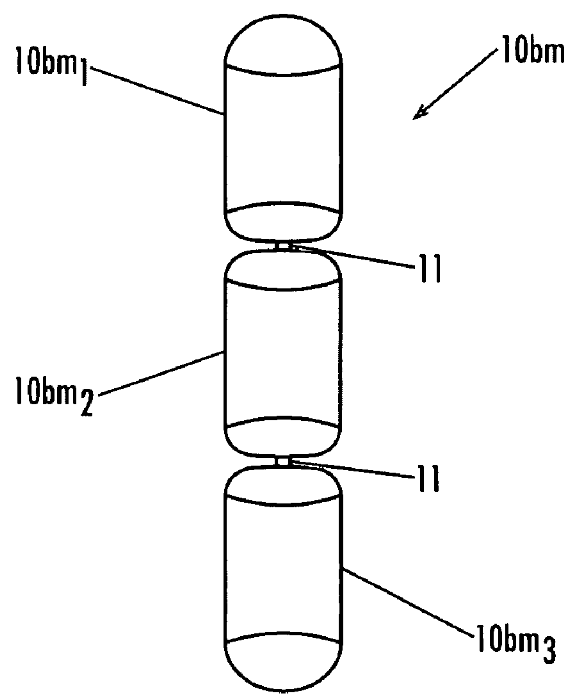
FIG. 11D illustrates a plurality of the shapes shown in FIG. 11C, joined by links to form a buoyancy member.

It is further noted that the shape of buoyancy member 10*bm* shown in FIG. 11A does not have to be spherical, but can be any other shape that includes a sealed off, gas-containing chamber therein and which has a maximum cross-sectional dimension that does not exceed a predetermined maximum dimension (examples of which were described above) that would prevent it from being inserted (with device 10 compressed therearound) through a small opening in a patient for delivery into the abdominal cavity. FIG. 11C shows one alternative shape in which buoyancy member has a substantially cylindrical shape, with a central cavity that seals gas therein. FIG. 11D illustrates a plurality of the shapes shown in FIG. 11C (i.e., 10*bm*1, 10*bm*2 and 10*bm*3) joined by links 11 to form buoyancy member 10*bm*. Alternatively, these buoyancy members do not have to be shells, but can be solid and made of a material with very low density, e.g., a foam, sponge or rigid plastic with many air pockets. Substantially rigid plastics can be altered to lower their densities by infusing them with air bubbles or pockets during their manufacture. Another technology uses micro-hollow glass spheres to reduce the density of a plastic when infused therein during manufacture. Another alternative provides a large number of small plastic hollow spheres encapsulated within a larger shape. For example, a thin walled silicone member can contain a larger number of small polyethylene hollow spheres, to provide a buoyancy member 10*bm* having an overall shape of the silicone member, with the buoyancy member 10*bm* having a density substantially less than that of saline.

Figure 12A:
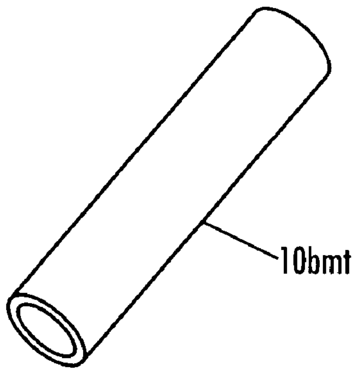
FIGS. 12A-12B illustrate another example of a buoyancy member.
Figure 12B:
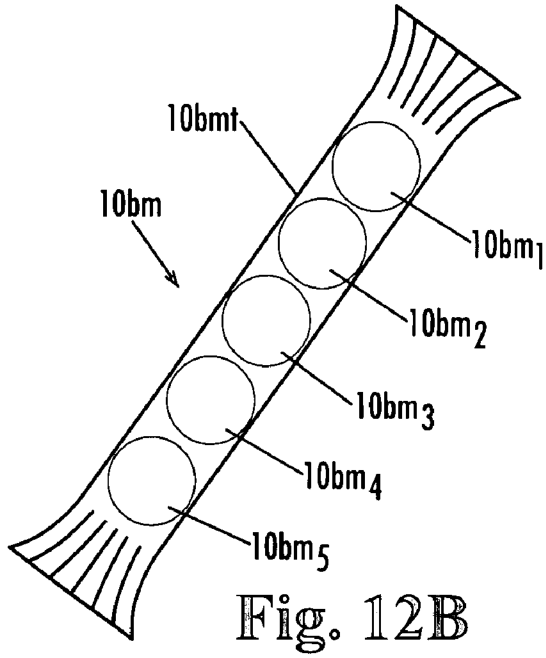

FIGS. 12A-12B illustrate another example of a buoyancy member 10*bm*. In this embodiment, a tubular member 10*bmt* is provided that has an annulus therethrough of inside diameter that permits substantially rigid buoyancy members 10*bm*1, 10*bm*2, . . . , 10*bm*N (where N=the total number of buoyancy members) to be loaded therein. For example, tubular member 10*bmt* may be flexible, and may even be expansible so as to stretch somewhat as it is deformed by buoyancy members 10*bm* being inserted therein, when buoyancy members have a slightly greater cross-sectional dimension that the inside diameter of the annulus of tubular member 10*bmt*. Alternatively, buoyancy members may be freely slidable into the annulus without deformation of tubular member 10*bmt*, and in this case, tubular member can be flexible or rigid. In one particular embodiment, tubular member is formed from silicone, either from a sheet, or extruded in the tubular shape. In another particular embodiment, tubular member includes layers of EVOH, low density polyethylene, and polyurethane to provide an even better gas impermeable barrier. Buoyancy members 10_bm_1, etc. can be formed the same as described above with regard to FIGS. 11A-11B.

Once the total number of buoyancy members desired have been loaded into tubular member 10_bmt_, the ends of tubular member 10_bmt_ are sealed off, as illustrated in the completed buoyancy member 10_bm_ shown in FIG. 12B. The spaces in the annulus between the buoyancy members 10_bm_1, . . . , 10_bm_N can also hold gas and add to the buoyancy forces generated by buoyancy member 10_bm_. The buoyancy member 10_bm_ shown in FIG. 12B can be manufactured into expandable member 10_em_, or can be inserted through an opening such as opening 10_emo_, either before or after insertion of expandable member 10_em_ through an opening in a patient and into the abdominal cavity. Buoyancy member 10_bm_ may be left free floating in the fluid used to expand expandable member 10_em_ or may be fixed to expandable member 10_em_ according to any of the techniques described previously. When tubular member 10_bmt_ is flexible, it can be bent to follow the contour of an inside wall surface of expandable member 10_em_ in the expanded configuration, and fixed to the inside wall surface in that bent configuration.

Figure 13:
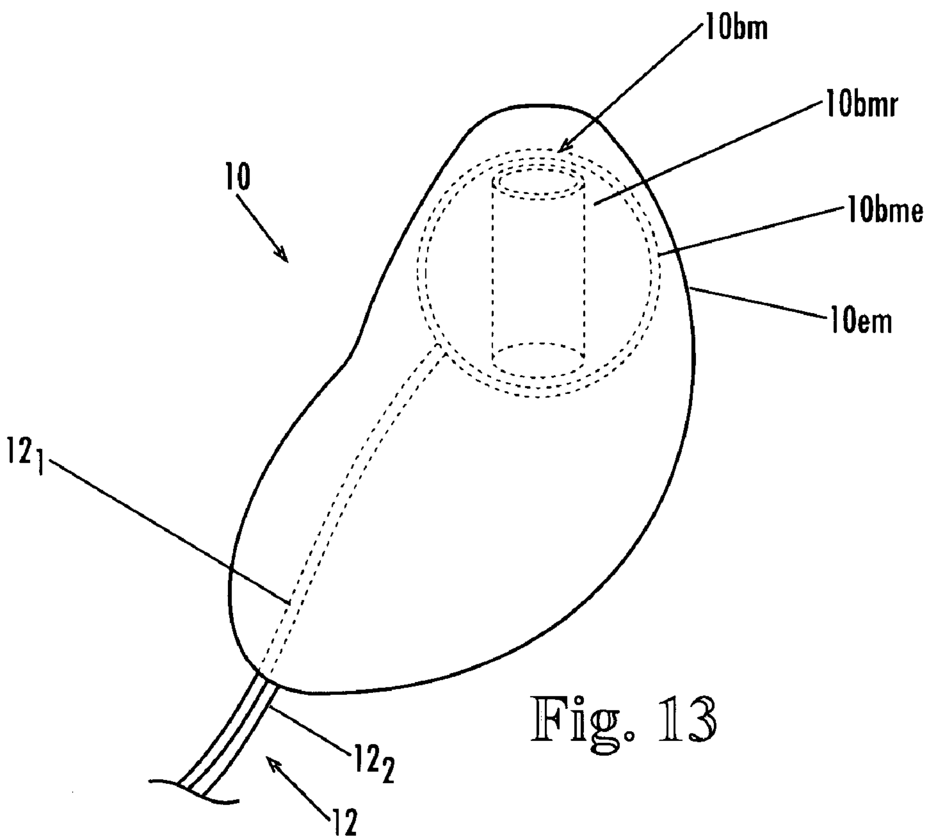
FIG. 13 illustrates another arrangement of a buoyancy member within an expandable member of a device.

FIG. 13 illustrates another arrangement of a buoyancy member 10_bm_ within an expandable member 10_em_ of device 10. In this arrangement buoyancy member 10_bm_ includes a substantially rigid portion 10_bmr_ and an expandable portion 10_bme_. Substantially rigid portion 10_bmr_ should not have any cross-sectional dimension that is substantially greater than a corresponding cross-sectional dimension of a small opening (such as a small incision, percutaneous opening, or port, for example) that device 10 is to be delivered through during placement into the abdominal cavity. As noted, such dimension may be slightly greater, since the skin and tissues of the patient can be stretched somewhat. In the example shown in FIG. 13, substantially rigid portion is tubular in shape with open ends and may have an outside diameter of one of the specifications noted above with regard to FIGS. 11A-11B. Alternatively, the substantially rigid portion can have an outside diameter that, when in inserted in a compacted device 10, allows it to be inserted through an incision no greater than about seven cm, or no greater than about five cm. For example, substantially rigid portion may have a diameter no greater than about 2.00", or no greater than about 1.85", or no greater than about 1.5". In this way, expandable portion 10_bme_ and expandable member 10_em_ can be compressed down around the substantially rigid portion 10_bmr_ for delivery through a small opening in a patient. Alternatively, the portion 10_bmr_ can be semi-compressible such that it can also be compacted during insertion. However, it can still have enough structural properties to spring open on its own and thereby provide supportive structure to open the surrounding portion 10_bme_. This compressibility of portion 10_bmr_ allows it to be designed larger that the embodiment employing a rigid portion 10_bmr_, or, alternatively, allows a smaller incision in the patient required to insert the buoyancy member 10_bm_/device 10.

Upon placement of device 10 in a desired location in the abdominal cavity, expandable portion 10_bme_ can be expanded with a pressurized gas source via conduit $\mathbf{12}_1$. Alternatively, the conduit can simply allow air into expandable portion 10_bme_ as portion 10_bmr_ springs open and expands portion 10_bme_, such that a source of pressurized gas would not be required to inflate the buoyancy member 10_bm_ in this embodiment. It is noted that conduit $\mathbf{12}_1$ can be a permanently placed conduit or it may be configured to be removable after inflating expandable portion 10_bme_, wherein it (and expandable portion 10_bme_ as well as expandable member 10_em_) can be configured in any of the manners described in previous embodiments having removable conduits. Expandable member 10_em_ can be inflated with liquid, such as saline or the like, via conduit $\mathbf{12}_2$.

This arrangement should not require periodic refills of gas into buoyancy member 10_bm_ or should at least reduce the frequency with which gas refills are necessary, since substantially rigid portion 10_bmr_ maintains the volume of its shape, thereby maintaining at least a predetermined minimum volume of gas within the buoyancy member 10_bm_. Accordingly, even if there is some gas leakage out of expandable portion 10_bme_, expandable portion 10_bme_ will never shrink down to a size less than the volume occupied by substantially rigid portion 10_bmr_, since substantially rigid portion 10_bmr_ is sufficiently rigid to withstand deformation forces that can be provided thereagainst by expandable portion 10_bme_ and/or the liquid pressure of the liquid within expandable member 10_em_. Buoyancy member 10_bm_ may be free-floating, as illustrated, or may be fixed at one or more locations to expandable member 10_em_ according to any of the techniques described previously. Also, the shapes of expandable portion 10_bme_ and substantially rigid portion 10_bmr_ are not limited to those shown, but may vary. As one non-limiting example, expandable portion 10_bme_ may be substantially cylindrical to follow the contours of a tubular substantially rigid portion 10_bmr_.

Figure 14:
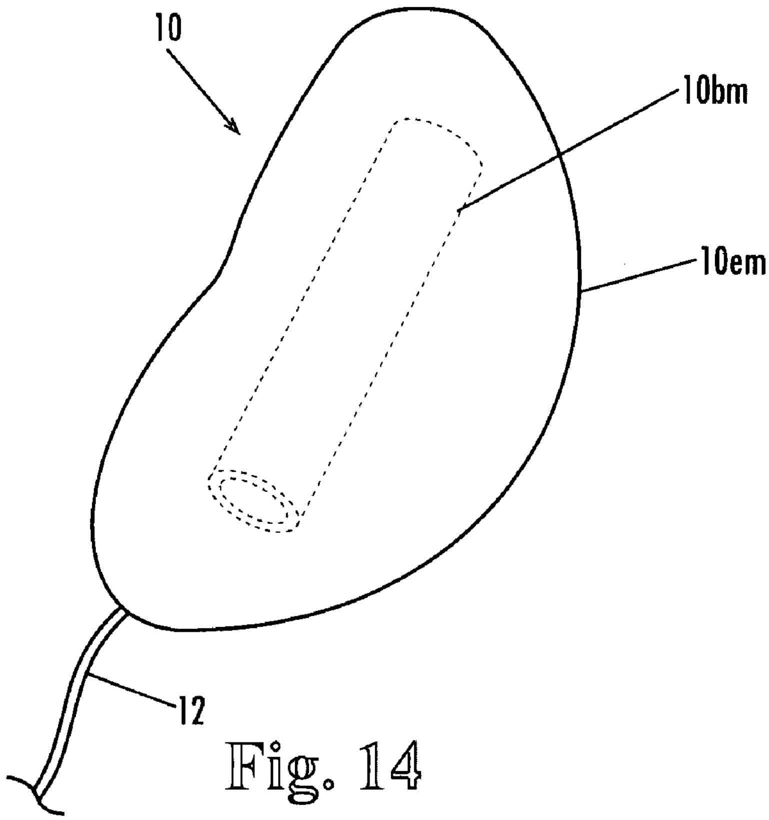
FIG. 14 illustrates another arrangement of a buoyancy member within an expandable member of a device.

FIG. 14 illustrates another arrangement of a buoyancy member 10_bm_ within an expandable member 10_em_ of device 10. In this embodiment, buoyancy member 10_bm_ is made of foam or other structural arrangement that encapsulates small gas pockets and therefore does not have to be inflated after placement of device 10 in the abdominal cavity. Although shown as a flexible cylindrical structure, buoyancy member 10_bm_ can be any other shape that lends itself to being inserted through a small opening in a patient when expandable member 10_em_ is compressed around it. A tubular or cylindrical shape particularly well lends itself to this task, as the device 10 takes on a somewhat cylindrical shape in the compressed state where a distal end portion can first be inserted through the opening of the patient with the rest of the cylindrical body being pushed through in a direction along the longitudinal axis of the cylindrical shape. Additionally, a tubular shape allows a central annulus to be closed off to capture and maintain air in the chamber formed by closing the tube off at both ends.

The foam used to make buoyancy member may be a silicone foam, or made from polyethylene or other biocompatible polymer for example. In each case, the foam is a closed-cell foam having a skin, so that the cells of the foam are closed and encapsulate air or other biocompatible gas therein, to ensure that the buoyancy properties of the foam are maintained and the buoyancy member 10_bm_ can therefore hold open a volume of gas and displace the liquid in expandable member 10_em_. It should be noted that some manufacturers denote a "sponge" as a closed-cell material, and other denote a closed-cell material as a "foam". Alternatively, an open-cell material may be used, when a layer of encapsulation is established around this open-cell sponge or foam. The encapsulation layer may be dip-molded onto the open-cell structure, or can be manufactured separately and then assembled around the open-cell structure. Such a configuration utilizes the open-cell foam or sponge to provide structural support to hold open the encapsulation layer. The encapsulation layer provides a barrier between the gas contained within the open-cell foam/sponge and the saline or other liquid contained in the expandable member 10_em_ outside of the buoyancy member 10_bm_. An encapsulation layer may be provided over a closed-cell foam/sponge using any of the same techniques described above. Various different structural arrangements and shapes of foam as well as sponge-like structural arrangements that can be used to make buoyancy member 10*bm* are discussed in more detail below. Buoyancy member 10*bm* may be free-floating, as illustrated in FIG. 14, or may be fixed to expandable member 10*em* at one or more locations according to any of the techniques described with regard to previous embodiments above. Buoyancy member 10*bm* has a maximum outside dimension (e.g., outside diameter, or other cross-sectional dimension) that permits it, together with device compressed down around it, to be inserted through a small incision in a patient. Examples of such maximum outside dimension are those described above with regard to the maximum outside diameter of rigid portion 10*bmr* in FIG. 13.

In one particular embodiment, the foam is a silicone foam made from silicone typically made to make a silicone sheet, but with a foaming agent (sodium bicarbonate, about 1% to about 5% by weight, typically about 5%) mixed with the silicone to make a slurry. This slurry can be described as having a consistency like peanut butter and the slurry is packed into a mold and then heated at about 150° C. for about an eighty minute cycle. The foaming agent, during the heat cycle, converts to water vapor, carbon dioxide and ammonia, thereby ensuring the biocompatibility of the resulting foam product. The mold is then removed from the heat and allowed to cool. After cooling, the foam product is removed from the mold and finished by removing any flash that may have formed. The finished product is a closed-cell foam that includes a skin layer both inside and outside. In another embodiment, the foam is polyethylene, which is expanded via high pressure carbon dioxide. The infusion of the carbon dioxide creates air pockets that form the foam, leaving a material that remains polyethylene which is therefore biocompatible.

Figure 15:
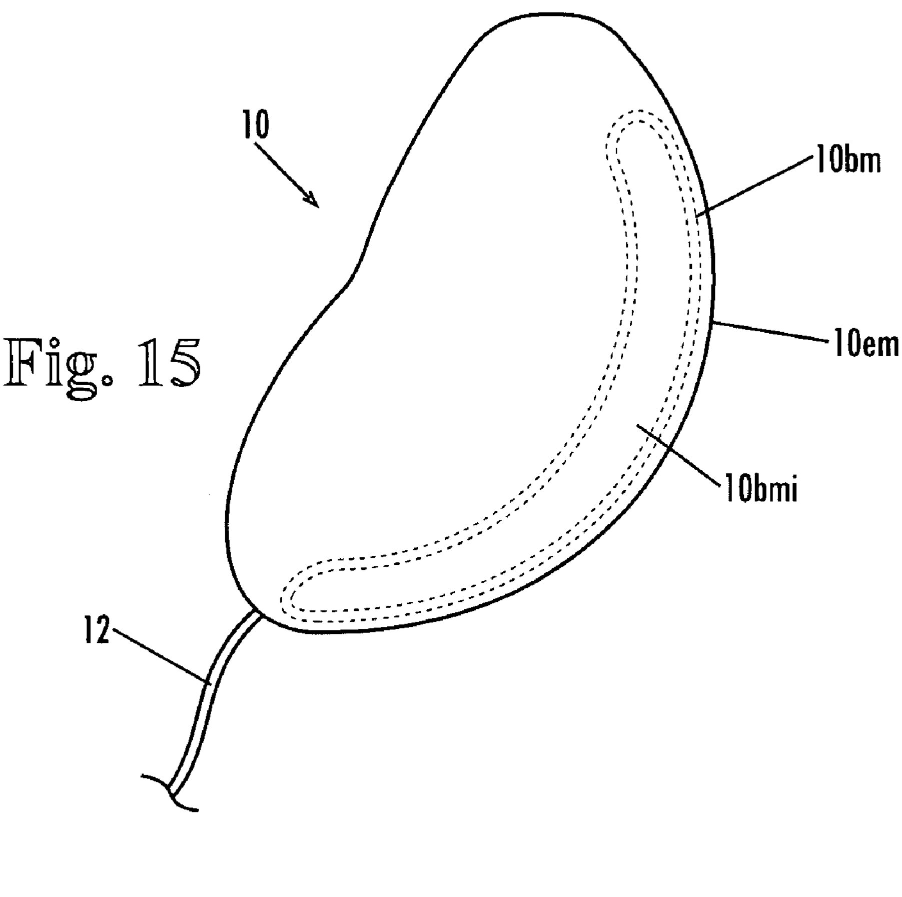
FIG. 15 illustrates a device wherein a buoyancy member forms an internal spine in an expandable member.

FIG. 15 illustrates a device 10 wherein buoyancy member 10*bm* forms an internal spine in expandable member 10*em* and distributes the buoyancy forces by being shaped proportionally to the expanded shape of expandable member 10*em*. For example, in FIG. 15, expandable member is substantially eggplant shaped when in the expanded configuration shown. Likewise, buoyancy member 10*bm* is also substantially eggplant-shaped, and is fixed to expandable member 10*em* to generally follow the contours of the expandable member 10*em* in the expanded configuration. This arrangement substantially distributes the buoyancy forces in a weighted distribution pattern that matches the weight distribution of the liquid in the expandable member 10*em* when it is expanded. Accordingly, the buoyancy forces are distributed as stably as possible, to minimize any torquing or other uneven forces that buoyancy member 10*bm* might otherwise apply to device 10 when implanted.

Buoyancy member 10*bm* is typically fixed to expandable member 10*em* along the entire length of buoyancy member 10*bm*. In the example shown, buoyancy member 10*bm* is fixed to an internal surface of expandable member 10*em*. Buoyancy member 10*bm* may be made of any of the foams described above with regard to FIG. 14, and may have a central space 10*bmi* that runs along the length thereof such that, when joined to expandable member 10*em*, the inner wall surface of expandable member 10*em* and the walls of buoyancy member 10*bm* seal off the internal space to maintain a gas-filled chamber therein. Buoyancy member 10*bm* has a maximum outside dimension (e.g., outside diameter, or other cross-sectional dimension) that permits it, together with device compressed down around it, to be inserted through a small incision in a patient. Examples of such maximum outside dimension are those described above with regard to the maximum outside diameter of rigid portion 10*bmr* in FIG. 13.

Alternatively, the foam shape of buoyancy member 10*bm* may be compressed such that substantially all of the air inside cavity 10*bmi* is expelled. The compressed buoyancy member 10*bm* then allows the entire device 10 to be compressed down further, overall. This allows for either a larger outside diameter (expanded) buoyancy member 10*bm* to be used, or a smaller incision length. After insertion of device 10 into the abdominal cavity, the foam can then be allowed to spring open by allowing air or pressurized gas to flow into chamber 10*bmi*, for example, via a conduit 12. The conduit 12 may have a one-way entry and may be removable, in a manner as described previously.

Figure 16A:
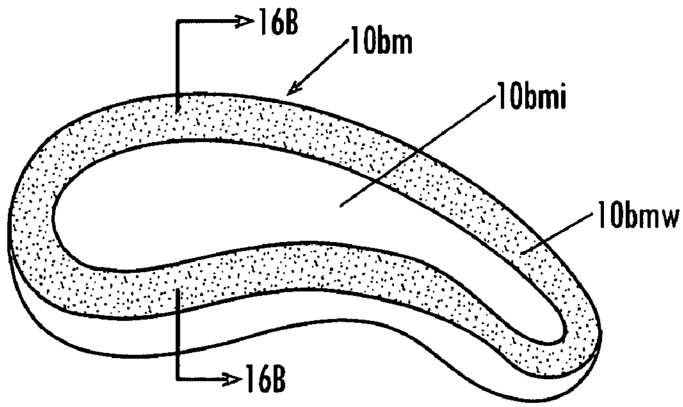
FIG. 16A illustrates an embodiment of a buoyancy member that is made of foam.
Figure 16B:
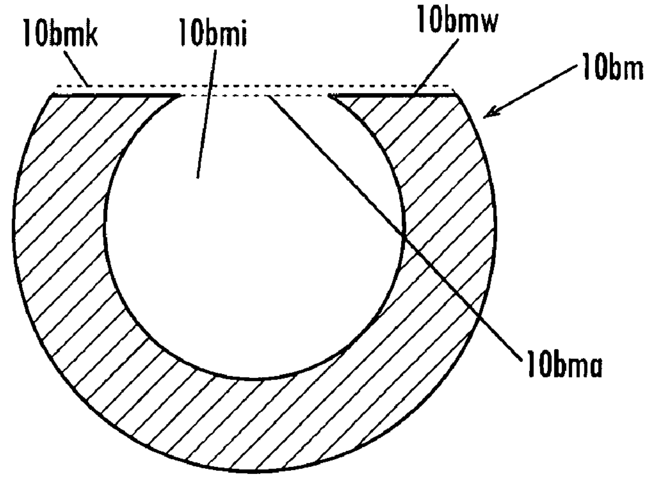
FIG. 16B is a cross-sectional view of the buoyancy member of FIG. 16A taken along line 16B-16B.

FIG. 16A illustrates an embodiment of a buoyancy member 10*bm* that is made of foam can be joined to expandable member 10*em* as an internal spine member in a manner as described above with regard to FIG. 15. Since the foam is less dense than the material making up the wall of expandable member 10*em*, its walls can be made substantially thicker than the expandable member 10*em* wall, thereby providing some structural rigidity as an internal spine, and, at the same time, encapsulating more gas to improve the buoyancy function. Buoyancy member 10*bm* can be formed with a hollow core that is open, when molded, and will be closed when buoyancy member 10*bm* is fixed to expandable member 10*em* to seal the space 10*bmi*. Accordingly, the surfaces or edges of the wall 10*bmw* around opening 10*bmi* are substantially smooth and conforming to the surface of expandable member 10*em* where they are to be joined. Buoyancy member 10*bm* has a maximum outside dimension (e.g., outside diameter, or other cross-sectional dimension) that permits it, together with device compressed down around it, to be inserted through a small incision in a patient. Examples of such maximum outside dimension are those described above with regard to the maximum outside diameter of rigid portion 10*bmr* in FIG. 13, although larger maximum outside dimensions may be alternatively used in embodiments where buoyancy member 10*bm* is compressed for the insertion, as noted above. FIG. 16B is a cross-sectional view of the buoyancy member 10*bm* of FIG. 16A taken along line 16B-16B.

Figure 16C:
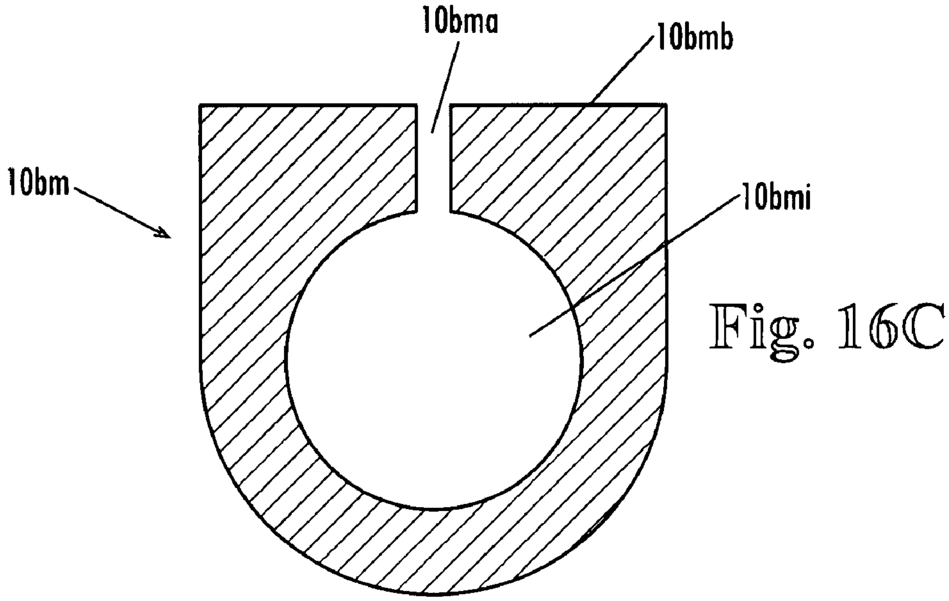
FIG. 16C is a cross-sectional illustration of an alternative embodiment of a foam buoyancy member.
Figure 16D:
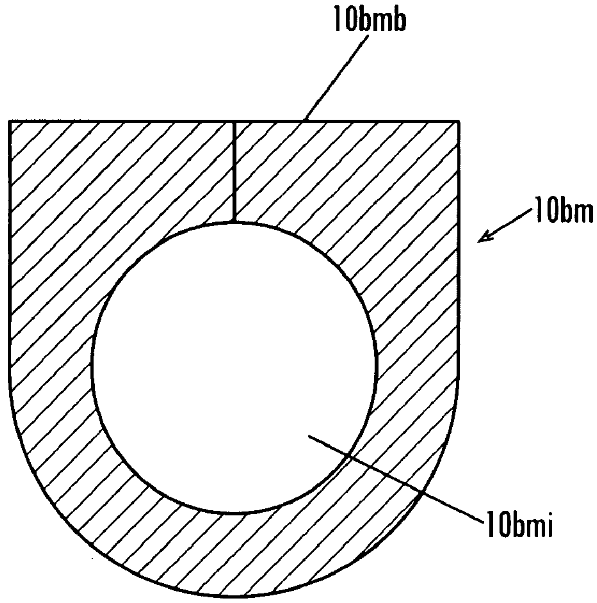
FIG. 16D is a cross-sectional illustration of the buoyancy member of FIG. 16C, after closing the internal chamber.
Figure 16E:
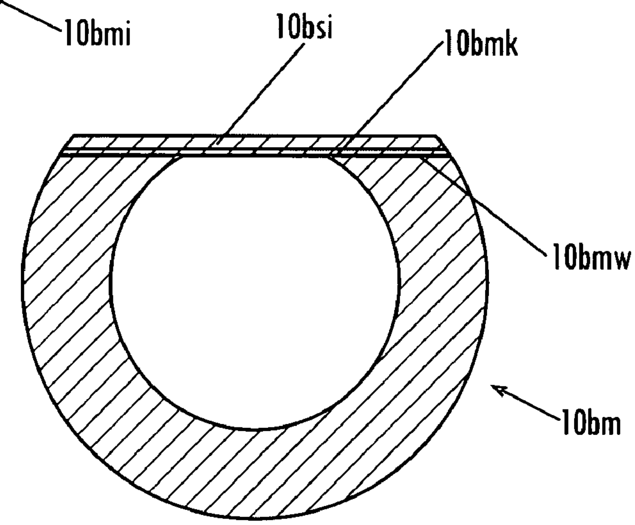
FIG. 16E is a cross-sectional illustration of the buoyancy member of FIG. 16*b*, after closing the internal chamber.
Figure 17:
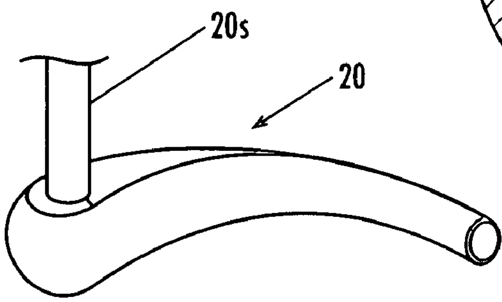
FIG. 17 illustrates a mandrel that is shaped to conform to the opening in the buoyancy member shown in FIG. 16A.

FIG. 17 illustrates a mandrel 20 that is shaped to conform to the opening 10*bmi* in buoyancy member 10*bm*. Accordingly, after molding the buoyancy member 10*bm* in the form shown in FIG. 16, buoyancy member 10*bm* can then be stretched over mandrel 20 where is temporarily fixed thereon. A shaft 20*s* can be controlled to dip the buoyancy member (on mandrel 20) into a vat of polymer to form a sealing layer or skin over the external surface of buoyancy member 10*bm* to further reduce the gas permeability thereof. Multiple dips may be performed to form multiple coats of this skin layer if desired. For example, a vat of silicone may be provided to dip-mold a layer of silicone over buoyancy member 10*bm*. A typical thickness of the layer coated by dip-molding is about 0.005" to about 0.030". By completely submerging mandrel 20 and buoyancy member 10*bm* in the molten polymer in the vat, a skin layer 10*bmk* (shown in phantom in FIG. 16B) can even be formed over the mandrel portion that fills the opening 10*bmi*. Upon completion of the coating and curing of the coating layer, this skin layer can be slit to remove the mandrel 20 and the skin layer 10*bmk* can then be closed back over by patching with a layer of silicone plus room temperature vulcanizing silicone adhesive for example. Alternatively, a thin sheet of silicone can be bonded over the opening in the foam product, using room temperature vulcanizing silicone adhesive for example. This could optionally be further dipped in silicone to even further ensure sealing. Further alternatively, this portion of buoyancy member 10*bm* can be left open as it will be closed off by sealing buoyancy member against an inner wall surface of expandable member 10*em*.

Alternatively, a sealing layer or skin can be molded over the foam buoyancy member by liquid injection molding (LIM). Using this approach, after the foam molded product is removed from its mold, it is inserted into a second mold that is slightly larger than the mold used to mold the foam product, but the same overall shape. Liquid silicone is then injected into the second mold in the space that surrounds the mold to thereby mod a skin layer between the foam product and the walls of the second mold. This process may be advantageous in that it can provide greater control over the consistency of the thickness of the skin layer over the foam product, and a single molding step may be performed, rather than repeated dipping steps.

Alternatively, an encapsulation layer may be fabricated separately, for example, by LIM or dip-molding. This layer can be assembled around the foam shape, and sealed off to provide complete encapsulation.

Alternatively, the gap 10*bma* between the walls 10*bmw* leading to opening 10*bmi* can be greatly reduced by molding in a shape illustrated in the cross-sectional view of FIG. 16C, to provided a broad flat surface 10*bmb* to increase the surface area to be adhered to the inner surface of a wall of expandable member 10*em*. Gap 10*bma* may be made small enough so that it can be closed by simply compressing the components of 10*bmb* together after placing RTV silicone adhesive therebetween. The gap can be about 0.01" to about 0.50", for example, or the gap can start completely closed, and then slit open to allow the internal mold to be released, and the slit can then be glued closed. In this case, the internal mold needs to be held in position during molding, and therefore there will likely be a portion of the internal mold that extends outwards and links to the outside mold. This link will result in a hold in the foam shape, therefore there may be more than a slit to close. For example, one or two patches may be required to form the complete closure. Alternatively, the process of bonding the foam buoyancy member to the expandable member 10*em* may provide an opportunity to close off the molded openings and the slit.

FIG. 16D illustrates the buoyancy member 10*bmb* having been closed by adhering gap 10*bma* closed. Alternatively, or in addition thereto, a thin sheet of silicone can be bonded over the backing surface 10*bmb*, using room temperature vulcanizing silicone adhesive for example. This could optionally be further dipped in silicone to even further ensure sealing. Further alternatively, the gap 10*bma* of buoyancy member 10*bm* can be left open as it will be closed off by sealing buoyancy member 10*bm* against an inner wall surface of expandable member 10*em*. FIG. 16E illustrates a sectional view of the buoyancy member of FIG. 16B in an embodiment where a thin layer of silicone 10*bsi* has been bonded over skin layer 10*bmk*, using room temperature vulcanizing silicone adhesive for example, thereby rigidifying buoyancy member 10*bm* to fortify its function as an internal spine member, and also providing additional sealing in of the gas cavity 10*bmi*. As noted above, this foam portion of the buoyancy member can alternatively be completely encapsulated in a separate encapsulating layer.

Figure 18A:
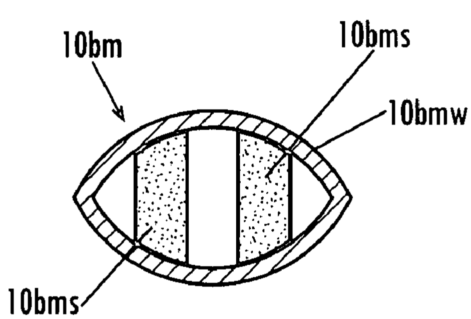
FIG. 18A-18K illustrate alternative configurations for forming structural type buoyancy members.

FIGS. 18A-18J illustrate alternative configurations for forming structural type buoyancy members, i.e., that do not need to be inflated or expanded in use, but retain a volume of gas therein to provide buoyancy forces when implanted as part of device 10. Any of these structures can be used to make the buoyancy members 10*bm* shown in FIGS. 14 and 15 for example. FIG. 18A is a construction that includes a tubular structure 10*bmw* which may be a polymer such as silicone, polyurethane EVOH, or other polymers described herein, as well as layers of one or more of these materials. Other examples include polypropylene and silicone structure, with silicone foam; or high density polyethylene or low density polyethylene with silicone. One or more foam struts 10*bms* (FIG. 18A shows two), are inserted in the open space formed by the tubular structure 10*bmw* to increase the overall structural rigidity and resistance to collapse of the tubular structure, while still maintaining some gas within the foam struts. It should be noted here that this construction does not have to be formed as a tube, or tubular eggplant shape, as the outer wall could be formed as a disk or other structure, for example. The previous statement applies to all of the embodiments in FIGS. 18A-18J.

Figure 18B:
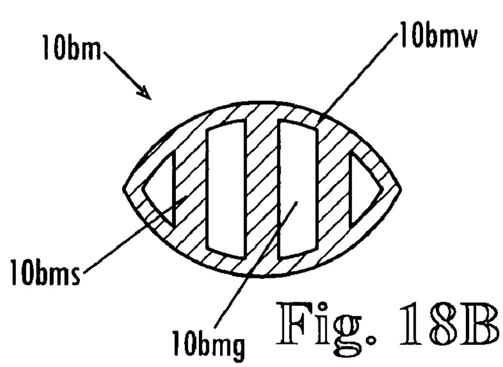

In FIG. 18B, buoyancy member 10*bm* is formed with a foam-like or sponge-like structural arrangement that encapsulates small gas pockets and therefore does not have to be inflated after placement of device 10 in the abdominal cavity. In this example, struts 10*bms* are formed integrally with wall 10*bmw* from the same material, which is not a foam, but one or more of the polymers already referred to. Struts 10*bms* are separated by pockets 10*bmg* in which gas is encapsulated, as the structure is completely closed off by walls 10*bmw*. Alternatively, the entire mass of FIG. 18B may be "normal" silicone (i.e., not foam) with a design that has a built-in structure so that it can be compressed, but then springs open and holds its shape open after being inserted into the abdominal cavity. The air cavity within this structure provides sufficient buoyancy to offset the additional density of the "normal" silicone, as compared to foam.

Figure 18C:
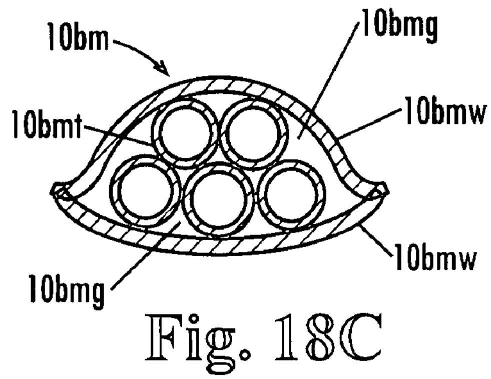

In FIG. 18C, the walls 10*bmw* of buoyancy member are supported by tubes 10*bmt* that may be made of foam, or alternatively may be made of polymer sheeting, which may be of the same formulation as wall 10*bmw*. In one particular embodiment, walls 10*bmw* are silicone and tubes 10*bmt* are formed of silicone. In another particular embodiment, walls 10*bmt* are formed of silicone and tubes 10*bmt* are formed of high density polyethylene or low density polyethylene. Still further tubes 10*bmt* may be made of silicone foam, polyethylene foam or silicone that is not foam ("normal" silicone). Tubes 10*bmt* provide structural support to buoyancy member to keep it from collapsing under pressure imposed by the liquid in expandable member 10*em*. At the same time, the annuli in tubes 10*bmt* encapsulate gas. Additionally, gas is encapsulated in the walls of the tubes 10*bmt* when they are formed of foam. Still further, gas is encapsulated in the gaps or interstices 10*bmg* between the tubes 10*bmt*.

Figure 18D:
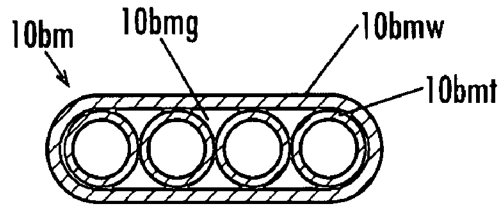

The embodiment of FIG. 18D may include any of the same material construction configurations described with regard to FIG. 18C. The embodiment of FIG. 18D however has only a single row or column of tubes 18*bmt* and this makes the structure less rigid and relatively easier to bend along the longitudinal axes of the tubes 10*bmt*.

Figure 18E:
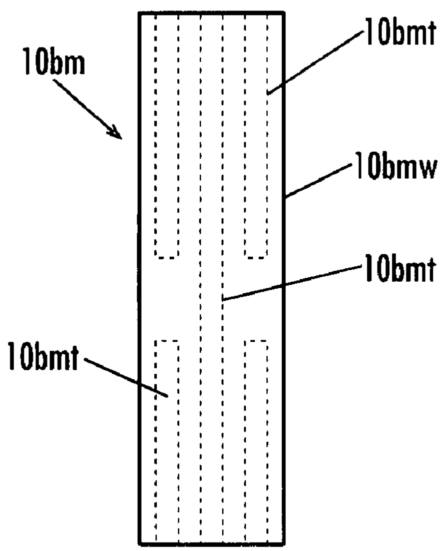

The bending strength of buoyancy member 10*bm* may be modified and tailored by making one or more tubes 10*bmt* discontinuous and by altering the lengths of the discontinuous tube(s) 10*bmt* as illustrated in FIG. 18E.

Figure 18F:
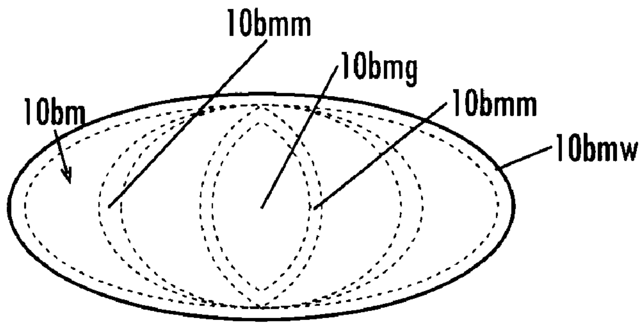

FIG. 18F illustrates a buoyancy member structurally supported by ribs 10*bmm* molded into the shaped that buoyancy member 10*bm* is desired to maintain. Walls 10*bmw*, which may be silicone, for example, completely encapsulate the ribs 10*bmm* thereby sealing the structure and encapsulating gas in the gaps 10*bmg*.

Figure 18G:
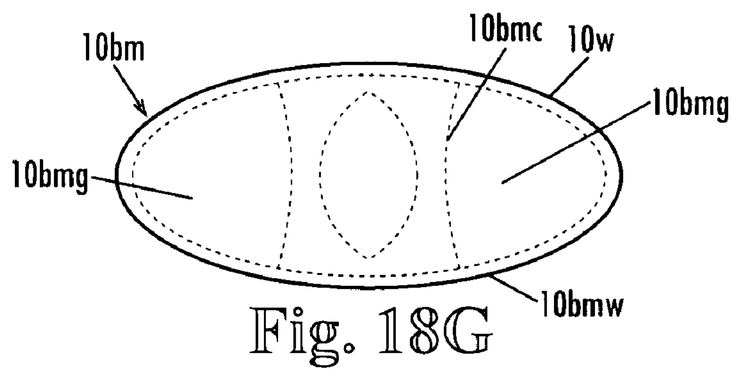

In FIG. 18G, a column structure 10*bmc* is provided to join opposing walls 10*bmw* and thus provide column strength to buoyancy member 10*bm* to maintain it in the configuration shown, thereby maintaining a volume of gas spaces 10*bmg* in which gas is encapsulated. It is noted that various other structure support members may be molded into walls 10*bmw* or positioned against the inner surfaces of walls 10*bmw*, or otherwise arranged to assist in holding the inner chamber 10*bmi* open to maintain a volume of gas to provide buoyancy. For example, any of the types of structural members described in provisional application No. 60/877,595 to assist in holding expandable member 10*em* open (for example, see FIGS. 9A-15D, 19A and 21-26B) can be used to help maintain the inner chamber of buoyancy member 10*bm* open.

Figure 18H:
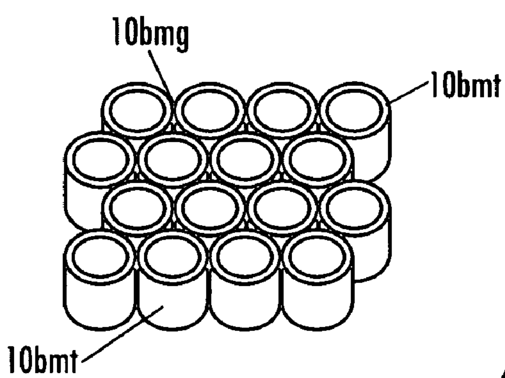

In FIG. 18H, a honey-comb-like arrangement of structurally supporting tubes 10*bmt* is provided. 10*bmg*. This structure can be encapsulated in a layer of polymer such as silicone, polyurethane, polyethylene, EVOH, or the like, or combinations thereof, thereby sealing off the annular spaces of the tubular members as well as the interstices between the tubular members.

Figure 18I:
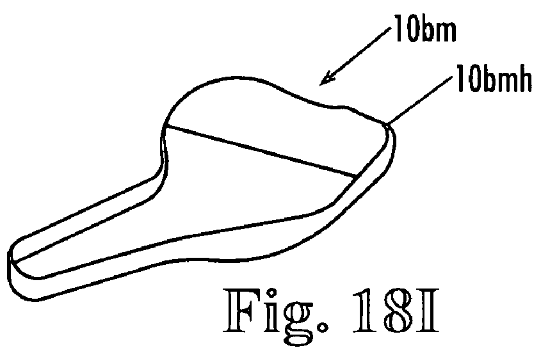

FIG. 18I illustrates a foam sheet 10*bmh* that can be cut out in a two-dimensional shape that can then be shaped into a three-dimensional shape and bonded to an inner surface of expandable member 10*em* to form a buoyancy member 10*bm*. For example, sheet 10*bmh*, could be manipulated to form an eggplant-shaped buoyancy member bonded to expandable member 10*em*, like shown in FIG. 15. Clearly, sheet 10*bmh* can be cut out to form many other varying shapes of three dimensional buoyancy member when bonded to the expandable member 10*em*. By rolling the edges of the sheet 10*bmh* and bonding them to an inner surface of expandable member 10*em*, an inner chamber 10*bmi* is formed that encapsulates gas therein. The sheet can be encapsulated to provide an additional barrier between the gas within the foam and the saline outside the foam. The encapsulation layer can be assembled around the foam, or dipped onto it, or established by LIM. The encapsulation layer (as well as any other encapsulation layers or other coatings described herein) can be further coated on the outside with a layer of parylene to provide a better barrier to fluid permeability.

Figure 18J:
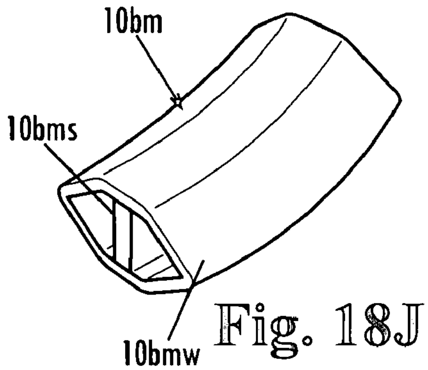

FIG. 18J illustrates an embodiment formed like described with regard to FIG. 18A (only with one strut 10*bms*), but is shown to illustrate more generally, that any of the embodiments described above can be molded or otherwise formed with a predetermined curvature designed to conform to the contour of the inner wall of expandable member (in the expanded configuration) to which it is to be fixed. Although shown open ended, both ends of buoyancy member are sealed off in the final product to encapsulate the gas therein.

Figure 18K:
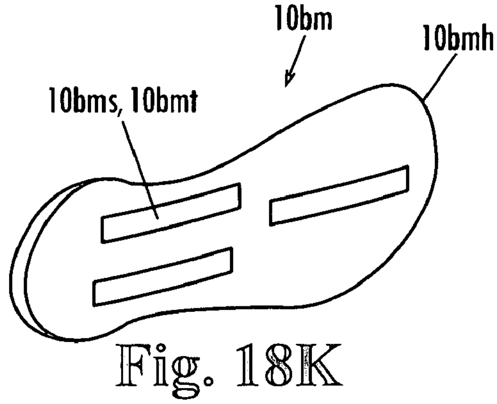

FIG. 18K illustrates an embodiment wherein sheet 10*bmh* is provided with one or more struts 10*bms* or tubes 10*bmt* (which may be foam or any of the other materials discussed above) to provide structure support to maintain the three-dimensional shape of sheet 10*bmh* as it is sealed to the inner surface of a wall of expandable member 10*em*, and to help maintain the gas in the chamber formed thereby.

An alternative method of partially or completely foam filling a buoyancy member includes molding the buoyancy member 10*bm* in the desired shape, bonding all but an inferior portion of the wall edges 10*bmw* to an inner surface of expandable member 10*em*, and then inserting a foam insert, either shaped to completely fill the molded buoyancy member 10*bm* or to provide structural supports (struts, tubes, or the like), after which the remaining inferior portion of the wall edge 10*bmw* can be sealed to the inner surface of the expandable member 10*em*.

Figure 19A:
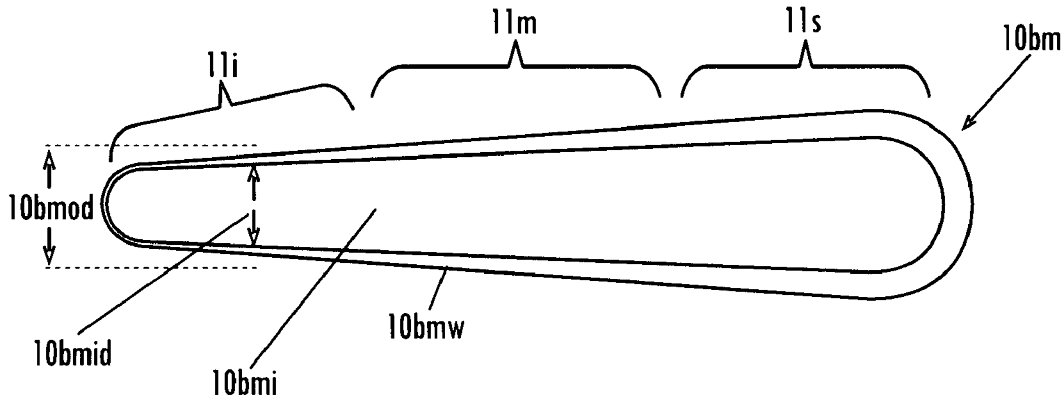
FIGS. 19A-19B illustrate two different examples of molded buoyancy members that can be used as an internal spine.
Figure 19B:
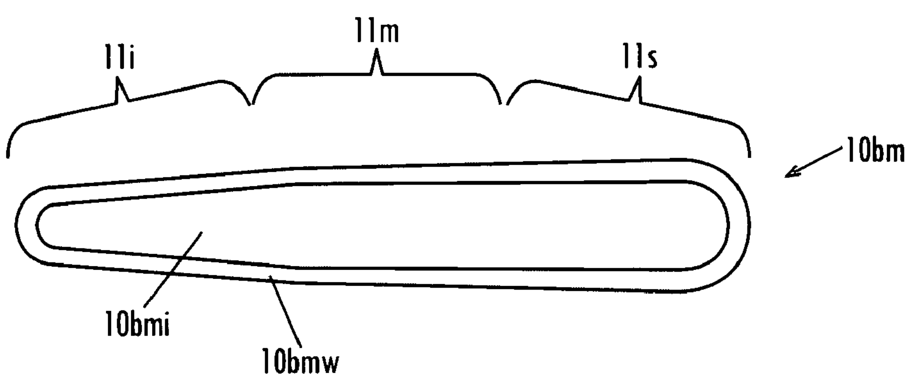

FIGS. 19A-19B illustrate two different examples of molded buoyancy members that can be used as an internal spine like described above with regard to FIGS. 15-16. In FIG. 19A, the foam body of buoyancy member 10*bm* is molded to have a constantly transitioning increase in outside diameter/dimension from a small end 11*i* through a middle portion 11*m* to a large end 11*s*. The thickness of wall 10*bmw* also gradually increases with a tapering increase of thickness from small end 11*i* through middle portion 11*m* to large portion 11*s*. Likewise, the inside diameter or dimension 10*bmid* that defines the gas cavity 10*bmi* gradually transitions or tapers from a smallest dimension at the small end and constantly increases through the middle portion 11*m* to the large end portion 11*s* (where it then necessarily rounds off to close the end of the buoyancy member 10*bm*). In one particular embodiment, buoyancy member 10*bm* has an outside diameter or dimension 10*bmod* at the small end 11*i* of about 0.85" which constantly transitions to an outside diameter or dimension 10*bmod* of about 1.85" at the large end 11*s*; a thickness of wall 10*bmw* of about 0.125" at small end 11*i* constantly increasing to a thickness of wall 10*bmw* of about 0.225" at large end 11*s*; and an inside diameter or dimension 10*bmid* of about 0.60" at small end 11*i* constantly increasing to the largest diameter or dimension of about 1.40" at the large end portion.

In FIG. 19B, the foam body of buoyancy member 10*bm* is molded to have a constantly transitioning increase in outside diameter/dimension from small end 11*i* to middle portion 11*m*, and then remains substantially constant from middle portion 11*m* to large end 11*s*. The thickness of wall 10*bmw* also gradually increases with a tapering increase of thickness from small end 11*i* to middle portion 11*m* and then remains substantially constant through middle portion 11*m* and large portion 11*s*. Likewise, the inside diameter or dimension 10*bmid* gradually transitions or tapers from a smallest dimension at the small end 11*i* and constantly increases to middle portion 11*m* and then remains substantially constant through middle portion 11*m* and large end portion 11*s* (where it then necessarily rounds off to close the end of the buoyancy member 10*bm*). In one particular embodiment, buoyancy member 10*bm* has an outside diameter or dimension 10*bmod* at the small end 11*i* of about 1.05" which constantly transitions to an outside diameter or dimension 10*bmod* of about 1.50" at the middle portion 11*m* and this dimension remains about 1.50" through to the large end portion 11*s*; a thickness of wall 10*bmw* of about 0.175" at small end 11*i* tapering up to a thickness of wall 10*bmw* of about 0.20", which remains substantially constant through the middle and large end portions 11*m* and 11*s*, respectively; and inside diameter or dimension 10*bmid* of about 0.70" at small end 11*i* tapering up to a diameter or dimension 10*bmid* of about 1.10" at the middle portion 11*m* and the large end portion 11*s*.

Figure 20:
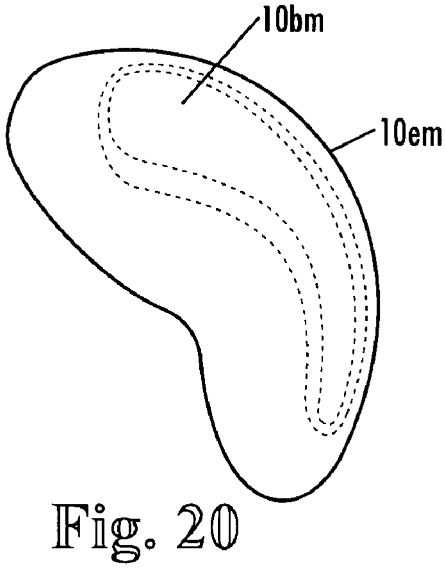
FIG. 20 illustrates a buoyancy member fixed to an inner surface of an expandable member.

Although appearing flat in the two dimensional illustrations of FIGS. 19A and 19B, buoyancy member 10*bm* may be formed with a twist along its longitudinal axis, so that the exposed wall edge 10*bmw* shown is not planar, but follows a curvature resulting from the twist that is determined to better follow the contour of the inner surface of expandable member 10*em*. FIG. 16 attempts to illustrate this curvature resulting from the twist. FIG. 20 also illustrates this curvature, with buoyancy member 10*bm* fixed to the inner surface of expandable member 10*em* at a portion that twists from the inferior attachment location moving toward the superior attachment location. It is further noted that the wall of expandable member 10*em* can be reinforced in the location where buoyancy member is attached thereto, as described in greater detail below. While FIG. 20 illustrates what appears to be a curvature in one dimension (in the plane of the paper), the curvature may additionally be in a second dimension (in and out of the paper). Such a complex curvature may best fit the complex curvature of the inner surface of expandable member 10*em* where buoyancy member 10*bm* is attached. Such a complex curvature allows the spine/buoyancy member 10*bm* to start and end at the most desirable locations to structurally support the expandable member 10*em*. For example, in this embodiment, the start point is among the attachment tabs 150 (e.g., see FIG. 22). The structure of the spine 10*bm* then extends from the abdominal attachment location of the expandable member 10*em* to the furthest apex of expandable member 10*em* and thus performs two functions: 1) spine/buoyancy member 10*bm* provides structure which helps to transfer the weight of the cantilevered expandable member 10*em* (when anchored to the abdominal wall) back to the abdominal attachment; and 2) spine/buoyancy member 10*bm* provides the most buoyancy at the apex portion/superior portion of expandable member 10*em*, so as to minimize twisting forces and lifting on inferiorly located portions.

Figure 21:
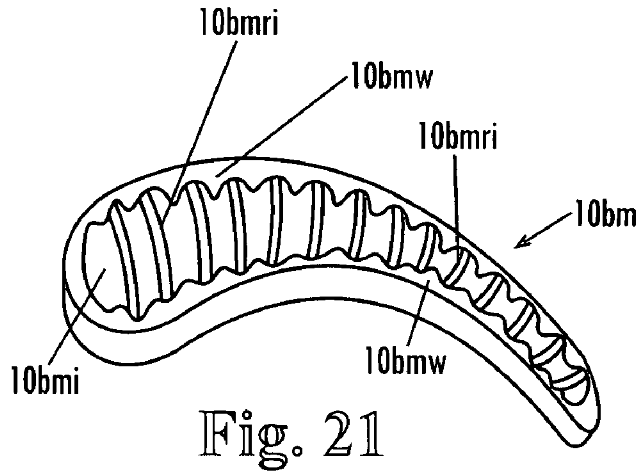
FIG. 21 shows an alternative embodiment of buoyancy member that is molded from foam.

FIG. 21 shows an alternative embodiment of buoyancy member 10*bm* that is molded from foam and has a twisted teardrop or eggplant shaped conformation. In this embodiment the walls 10*bmw* are thinned down, relative to previous embodiments described, by scalloping to reduce the overall weight of the molded product. Ribs 10*bmri* are molded in to extend from the inside surface of the wall in the locations of the scallops to provide additional rigidity for to hold open the space 10*bmi* to maintain a desired volume of gas therein to provide buoyancy. In one particular embodiment, buoyancy member 10*bm* is molded from silicone foam into this conformation. Alternatively, buoyancy member can be made from normal silicone, wherein the volume of air in the internal chamber of buoyancy member 10*bm* provides sufficient buoyancy to offset the weight of the normal silicone and still provide enough buoyancy to help offset the weight of the saline in expandable member 10*em*.

Figure 22:
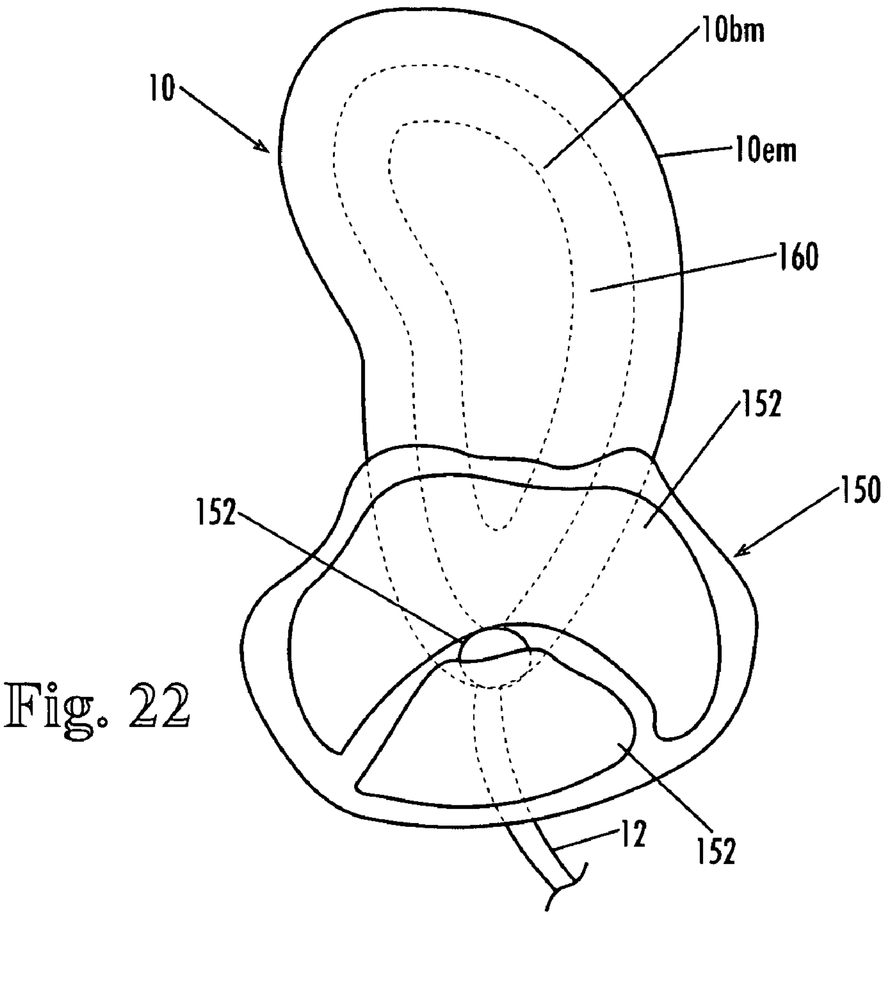
FIG. 22 illustrates an embodiment of a device having a buoyancy member attached to an inner wall surface of an expandable member to form an internal, buoyant spine.

FIG. 22 illustrates an embodiment of device 10 having buoyancy member 10*bm* attached to an inner wall surface of expandable member to form an internal, buoyant spine in a manner as described above. Expandable member 10*em* further includes a reinforcement layer 160 that extends over a majority of the length of expandable member 10*em* and may extend over substantially the full length of expandable member 10*em*. The portion of the wall of expandable member 10*em* covered by reinforcement layer 160 typically includes at least the area opposite the area the buoyancy member is attached to, and may include a substantial margin beyond this area in any direction, up to and including all directions, such as is shown in FIG. 22, for example. Reinforcement layer 160, provides structural support of expandable member 10*em* to reduce chances of the expanded configuration kinking by bending along its longitudinal axis. Cyclic actions of such kinking can produce wear and even failure of the expandable member, so the addition of reinforcement layer 160 performs a useful stiffening function. Together with buoyancy member 10*bm* functioning as an internal spine, this arrangement of reinforcement layer 160 and buoyancy member 10*bm* provides even more structural support to prevent kinking and otherwise maintain expandable member 10*em* in its desired orientation in the expanded configuration.

Reinforcement layer 160 may be made, for example, of silicone sheeting reinforced with a strengthening material such as woven polyester, polytetrafluoroethylene, or the like. A margin of unreinforced silicone can be maintained all around the edges of the sheet to facilitate bonding to expandable member 10*em* and to avoid stress concentration at the edges. Bonding can be performed, for example, using room temperature vulcanizing silicone adhesive, or vulcanizing a sheet or cut form of unvulcanized rubber, for example. Alternatively, reinforcement layer 160 may be made from a different polymer, such as polyurethane, for example, and reinforced with polyester mesh, for bonding onto a expandable member 10*em* having a polyurethane outer wall surface.

Alternative formulations from which expandable member 10*em* may be made include, but are not limited to: polyurethane compositions including silicon-containing chain extenders, such as taught in U.S. Pat. Nos. 6,420,452 and 6,437,073, for example, or segmented block polyurethane copolymers, such as taught in U.S. Pat. No. 5,428,123, or other combined polymer compositions of polyurethane and silicone resulting in less permeability (to gas and/or liquid) than that of polyurethane used alone, or silicone used alone. Additionally, these improved barrier (resistance to permeation) properties can be achieved with a thinner wall thickness than would be required if using polyurethane alone, or silicone alone. Optionally, buoyancy member 10*bm* may also be made from any of these same materials. U.S. Pat. Nos. 6,420,452; 6,437,073; and 5,428,123 are hereby incorporated herein, in their entireties, by reference thereto.

To facilitate anchoring of device 10, device 10 may be provided with one or more attachment tabs 150. Attachment tab(s) 150 fan out like wings from the surface of expandable member 103*m* to provide a much broader attachment surface area compared to what would be provided by simply attaching the portion of the expandable member 10*em*, from which they extend, to a structure. FIG. 22 illustrates a single continuous attachment tab 150 that extends from expandable member 10*em* about a circumferentially extending portion of the surface of the inferior portion of expandable member 10*em*. Attachment tab 150 may be bonded to the surface of expandable 10*em*, such as with silicone dip layer, for example, or using room temperature vulcanizing silicone adhesive, or using unvulcanized silicone sheeting between tab(s) 150 and expandable member 10*em* and then vulcanizing by heat pressing. By bonding to a portion of reinforcement layer 160, stress forces generated by movements of the patient, for example, through attachment tab(s) which are anchored to the patient, can be distributed over the reinforcement layer 160. Additionally, border portions of tab(s) 150 can be sandwiched between expandable member 10*em* and reinforcement layer 160, thereby further reinforcing the connection between attachment tab(s) 150 and expandable member 10*em*. If the attachment tab(s) is/are made from polyurethane to be bonded to a polyurethane expandable member 10*em* wall, a solvent bond can be performed using a slurry mixture of polyurethane. By extending the superior edge of tab 150 continuously and integrally across the width of expandable member 10*em*, this strengthens the bond and eliminates stress concentrations that could lead to delamination of tabs individually bonded to opposite side portions of expandable member 10*em*.

Alternatively, multiple attachment tabs 150 can be placed at locations around expandable member 10*em* to extend from and substantially cover areas covered by the larger single attachment tab 150 shown in FIG. 22, although this may introduce locations of stress concentration at the bonded corners of the individual tabs 150 (e.g., peel force attempting to peel tab 150 away from expandable member 10*em*), as noted. However, an advantage is provided by multiple individual tabs 150 in that the tabs are more easily able to conform to the structure that they are being attached to, particularly if there is some curvature or other surface shape other than planar in the structure. That is, tabs 150 can be overlapped to reduce the overall coverage of the structure to be attached to and this increases the convexity of the attachment surfaces formed by tabs 150, or tabs 150 can be otherwise changed in relative position to better match a surface shape to be conformed to, or spread apart to increase the concavity of the attachment surfaces formed by tabs 150, for example. The overlapping prevents folds or wrinkles that would otherwise occur with a single tab 150 such as like that in FIG. 22. The use of attachment tab(s) 150 also gives the surgeon the option to not use conduit 12 to perform an anchoring function. This allows an access member connecting to conduit outside of the abdominal wall to be placed further away from the ribs, potentially offering the patient less discomfort, and also allows conduit 12 to be placed so that it is not under tension to perform an anchoring function, thereby lessening the mechanical requirements for conduit 12. Attachment tabs 150, although typically located to extend from the inferior portion of expandable member 10*em*, need not be so located, but can be placed to extend from any locations on device 10 or expandable member 10*em*.

Figure 23:
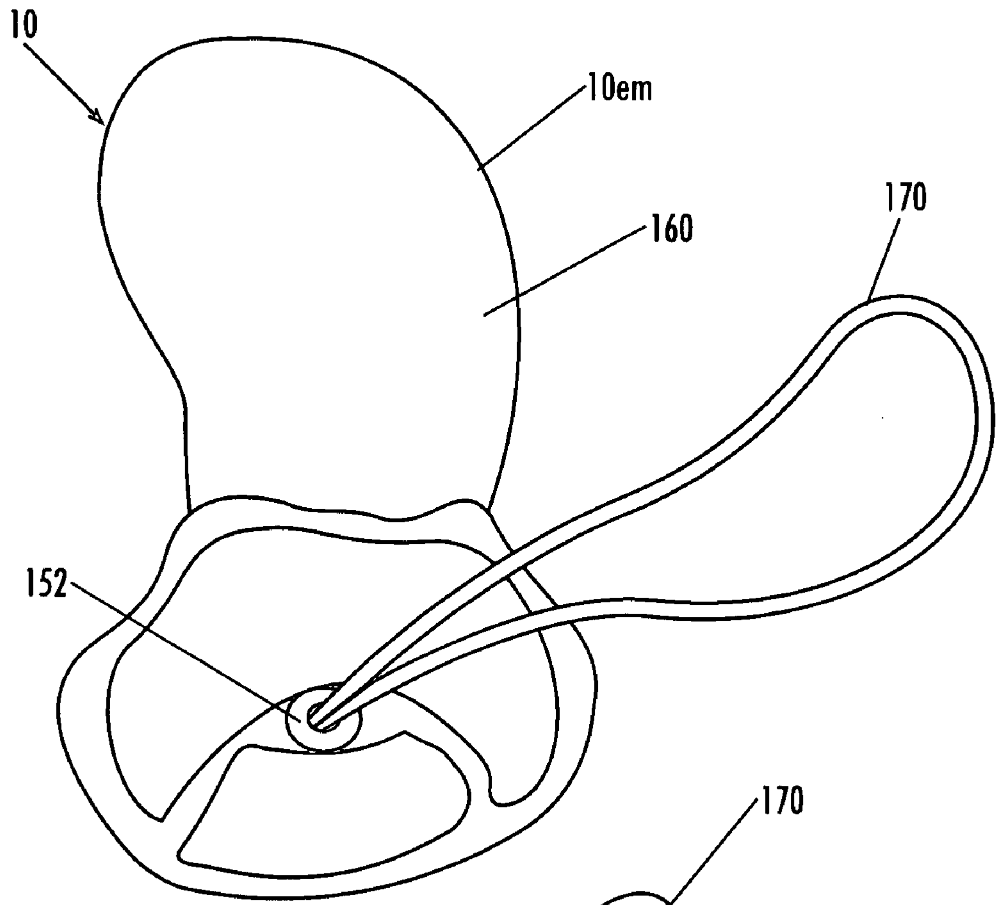
FIG. 23 illustrates a device having an elongated positioning loop attached thereto.

Tab 150 will typically be formed from a reinforced sheeting, such as polyester-reinforced silicone sheeting, polypropylene-reinforced silicone sheeting or polyethylene-reinforced polyurethane sheeting for example, or any other biocompatible fabric that can be sandwiched between two layers of biocompatible polymers or rubbers. One or more patches 152 of tissue ingrowth enhancing material, such as a expanded polytetrafluoroethylene, polytetrafluoroethylene, polyester, etc, in felt or velour configuration, or polypropylene mesh, for example, can be bonded onto the reinforced sheeting so that, when placed in contact with tissue, tissue is encouraged to grow into the patches. An additional tissue ingrowth enhancing patch 152, such as the circular one illustrated in FIG. 22 may be provided through which an elongated positioning loop 170 may extend, as illustrated in FIG. 23. This tissue ingrowth enhancing patch 152 not only encourages tissue ingrowth from the tissue location to which it is drawn against by positioning loop 170, but also reinforces the junction of positioning loop 170 to device 10, strengthening the junction.

FIG. 22 illustrates device 10 including the optional positioning loop 170 connected to expandable member 10*em* through tissue ingrowth enhancing patch 152 and optionally to reinforcement layer 160. Positioning loop 170 is typically a long lightweight loop of polymer, such as a ribbon and may be formed from polypropylene mesh ribbon or the like. After inserting device 10 through an opening in the patient and into the abdominal cavity (positioning loop 170 is also inserted into the abdominal cavity), a surgeon can form an additional puncture through the patient at another location in the abdomen in line with a location on the abdominal wall where it is desired to anchor the inferior end portion of device 10 to the abdominal wall. This puncture can be very minimal and performed using a needle, needle that includes a hook, or other sharp, minimally invasive tool. Using the same tool or a different minimally invasive hook tool or graspers, loop 170 is captured and drawn out through the additional puncture. By applying tension to positioning loop 170, the inferior end portion of device 10 and particularly ingrowth patch 152 can be drawn up against the internal surface of the abdominal wall for anchoring there. Anchoring of the tab(s) 150 can be done prior to or after inflation of expandable member 10*em*. In one typical example, expandable member 10*em* can be expanded with gas or liquid prior to anchoring to facilitate proper positioning of device 10 prior to anchoring tab(s) 150. One practical approach is to inflate expandable member 10*em* with gas to check for positioning, since inflation with gas is faster and easier than inflation with liquid. Once proper positioning is confirmed, expandable member 10*em* can then be quickly deflated, and anchoring of attachment tab(s) can then be performed. By performing anchoring of attachment tab(s) with expandable member 10*em*, this provides more working space and/or better visibility to accomplish the anchoring. After anchoring, expandable member 10*em* can then be inflated with liquid. The ribbon portions of loop 170 adjacent the exterior surface of the abdominal wall can be sutured or otherwise fixed to the abdominal wall, and the portions of loop 170 proximal of the fixation location can be severed and removed from the patient.

Figure 24:
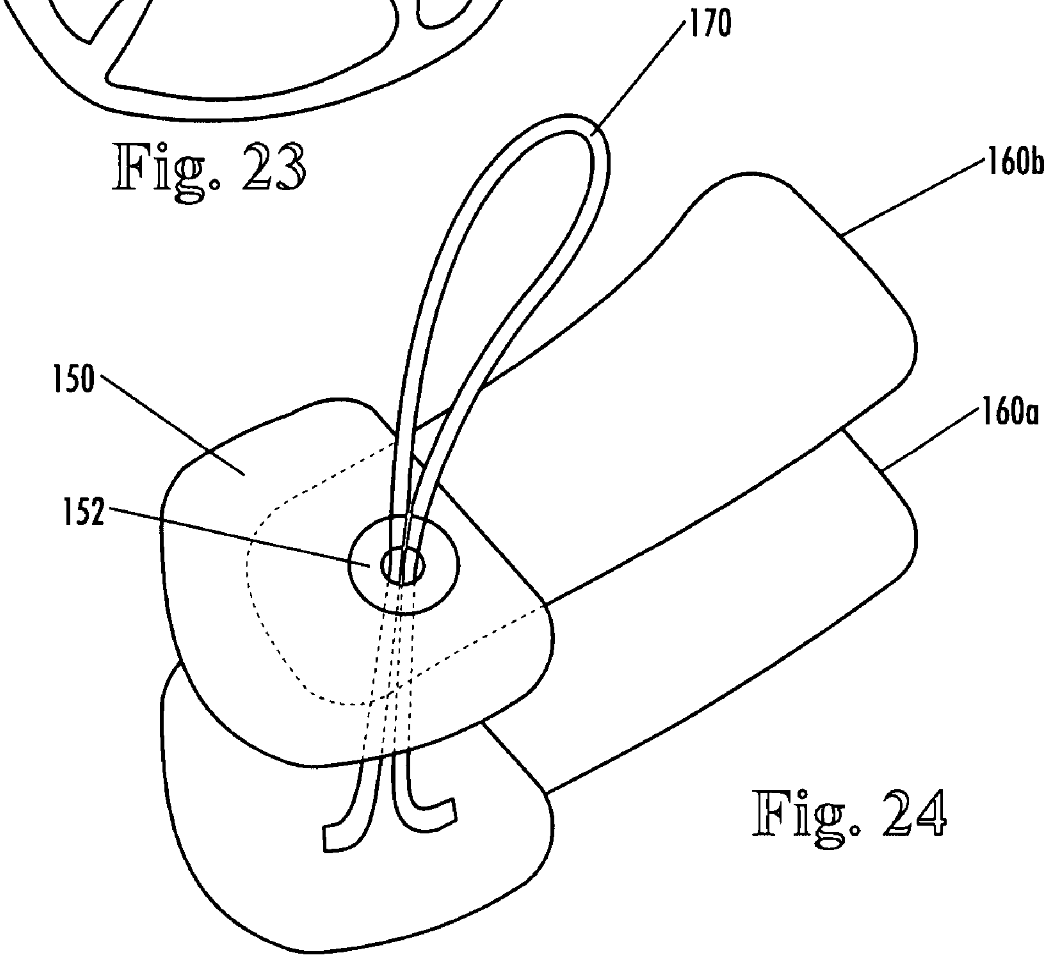
FIG. 24 illustrates an exploded view of reinforcement tab and loop structures, demonstrating one method of bonding these structures to an expandable member.

FIG. 24 illustrates an exploded view of reinforcement tab and loop structures, demonstrating one method of bonding these structures to expandable member 10*em*. In this embodiment, dual reinforcement layers 160*a* and 160*b* are provided. Positioning loop extends through openings provided in the reinforcement/tissue ingrowth patch 152, tab 150 and reinforcement layer 160*b*, and the ends of the ribbon 170 are bonded to the inner reinforcement layer 160*a*. Tab 150 is bonded to outer reinforcement layer 160*b* and reinforcement/tissue ingrowth patch 152 is bonded to tab 150 or to outer reinforcement layer 160*b*. Outer reinforcement layer 160*b* is bonded to inner reinforcement layer 160*a* according to any of the techniques described above for bonding reinforcement layer 160 to expandable member 10*em*, thereby sandwiching and securely anchoring the free ends of ribbon 170 therebetween. The resulting construct can be bonded to expandable member 10*em* according to any of the techniques described above for bonding reinforcement layer 160 to expandable member 10*em*.

Figure 25A:
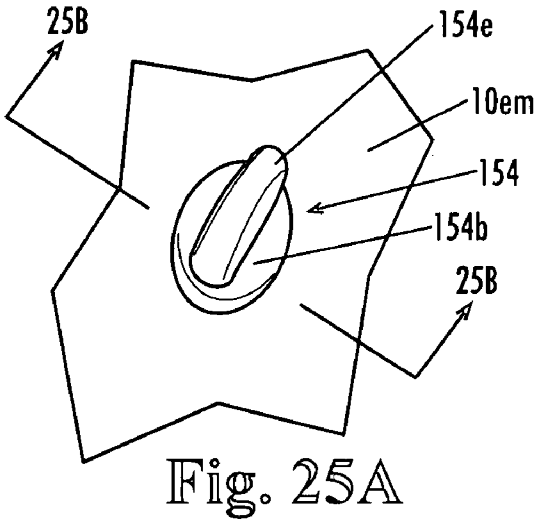
FIG. 25A illustrates a positioning tab bonded to a portion of an outer surface of an expandable member.
Figure 25B:
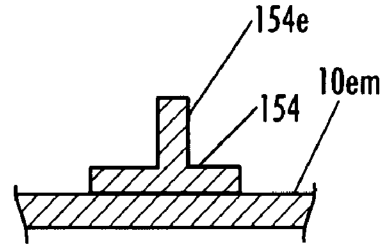
FIG. 25B is a cross sectional view of FIG. 25A taken along line 25B-25B.
Figure 25C:
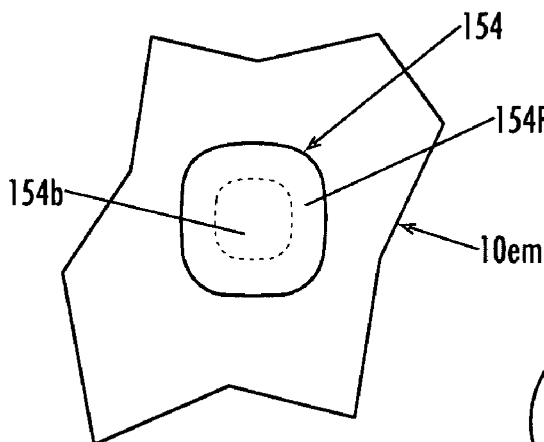
FIG. 25C shows a positioning tab that lies substantially flush with a surface of an expandable member.

FIGS. 25A-25C illustrate additional tab features that may be provided on device 10, such as on expandable member 10*em* to assist in positioning/repositioning the device in the abdominal cavity. FIG. 25A illustrates a portion of the outer surface of expandable member 10*em* to which is bonded positioning tab 154. This positioning tab has a base 154*b* bonded to the surface of the expandable member 10*em* and a extending portion, such as fin 154*e* or other tab extension that does not lie flush with the expandable member 10*em* surface, but extends therefrom to allow a surgeon to grasp this portion using endoscopic graspers or other tool that can be inserted through a small opening in the patient to perform a grasping function. Once grasped, the tool can be pulled, pushed or otherwise manipulated to move the position of the expandable member 10*em*. The cross sectional view of FIG. 25B more clearly shows the extending fin portion 154*e* of positioning tab 154.

FIG. 25C shows a positioning tab 154 that lies substantially flush with the surface of expandable member 10*em*. However, only the central portion of tab 154 (bonded portion 154*b*) is bonded to expandable member 10*em* with the borders 154*f* left unsecured. Accordingly, graspers or other instrument can grab a portion of the free perimeter 154*f* at the border of positioning tab 154 to apply forces therethrough to move the position or orientation of expandable member 10. In either configuration, one or more positioning tabs can be bonded at any locations on the expandable member 10*em* that a surgeon may find useful to apply leverage to position or orient the expandable member.

Figure 26A:
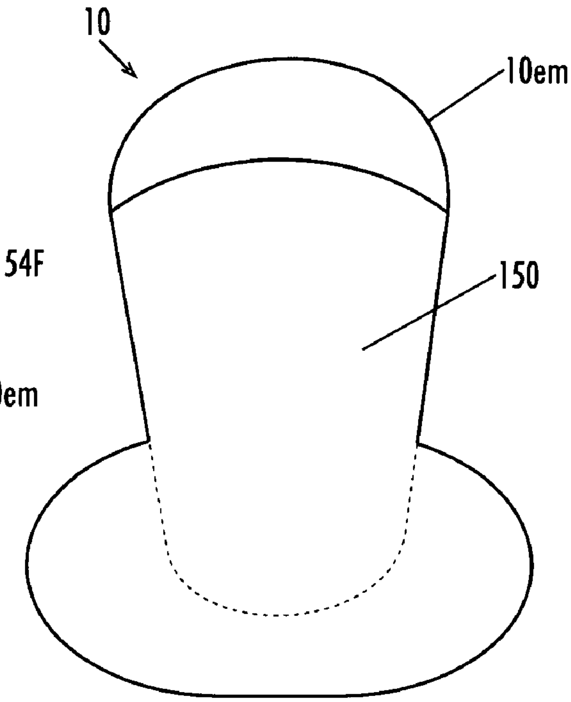
FIGS. 26A-26B illustrate an embodiment where tab(s) is/are extended to provide a shell-like rigidifying support of an expandable member.
Figure 26B:
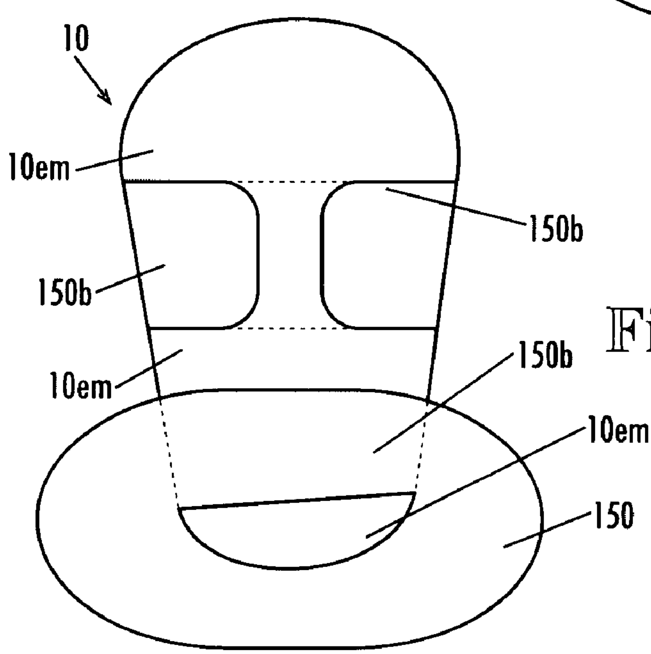

FIGS. 26A-26B illustrate an embodiment where tab(s) is/are extended to provide a shell-like rigidifying support of expandable member 10*em*. FIG. 26A shows the anterior surface of tab 150 and expandable member 10*em* showing tab 150 extending over a majority of the length of expandable member 10*em*. This extended tab 150 can be bonded to expandable member 10*em* with or without one or more reinforcement layers 160 therebetween, as well as with or without stress relief feature 160F. FIG. 16B shows the posterior surfaces of tab 150 and expandable member 10*em* showing that tab 150 wraps partially (or optionally, completely) around the posterior surface of expandable member, forming both inferior and superior bands 150*b*.

Figure 26C:
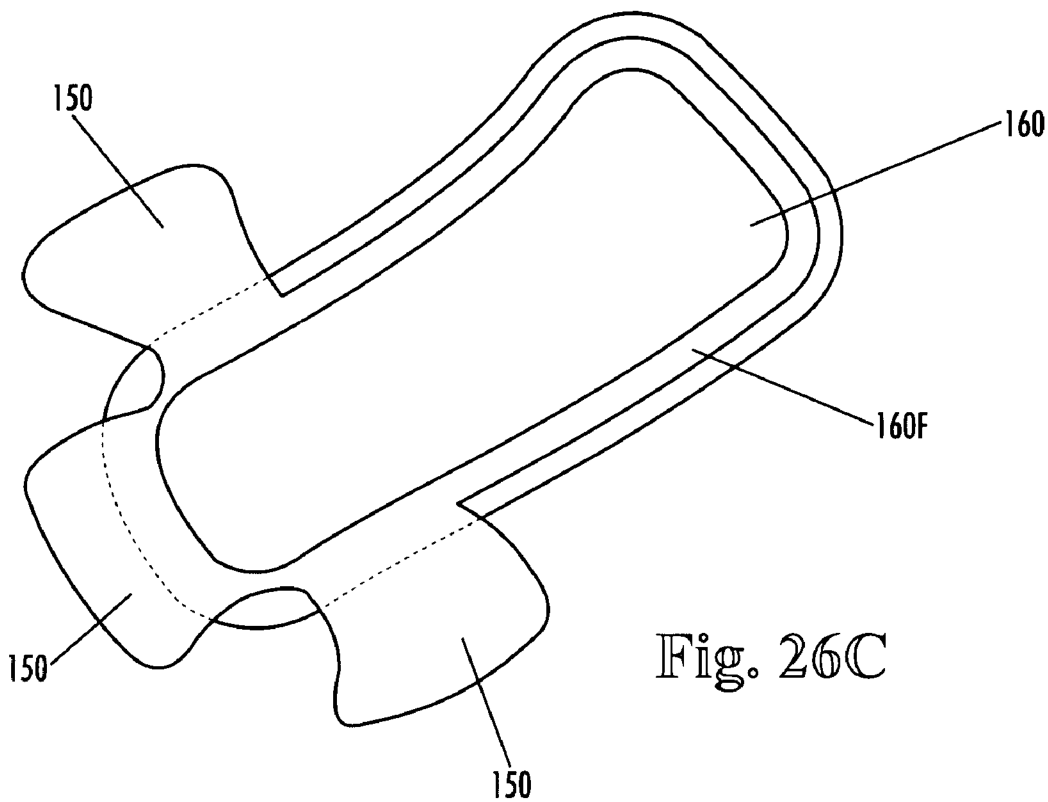
FIG. 26C illustrates a configuration where a reinforced frame structure or reinforcement backing layer extends superiorly of tabs.

FIG. 26C illustrates a configuration where a reinforced frame structure or reinforcement backing layer 160 extends superiorly of tabs 150 and may be formed in sandwiched, laminated construction with a portion of tab(s) 150 at an inferior portion of the reinforcement backing layer 160. A stress relief feature 160F may be provided at the reinforcement layer 160-expandable member 10*em* (optionally, as well as interface borders between tab(s) and expandable member 10*em*) to diffuse stress concentrations that would otherwise build up between the backing layer 160 and expandable member 10*em*, as there is a significant difference in compliance properties between the fabric reinforced backing layer 160 and the non-reinforced polymer layer of expandable member 10*em*. For example, when expandable member is made of silicone and backing layer is made of polymer fabric-reinforced silicone, stress-relief feature 160F may be a bead of RTV silicone, or a cut sheet of unvulcanized silicone sheeting that is pressed and vulcanized to bond to expandable member 10*em* and backing layer 160.

Figure 27:
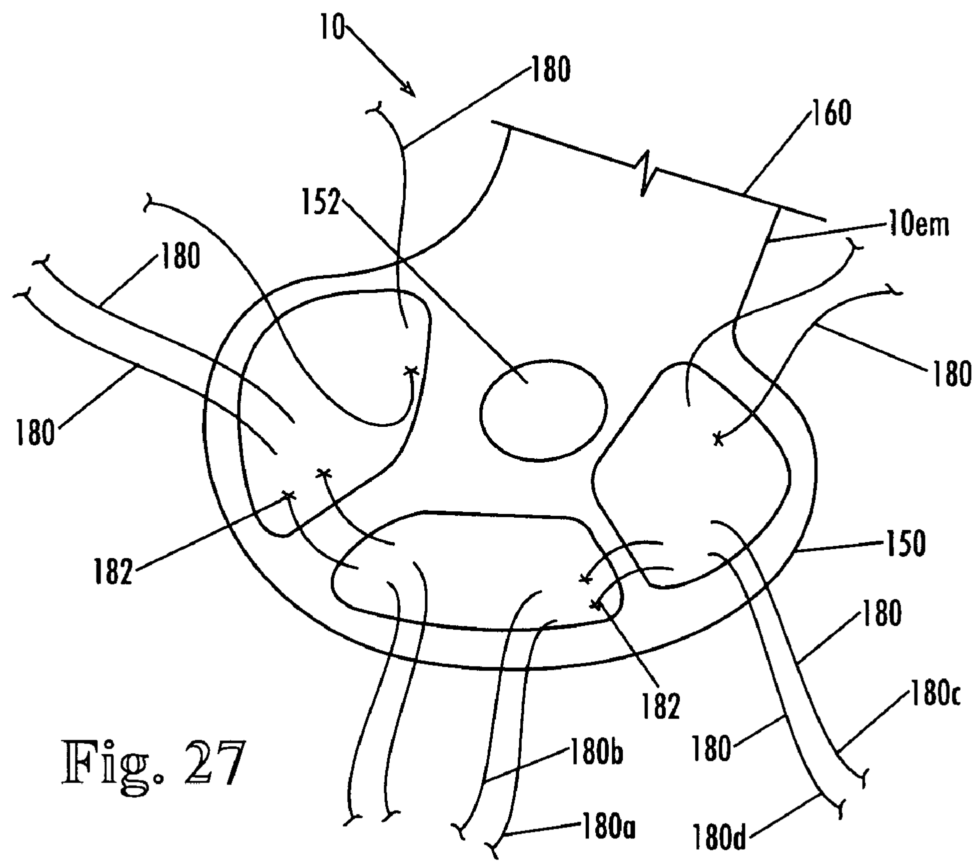
FIG. 27 shows an inferior portion of a device to illustrate an alternative arrangement for fixing or anchoring tab(s) to an internal abdominal structure.

Tab(s) 150 can be fixed to an internal abdominal structure (such as an internal surface of the abdominal wall for example) using staples or tacks in a manner as described in co-pending application Ser. No. 11/716,985, which was incorporated by reference above, or sutures, or Q-ring fixation members 150Q (see FIG. 26D) that are configured like the coil portion of key ring, that can be threaded into and through the tab 150 and tissue for anchoring these together, or hooks, barbs, corkscrew type anchoring members, or other known anchoring arrangements. FIG. 27 shows an inferior portion of device 10 to illustrate an alternative arrangement for fixing or anchoring tab(s) to an internal abdominal structure, which may be an internal surface of the abdominal wall and/or other internal abdominal structure. In this embodiment, sutures 180 are inserted through tab(s) 150 at least one location (at least one location into and at least one location out of, respectively) to form a loop that can be drawn against by drawing on the free ends of the suture to draw the tab(s) up against an internal abdominal structure to be sutured thereto. In the embodiment shown, there are single sutures 180 that pass into, through and out of tab 150 and tissue ingrowth patch at one location in and one location out. Additionally shown are sutures 180 (in pairs in this example, although this is not necessary) that pass into and out of tab 150 at two different locations, one into and out of a first tissue ingrowth patch 152 and a second, into and out of an adjacent tissue ingrowth patch. It is noted that this arrangement is only exemplary, as other patterns of sutures 180 could be used to accomplish the method to be described hereafter. It is further noted, that in embodiments that employ multiple attachment tabs 150, sutures 180 that extend through adjacent tabs 150, when pulled on, can also be used to reposition tabs 152 relative to one another prior to fixing them to the internal abdominal structure. For example, drawing opposite ends of a suture 180 may draw adjacent tabs 150 closer to one another and or cause them to partially overlap. Sutures 180 may be provided with one or more knots or other enlargements 182 that cannot pass through the tissue ingrowth patch 152 or tab 150, to prevent sutures 180 from sliding out of the tab(s) 150.

After insertion of device 10 through an incision in the patient and into the abdominal cavity, the inferior portion can be generally located against the internal abdominal structure that it is to be anchored to by forming a puncture aligned with that location and retracting loop 170 therethrough to pull the inferior portion of device 10 into contact with the internal abdominal structure, as was described above. It is noted that positioning loop 170 is not shown in FIG. 27 in order to clarify the illustration of the sutures 180 shown and the routes into and out of tab 150. Once positioning loop has been anchored extra-abdominally (such as to the external surface of the abdominal wall, as one example), additional punctures are performed through the skin of the patient to grasp and retrieve ends of sutures 180. Opposite ends of a suture 180 are drawn through separate punctures that are generally aligned with the locations of tab 150 where the particular suture end extends from. When both ends of any particular suture 180 have been drawn through the respective puncture openings, the suture is then tied down by tying the two ends of the suture together and forming the tied knot as far down through the fat of the patient as possible, into contact with the fascia (or as close to the fascia as possible). This procedure is repeated for each pair of suture ends of each suture 180.

FIG. 28 schematically illustrates one suture 180 having been tied down to anchor a portion of tab 150 to the inner surface of abdominal wall 127. After creating the puncture/small opening 202 through the skin, subcutaneous tissues including fat, fascia 127 and abdominal wall 127 and retrieving positioning loop 170 therethrough, positioning loop is pulled to pull the inferior portion of device 10 including attachment tab(s) 150 against the inner surface of the abdominal wall in a general location where it is desired to anchor device 10 thereto. To assist in this movement, the surgeon may optionally grasp one or more positioning tabs 154 that may be located superiorly of tab(s) 150 on expandable member 10*em*, for example. Further orientation of device 10 may be performed after the inferior portion of device 10 is drawn against the abdominal wall 127 via positioning loop 170, and this further orientation may also be facilitated by pushing, pulling or torquing on one or more positioning tabs 154.

After fixing loop 70 to the outer surface of the abdominal wall 127 and/or fascia 127*f* and removing the excess loop portion extending proximally of the fixation point, as described above, an additional puncture 204 is formed in a general location overlying a location from which one end of suture 180 exits tab 150. The end is retrieved using graspers, or other minimally invasive retrieval instrument and pulled out of the patient's abdominal cavity and through the abdominal wall, optionally all the way out of the patient. Assuming there is at least one knot 182 formed in suture to prevent it from sliding out of tab(s) 150, then the retraction of the first end of the suture can be done without concern for holding the other free end of the suture. In this case, once the first free end of suture 180 has been drawn out of the abdominal cavity through puncture 204, a second puncture 206 is formed in a location overlying a general location from which the other end of suture 180 exits tab 150. The other one end of suture 180. This second end of suture is then retracted out of the abdominal cavity through puncture 206. Alternatively, first and second ends of the suture 180 can be retracted out of the abdominal cavity simultaneously through punctures 204 and 206, respectively. Either way, the two free ends of suture 180 are then tied down together as close to fascia 127*f* as possible. The knot formed between the two ends of the suture 180 is pushed down through the fat to be tied off at a location abutting, or as close to the fascia 127*f* as possible. This procedure is repeated for each suture 180, wherein additional pairs of punctures are created for retracting each additional pair of free ends of each additional suture 180, respectively.

In an alternative procedure, when pairs of sutures are provided, as in the arrangement shown in FIG. 27, for example, adjacent free ends of the pairs of sutures 180 can be tied down as close to the fascia as possible. For example, referring to FIG. 27, a first puncture can be made to drawn end 180*a* therethrough and a second puncture can be made very close to the first puncture to draw end 180*b* therethrough, and then ends 180*a* and 180*b* can be tied down together, close to or abutting the fascia 127*f*. Similarly, a third puncture can be made to drawn end 180*c* therethrough and a fourth puncture can be made very close to the third puncture to draw end 180*d* therethrough, and then ends 180*c* and 180*d* can be tied down together, close to or abutting the fascia 127*f*. An advantage to this technique is that because the ends to be tied together are so close to one another, the punctures to draw them out of the abdominal cavity can also be made very close to one another. This results in the tied suture loop 180 surrounding much less fat and therefore there is a reduced chance of loosening of the tie due to fat loss before sufficient tissue ingrowth has occurred in patches 152. Another advantage is that since the punctures for the adjacent suture ends to be tied can be made so close to one another, they can both be made from the same incision or puncture in the skin of the patient, while moving the graspers or other puncturing or incising instrument only slightly to form a puncture next to one that has already been made.

Alternatively, one or more of sutures 180 can be replaced by additional positioning loops 170 that are fixed to tab(s) 150 in locations where the ends of sutures 180 would otherwise extend out of tab(s) 150. Anchoring of the tab(s) 150 can then be performed by pulling loops 170 out of the abdominal cavity and tying them together in any of the manners described above with regard to sutures 180.

Further alternatively, it is noted that device 10 can be generally positioned for anchoring the inferior portion of device 10 without the use of positioning loop 170, with or without assistance of positioning tab(s) 154, and still anchor tab(s) using sutures 180 in any of the manners described above.

Figure 30A:
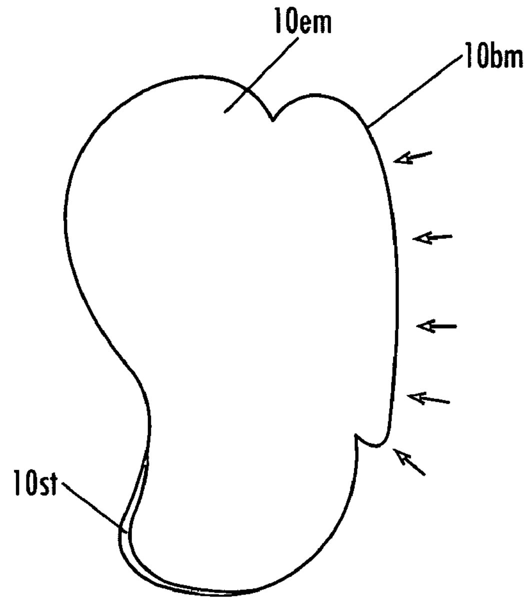
FIG. 30A illustrates the molded product after removing it from the mold shown in FIG. 29.

Alternatively to separately manufacturing a buoyancy member 10*bm* and expandable member 10*em* and then inserting (either with or without fixing to the expandable member) buoyancy member 10*bm* into expandable member 10*em* (either before or after insertion of expandable member 10*em* into the abdominal cavity), buoyancy member 10*bm* may be manufactured integrally with expandable member 10*e*. FIG. 29 shows a mold 15 that is three dimensionally shaped to form expandable member 10*em* and buoyancy member 10*bm* integrally as a single molded product. Portion 15*em* from the shape of expandable member 10*em* and portion 15*bm* extends from portion 15*em* to form the shape of buoyancy member 10*bm*. After molding the polymeric material over mode 15, a small slit can be made to peel the molded product off the mold 15. FIG. 30A illustrates the molded product after removing it from mold 15 via slit 10*st*, for example. Slit 10*st* can be closed by patching, such as bonding a sheet of silicone thereover using RTV silicone adhesive, for example, or by bonding with RTV silicone adhesive alone, or other equivalent sealing technique.

Figure 30B:
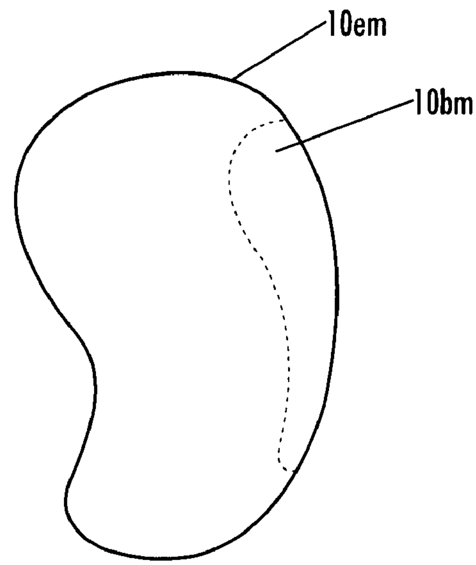
FIG. 30B shows the molded product of FIG. 30A pushing on the portion of the product that will form buoyancy member to invert it.
Figure 30C:
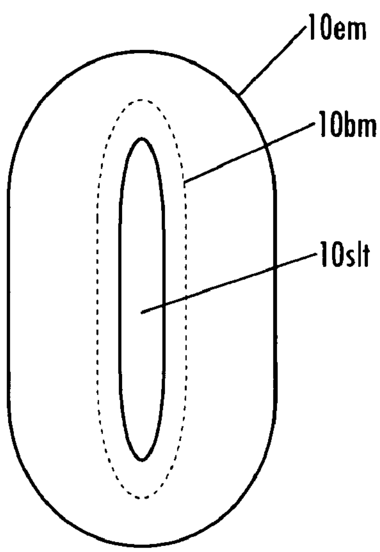
FIG. 30C illustrates an open channel or slot after inverting the buoyancy member portion as shown in FIG. 30B.

By pushing on the portion of the product that will form buoyancy member 10*bm* in the direction of the arrows shown in FIG. 30A, this portion can be inverted inside the main body portion that forms expandable member 10*em*, as illustrated in FIG. 30B. This leaves an open channel or slot 10*slt* in the wall of expandable member 10*em* as illustrated in the right side view of FIG. 30C. This slot 10*slt* can be closed by bonding a polymer layer (e.g., silicone sheet) over it, thereby closing off the internal chamber 10*bmi* and sealing gas therein. Alternatively, prior to sealing, a foam insert having a shape conforming to the buoyancy member 10*bm* can be inserted therein to hold buoyancy member 10*bm* open and, at the same time encapsulate gas therein. Further alternatively, a balloon or structural supporting elements of any of the types described above can be inserted into the inner chamber 10*bmi* prior to sealing off the slot 10*slt*.

Figure 31:
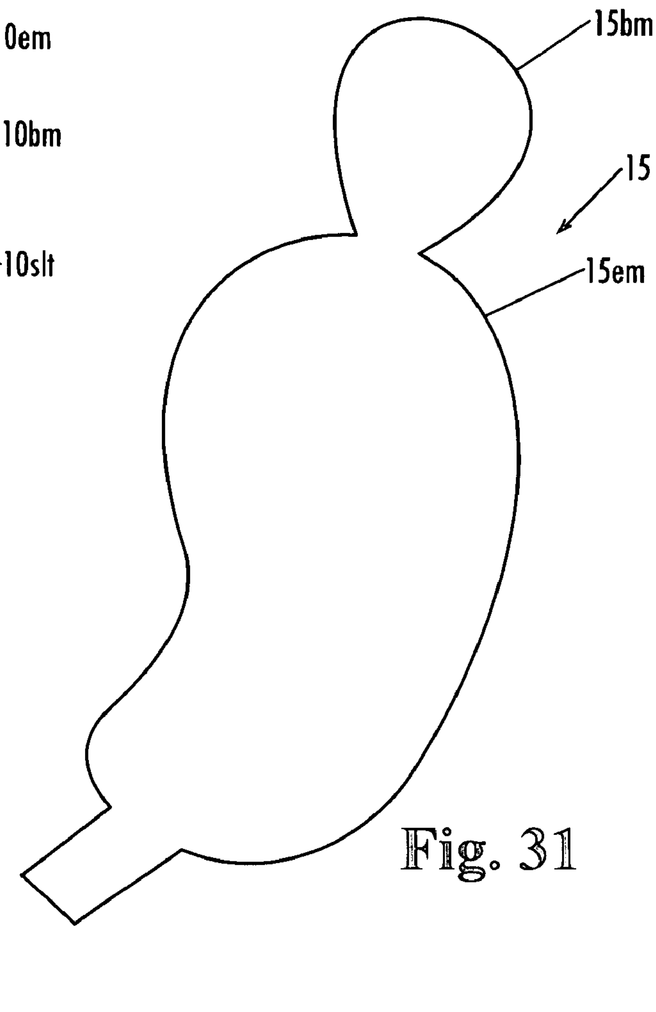
FIG. 31 illustrates an alternative mold in which a buoyancy portion is formed to extend superiorly of the superior portion of expandable member portion.

This technique is not limited to formation of a buoyancy member 10*bm* having a teardrop or eggplant-like shape, but can be applied to many other shapes of buoyancy members. Likewise, the shape of expandable member 10*em* is not limited to the shape shown. Further, this method is not limited to the placement of buoyancy member 10*bm* as an internal spine as shown. FIG. 31 illustrates an alternative mold 15 in which buoyancy portion 15*bm* is formed to extend superiorly of the superior portion of expandable member portion 15*em*, and is closer to spherical shape than eggplant shape. Alternatively, this method of assembling the buoyancy member 10*bm* onto the side area of expandable member 10*em* does not have to utilize a shape in expandable member 10*em* that is inverted. For example, in FIG. 30A, without the shape of 10*bm*, the shape of 10*em* would be more like what is shown in FIG. 30B. Given this shape, a flat sheet of foam can be adhered to the outside of the mold for expandable member 10*em*, and a layer of silicone could be layered over the foam to form the expandable member there.

Figure 32A:
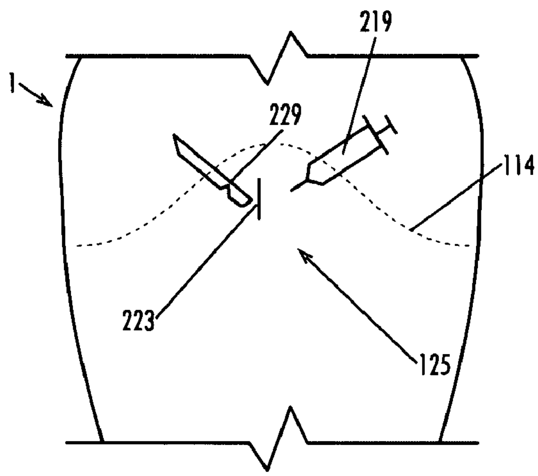
FIGS. 32A-32E illustrate steps that may be carried out during a procedure for implanting an expandable extra-gastric device according to an embodiment of the present invention.

FIGS. 32A-32E illustrate steps that may be carried out during a procedure for implanting an expandable extra-gastric device 10 according to an embodiment of the present invention. Prior to making an incision, the local area (the area of the skin in and surrounding the location where the incision is to be made) may be prepared by disinfecting with alcohol and or betadine. Additionally, the patient may be given a mild sedative or may be on conscious sedation. (Although not practiced in this particular procedure, a similar procedure could be practiced with placing the patient under general anesthesia, in which case anesthetics would not need to be injected as described in the next step.) Next a powerful local anesthetic such as marcaine (bupivicaine) or other powerful anesthetic, optionally mixed with an epinephrine or other vasoconstrictor to reduce any bleeding that might result from mild trauma, is injected into the local area through the skin 125 of the patient 1 down to the muscular layer and to infiltrate the fat layer and entire local area. Injection may be performed using a syringe 219, as illustrated in FIG. 32A, or other injection tool. After allowing time for the injected anesthesia to take effect, a small incision 223 (e.g., no greater than about seven cm or no greater than about five cm) is made in the skin 125 of the patient 1, with a scalpel 229 or other surgical cutting tool, in the local area over the surgical target area where device 10 is to be implanted. In the example shown, the incision 223 is made slightly inferior to the lower rib line 114. (FIG. 32A shows a frontal schematic view of the abdominal portion of the patient 1).

Figure 32B:
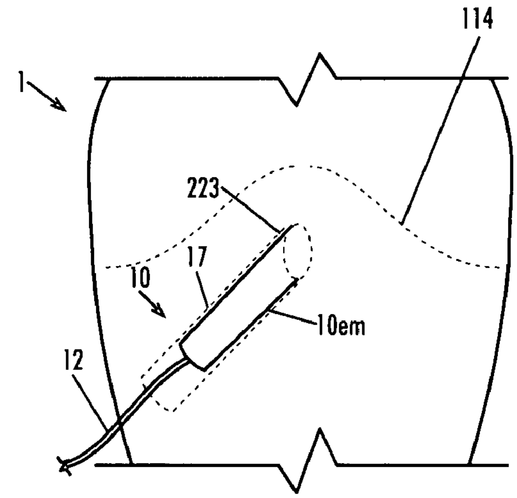

A delivery tract is then opened from opening 223 through the subcutaneous tissues and abdominal wall to provide an access opening into the abdominal cavity. For example, the delivery tract may be formed by starting with a small incision 223, 225 and then inserting a small port under visual guidance (for example, with VISIPORT™, or the like) to provide safe access into the abdominal cavity. Alternatively, the delivery tract can be made with a cannula and a veress-style needle within it which is subsequently exchanged, after access into the abdominal cavity, with a wire, such as guidewire 502 or a viewing wire to allow exchange of the cannula and insertion of a larger bore access sheath over a dilator over the wire. Once the delivery tract has been established, device 10 in a compact configuration is inserted through opening 223 and advanced along the tract, through the opening in the abdominal wall and placed in the abdominal cavity. FIG. 32B illustrates device 10 having been compacted to a substantially cylindrical configuration and being fed through the opening 223. This compact configuration can be pushed along the tract without any other delivery mechanism. Optionally, a sheath or cannula 17 (shown in phantom lines in FIG. 32B) may be used for delivery of device 10 therethrough.

When the expandable member 10*em* has been completely inserted into the abdominal cavity (which can be verified by laparoscope or by other indirect visualization apparatus for a percutaneous step, or both), and optionally any buoyancy member 10*bm* or insert for a buoyancy member 10*bm* has been inserted into the expandable member 10*em*, (in those arrangements where a buoyancy member 10*bm* or portion of a buoyancy member 10*bm* is inserted after placement of expandable member 10*em* into the abdominal cavity) then cannula or sheath 17, if used, is removed from the patient and a puncture or very small incision is made in the skin 125 at a location that generally overlies a location of the abdominal wall that the surgeon wants to anchor an inferior portion of expandable member 10*em* to. The opening through which device 10 is inserted may range from about 5 mm up to about 5 cm, or up to about 7 cm. The punctures are much smaller that the opening through which the device 10 is passed.

Figure 32C:
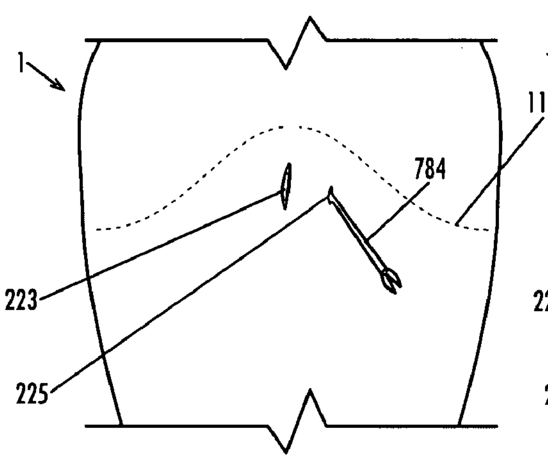
Figure 32D:
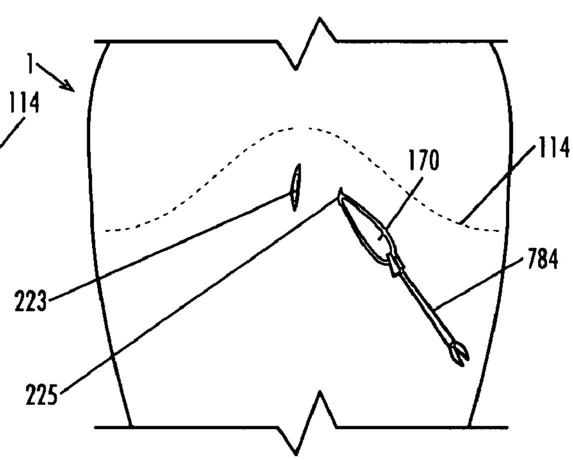

Graspers 784 or other instrument are then inserted through incision or puncture 225, as illustrated in FIG. 32C, to puncture through the subcutaneous tissues, fascia and abdominal wall. It is noted here that if the instrument that is inserted has a sharp distal end, then the instrument may be used to form the puncture 225 through the skin 125 during the same procedural step of puncturing through the subcutaneous tissues, fascia and abdominal wall, thereby eliminating the need for a separate step to form opening 225. When the distal end of the instrument enters the abdominal cavity, it is maneuvered to capture (e.g., grasp, hook, etc.) positioning loop 170. The instrument is then retracted out of the body of the patient 1 at the same time pulling loop 170 out through opening 225 as illustrated in FIG. 32D. Positioning loop 170 is pulled as described above to draw the inferior portion of expandable member 10*em* up against the interior wall surface of the abdominal wall and to generally locate it where it is to be anchored. Loop 170 is then anchored to the external surface of the abdominal wall and/or fascia and the portion of loop extending proximally from the anchoring location is cut off and removed, as described previously. One or more positioning tabs 154 may be grasped or otherwise used to help move and orient device 10 along with positioning by positioning loop 170. For example, another set of graspers 784 can be inserted through opening 223 to grasp a positioning tab 154 to assist in movements of the device 10. Also, the instrument inserted through opening 225 can first grasp or otherwise temporarily attach to one or more positioning tabs (sequentially) to perform movements of device 10 prior to engaging loop 170 and pulling it out of the abdominal cavity.

Figure 32E:
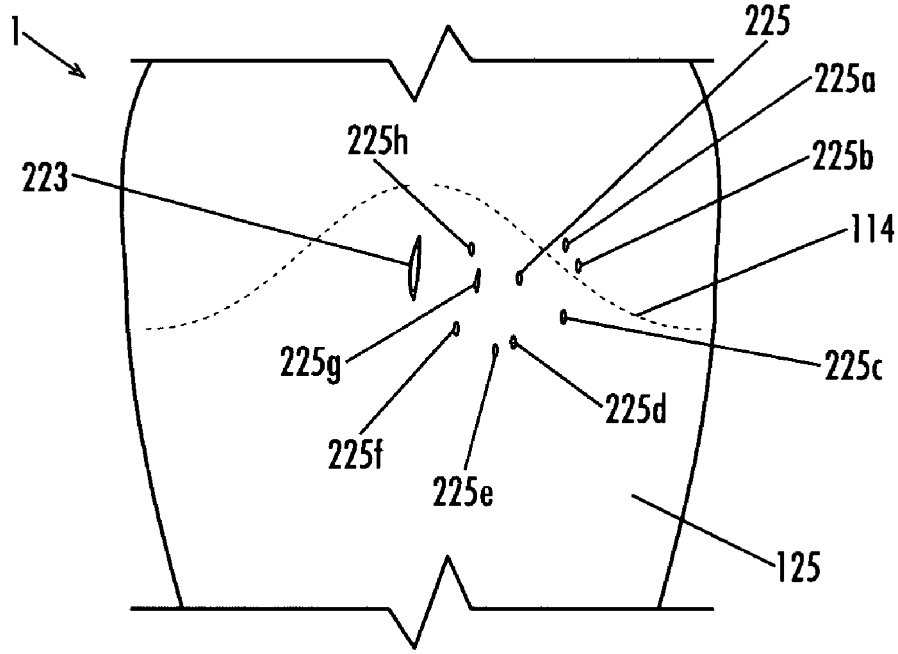

When positioning loop 170 has been anchored externally of the abdominal cavity, additional punctures or small incisions are made in order to perform the procedural steps for tying off the sutures 180 (or additional loops 170 if they are provided to substitute for sutures 180). FIG. 32E illustrates eight additional incisions or punctures 225*a*-225*h* made to carry out the anchoring procedures for the sutures 180 and/or additional loops 170, for an arrangement of sutures 180 and/or additional loops 170 shown in FIG. 27. It is noted that punctures/incisions 225*c*-225*f* in this arrangement are used as entry points for establishing two adjacent punctures each through the fascia and abdominal wall.

After completing the tying off or otherwise securing of the sutures 180 and/or additional loops 170 is completed and suture material and/or suture loop material extending proximally from the ties is removed, the incisions/punctures 225 are closed, such as by suturing. An access member 80 can be installed according to any of the techniques and in any of the locations described in co-pending application Ser. No. 11/716,985, in provisional Application Ser. No. 60/877,595, in application Ser. No. 11/407,701, or as described herein. Buoyancy member 10*bm*, if inflatable can then be inflated with a gas, and expandable member 10*em* can be inflated with a liquid. Opening 223, as well as, optionally, any additional opening that may have been created for installation of access member 80 are then closed off, such as by suturing, to complete the procedure. Alternatively, the buoyancy member 10*bm* can be integrated with/or double as an anchoring frame 600, as described in more detail below, which may allow for a smaller incision to be made in the patient, while still providing a buoyancy feature.

FIGS. 33A-33K illustrate steps that may be carried out during a procedure for implanting an expandable extra-gastric device 10 according to an embodiment of the present invention, in which the implantation may be performed through a single small opening 227 in the patient. This opening may be sized to have a length or diameter in the range of about 5 mm to about 5 cm, for example, or may have a length or diameter up to about 7 cm, for example. Prior to making the opening 227, the local area (the area of the skin 125 in and surrounding the location where the incision is to be made) may be prepared by disinfecting with alcohol and or betadine. Additionally, the patient may be given a mild sedative or may be on conscious sedation. Though not preferred, the procedure can also be carried out under general anesthesia.

Figure 33A:
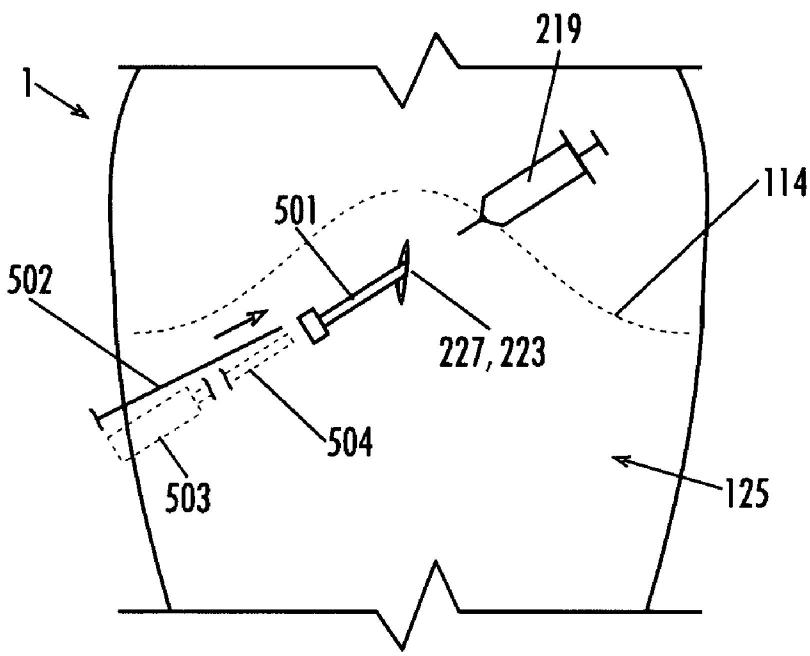
FIGS. 33A-33E illustrate steps that may be carried out during a procedure for implanting an expandable extra-gastric device according to an embodiment of the present invention.

Next a powerful local anesthetic such as marcaine (bupivicaine) or other powerful anesthetic, optionally mixed with an epinephrine or other vasoconstrictor to reduce any bleeding that might result from mild trauma can be injected into the local area through the skin 125 of the patient 1 down to the muscular layer and to infiltrate the fat layer and entire local area (the anesthetic portion of the mixture may not be needed if the procedure is performed under general anesthesia). Injection may be performed using a syringe 219, as illustrated in FIG. 33A, or other injection tool. After allowing time for the injected anesthesia to take effect, access to the abdominal cavity is gained by insertion of a needle 501 (e.g., veress needle) through the skin 125 of the patient 1, in the local area generally over the surgical target area where device 10 is to be implanted. A conventional veress needle does not have a lumen for a guidewire. By adding a small sheath outside the shaft of the veress needle apparatus, a modified veress needle is created such that a guidewire 502 can be easily introduced through the sheath. Optionally, this step may be visualized directly via a scope, as needle 501 can be provided with a scope. For example, a laparoscope 503 can be inserted into a trocar 504 (shown in phantom in FIG. 33A) having a blunt end that can be inserted which has a blunt distal end that performs effective separation of tissues as the trocar 504 and laparoscope 503 are advanced toward and into the abdominal cavity. By inserting the laparoscope 503 though this blunt-ended port/trocar, the tissues can be visualized as entry is made into the abdomen. When the surgeon sees intra-abdominal fat, the surgeon knows to stop pushing on the endoscope, or other instrument, since it is known that the abdominal cavity has been entered. Alternatively, a procedure may be done with a cannula, veress-like needle and dilator/sheath as described above. Additionally, or alternatively when scope 503 is note used, this step can optionally be visualized under fluoroscopy or other indirect visualization mechanism.

Figure 33B:
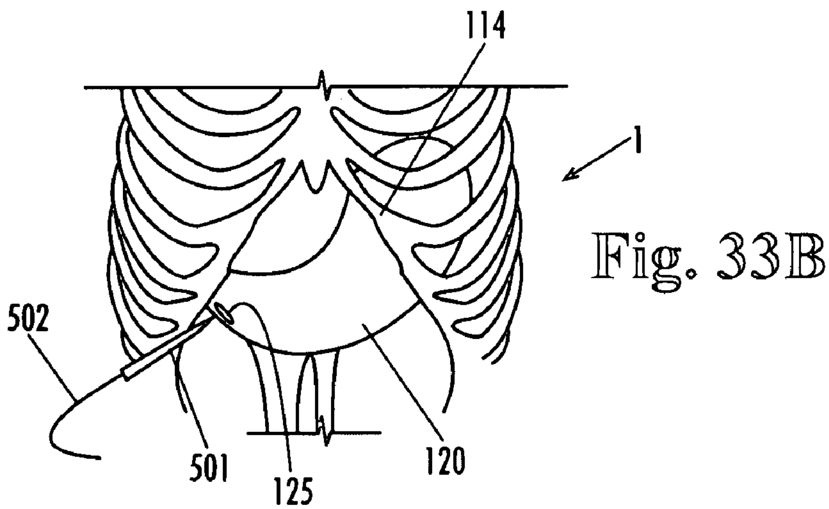

FIG. 33B is a view of the ribs and stomach 120 with an indication of the location on the surface of the skin 125 through which needle 501 and guidewire 502 can be inserted. FIG. 33B illustrates that the location of insertion can be well below the xiphoid, to the left of midline, near the palpated edge of the costal cartilages (whereas FIG. 33A indicates that the insertion can alternatively be performed slightly inferior to the lower rib line 114, as shown in the frontal schematic view of the abdominal portion of the patient 1).

Figure 33C:
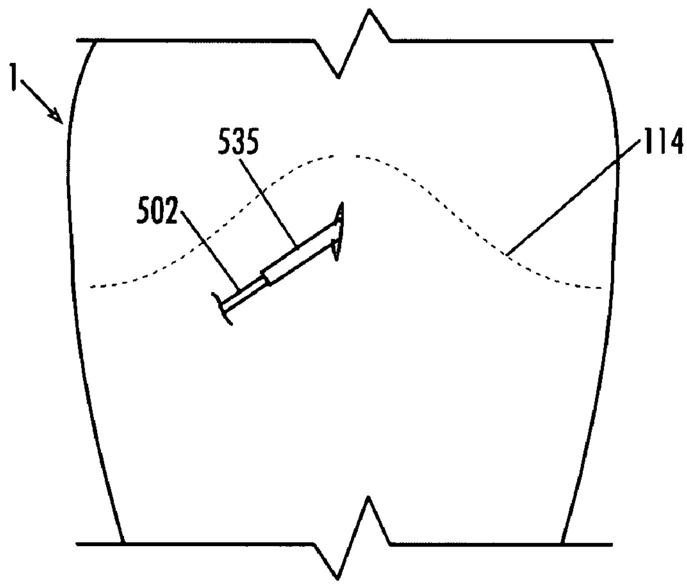

A dilator, such as an access sheath or cannula 535 having a tapering distal end portion that gradually increases in outside diameter from a distal end in a proximal direction can optionally be inserted over a guidewire 502, as illustrated in FIG. 33C, after gaining access to the abdominal cavity with a cannula and veress-like needle and exchanging needle with guidewire 502, in a manner as described above.

Figure 33D:
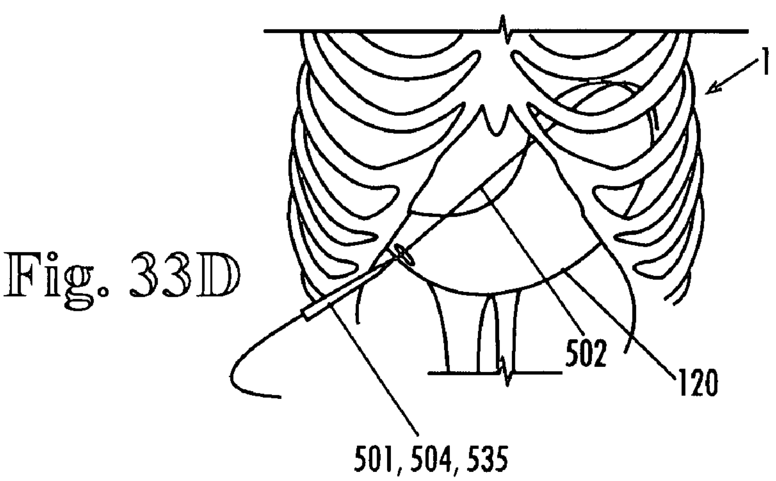
Figure 33E:
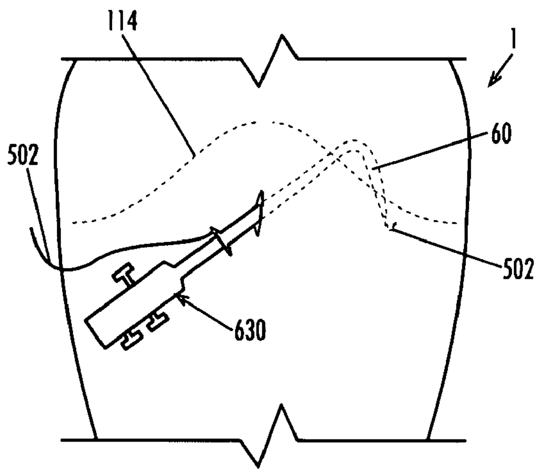

FIG. 33D illustrates the insertion of guidewire 502 to follow the contour of the caudal surface of the left hemisphere of the diaphragm as it is pushed up and around the stomach 120, as far as the spleen. The distal end of guidewire 502 may be provided in a "J" shape or other bent shape to make it more atraumatic. Alternatively, a rod may be inserted instead of guidewire 502, such as a rod that is stiffer than a guidewire and/or that has regions of varying stiffness or flexibility and/or that has an outside diameter greater than a typical guidewire and which may optionally include one or more lumens for fluid injection, suctioning, visualization, etc. Further alternatively, a flexible, steerable endoscope may be inserted in place of guidewire 502 and used as a guide rail for delivery of device 10 (as well as, optionally, other devices or instruments) thereover and into the abdominal cavity, as described in more detail in copending application Ser. No. 11/716,985. Still further alternatively, a flexible wire that is similar in construction to guidewire 502 may be inserted in place of guidewire 502, wherein the flexible wire is only slightly larger in cross-sectional diameter, and includes one or more optical fibers extending the length thereof, as described in more detail in copending application Ser. No. 11/716,985. Still further alternatively, more than one guidewire 502 or rod or flexible wire may be inserted. For example, if device 10 is designed to ride over multiple tracks on anchoring frame 600, then multiple guidewires 502 may be inserted, one for each track to ride over. Once the guidewire 502 has been placed as desired, needle 501 (if a veress needle 501 is used) is pulled off of guidewire 502 and removed. A dilator 535 can be inserted, or series of increasingly larger dilators 535 can be sequentially inserted at this point to enlarge the opening through the patient. If dilator 535 was used during the insertion of guidewire 502, then increased dilation can be performed by sequential removal and replacement of one or more larger dilators 535. The last used dilator 535 is left in position to function as a port 535.

An anchoring frame 600 and an anchoring frame delivery tool 630 on which anchoring frame 600 is mounted (in any of the manners described in application Ser. No. 11/716,985 are advanced over guidewire 502 and through dilator/port 535 (see FIG. 33E) after which anchoring frame delivery tool 630 is operated to deliver anchoring frame 600 into the target position along the abdominal wall, where it is anchored there. Prior to anchoring, the surgeon will check to ensure that no bowel, omentum or other tissue is located between the anchoring frame 600/tool 630 and the abdominal wall 127. Optionally, instrument 630 may be provided with a scope, either flexible or rigid to facilitate direct visualization of delivery and anchoring of the anchoring frame 600. Alternatively, indirect visualization, such as fluoroscopy, electromagnetic visualization mechanisms, or other indirect visualization systems can be used. Further alternatively, both direct and indirect visualization may be used. Anchoring may be performed by a variety of different attachment means, including, but not limited to sutures, staples, adhesives, tacks, needles, or combinations thereof.

Figure 33F:
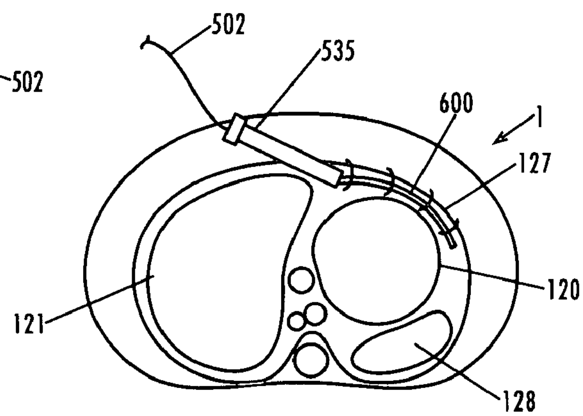
FIG. 33F illustrates a sectional view of a patient (viewed from the feet of the patient) that shows the anchoring of an anchoring frame to the abdominal wall.
Figure 33G:
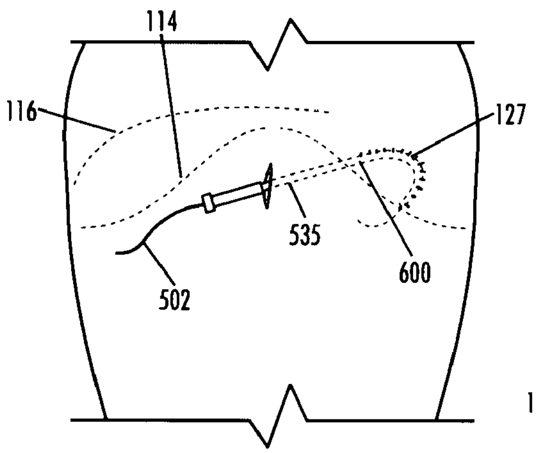
FIG. 33G is a schematic illustration from a frontal view perspective, showing an anchoring frame anchored in place against the anterior abdominal wall.

After anchoring the anchoring frame 600 to the abdominal wall 127, anchoring frame delivery tool is then removed from dilator/cannula 535 and off guidewire 502. FIG. 33F illustrates a sectional view of the patient 1 (viewed from the feet of the patient) that shows the anchoring of anchoring frame 600 to the abdominal wall 127, with the anchoring frame delivery tool 630 having been removed. FIG. 33G is a schematic illustration from a frontal view perspective, showing the anchoring frame 600 anchored in place against the anterior abdominal wall 127, as also shown in the sectional view of FIG. 33F.

Figure 33H:
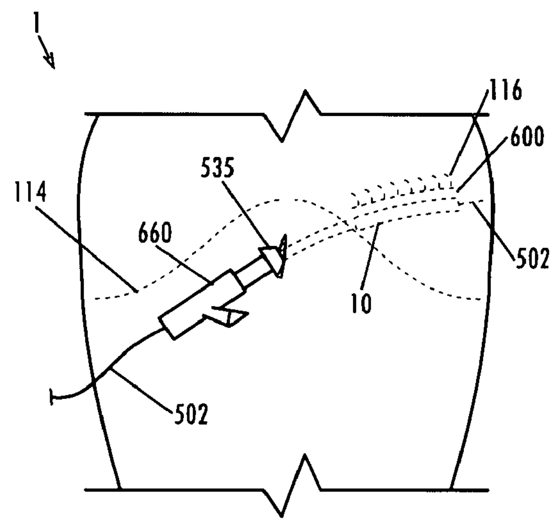
FIG. 33H illustrates advancement of a device, using a device deployment tool having already been preloaded with the device in a collapsed or compressed configuration over a guidewire.

Once anchoring frame has been anchored to the target location, as illustrated in FIGS. 33F and 33G, a device deployment tool 660 having already been preloaded with a device 10 in a collapsed or compressed configuration, is next advanced over the guidewire 502 and over anchoring frame 600 in any of the manners described in application Ser. No. 11/716,985 or herein, and as illustrated in FIG. 33H. Positioning of the device 10 can be monitored during this delivery using fluoroscopy, X-ray, CT or MRI visualization guidance, for example, or simply via direct visualization with an endoscope, such as a flexible endoscope inserted through sheath/cannula 535, for example, or extended through deployment tool 600, or optionally, though not preferred, through another opening provided through the patient's skin and into the abdominal cavity. Device 10 is advanced to the end of anchoring frame where it automatically locks into position there. Insertion of any of the anchoring frame 600 and anchoring frame delivery tool, device 10 and device delivery tool, and/or any of the instruments and/or devices used to access the abdominal cavity are typically performed without insufflation, but may be assisted by what is referred to "mini-insufflation" where the entire abdominal cavity is not insufflated, as in the typical insufflation procedure, but small bursts of insufflation gas are intermittently inputted to facilitate separation of anatomical structures to help develop the insertion path. Thus, a small burst could be associated with a small advancement of an instrument or device, followed by another small burst to help advance the instrument or device incrementally, and so forth, until the target location has been reached. Alternatively, impulses of liquid (e.g., saline) can be sprayed to accomplish the same task (e.g., to clear and path and provide enhanced visibility). Further alternatively, although not preferred, traditional insufflation can be performed. This would typically only be done when the less preferred option of using general anesthesia is also performed.

Figure 33I:
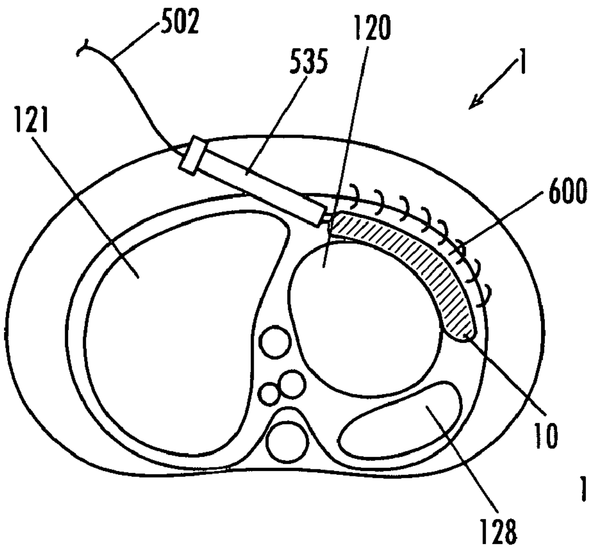
FIG. 33I shows a sectional illustration of a device having been locked into position on an anchoring frame.
Figure 33K:
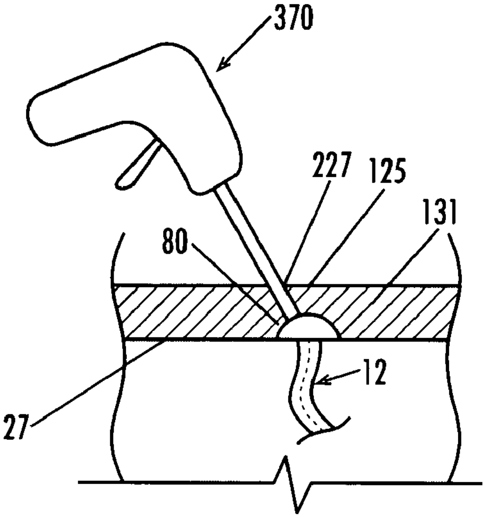
FIG. 33K shows an adjustment member being anchored subcutaneously, to the external surface of the abdominal wall.

FIG. 33I shows a sectional illustration of device 10 having been locked into position on anchoring frame 600, with device delivery tool 660 having been removed. At this stage, when the surgeon is satisfied that device 10 has been properly positioned and locked to anchoring frame 600, cannula/port 535 and guidewire 502 are both removed. At least one conduit 12 will remain extending will remain extending from device 10, proximally out through the opening 227 for inflation of expandable member 10*em* and, optionally one or more buoyancy members 10*bm* when one or more inflatable buoyancy members are provided. The one or more conduits 12 can then be used to inflate the one or more buoyancy members 10*bm* with gas (when buoyancy member 10*bm* is of an inflatable variety) and to inflate expandable member 10*em* with liquid. Further alternatively, one or more conduits may extend through the opening 227 to allow a wire, strut, tube or other structural support member to be inserted to support either buoyancy member 10*bm* or expandable member 10*em*, or to insert a buoyancy member 10*bm* into expandable member 10*em*.

Optionally, expandable member 10*em* may be inflated at this stage to test the amount of displacement and positioning of the device 10 when in an expanded configuration, which may help to determine whether device 10 will perform as intended. One method of testing in this manner is with the use of an intra-gastric sizing device 310 (e.g. an intra-gastric balloon catheter) in a manner as described in application Ser. No. 11/407,701 and application Ser. No. 11/716,985. Additionally, or alternatively, testing may be performed by visually observing the effects of expansion, such as by inputting radiopaque fluid into the stomach 120, and/or by observing the expansion of the device when it is provided with one or more radiopaque indicators. Visualization, in such instances may be performed fluoroscopically or with other X-ray visualization, for example.

Figure 33J:
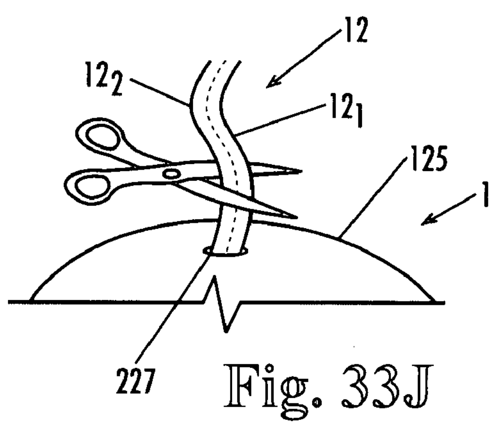
FIG. 33J shows trimming of conduit(s) to an appropriate length for connection with an adjustment member.

At this time, any extending conduit(s) 12 can be either clamped off to maintain the pressures within expandable member 10*em* (and optionally buoyancy member 10*bm*), or the pressures can be released, thereby allowing expandable members 10*em* (and optionally, buoyancy member 10*bm*) to at least partially deflate. It is easier procedurally to release the pressures and so this is typically done. However, the surgeon may choose to clamp off the conduit(s) to maintain at least partial pressure in at least the expandable member 10*em* to help maintain it in the observed position/orientation. In any case, conduit(s) 12 is/are next trimmed to an appropriate length for connection with an adjustment member 80, as illustrated in FIG. 33J.

Conduit(s) 12 are connected to a mating connector on adjustment member 80 or to a deployment tool 370 configured to mate conduit 12 with adjustment member 80, and, after connection of conduit 12 to adjustment member 80, adjustment member deployment tool 370 is then used to anchor adjustment member 80 to the patient. Adjustment member 80 can be anchored using anchoring members that may be made as any of a number of different configurations, including, but not limited to: protruding pins, protruding staples, moly bolt, snap fit with portion placed against interior abdominal wall surface; extendable hooks actuated upon torquing a portion of the adjustment member 80 relative to another portion, etc. By advancing deployment tool 370 into the patient, the portion of conduit that had extended from the patient 1 is pushed back into the patient, until the adjustment member is positioned in the target location where it is intended to be anchored. This positioning can be verified using any of the previously described visualization techniques, or can be performed blindly, with feedback from palpitation, for example. In the example shown in FIG. 33K, adjustment member 80 is anchored subcutaneously, to the external surface of the abdominal wall 127. As has been disclosed previously in applications relied upon for priority and incorporated herein, adjustment member 80 can alternatively be anchored subcutaneously, to an inner layer of the skin for example, or otherwise in the fat layer 131 without being anchored directly to the abdominal wall 127.

Once adjustment member 80 has been anchored in the desired location, deployment tool 370 is withdrawn and expandable member 10*em* is inflated with liquid to expand it to the desired size or pressure, and buoyancy member 10*bm*, if it is an inflatable variation can be inflated with gas to a desired pressure. This can be a re-inflation step if the expandable member 10*em* (and optionally the buoyancy member 10*b* had been previously inflated for testing and then deflated, or partially deflated. In this way, the patient can begin to experience beneficial weight loss from the effects of device 10 on the stomach 120 beginning immediately after completion of the procedure, unlike current procedures, which typically require around six weeks before a return visit to "complete" the procedure to make it effective in helping weight loss. The same type or types of monitoring can be used here, as described in application Ser. No. 11/716,985, to provide feedback as to when the expandable member 10*em* and/or buoyancy member 10*bm* has been expanded by the desired amount or pressure. Alternatively, expandable member may be left in an unexpanded or partially expanded configuration, with the patient being allowed to heal and then return to have the expandable members 10*em* fully inflated. Further alternatively, device 10 may be implanted in combination with a constricting band, such as the LAPBAND™ or similar implant to improve results from such constricting band, or to make weight loss efficacious where prior implantation of such a constricting band has not been efficacious. For example, a constricting band generally useful for restricting the amount of solid food ingested by the patient 1. However, a patient 1 may "cheat" the effectiveness of a constricting band approach by drinking high caloric liquids, for example. For example, a patient could drink a thirty-two ounce milkshake and this would pass right through the constriction established by the constricting band. However, with device 10 implanted and expanded as described, the stomach is preventing from expanding, even by high caloric liquids.

Once the surgeon is satisfied that the expandable member 10*em* has been expanded by the desired amount and, optionally, the buoyancy member has been inflated to the desired pressure, or, alternatively, if the expandable member 10*em* is to be left in a contracted (unexpanded or partially expanded) state, the patient is closed, including, suturing the skin 125 at the site of the opening 227.

Any of the variations of the procedural steps described above may be executed under indirect visualization, such as fluoroscopic visualization, 3-dimensional navigation or other CT/MRI guidance, ore thee dimensional RF or electromagnetic visualization (e.g., using pre-existing or real-time data sets from MRI, cat scan, three-dimensional ultrasound or other three-dimensional data set). Further alternatively or additionally, any of these procedural steps may be directly visualized using a scope such as a laparoscope or other flexible or rigid endoscope. A scope may also be integrated into a tool used to perform one or more of these steps.

All tools referenced in the above procedure may include lumens to permit insertion of other tools and/or devices therethrough, including, but not limited to: endoscopes, wires, etc. and/or to allow delivery of suction, irrigation, and/or other substances. Alternatively to mounting the adjustment member 80 to conduit 12 in any of the manners described above, adjustment member may be pre-attached or integral with conduit 12.

No tissues around the stomach area are required to be dissected when performing the procedures described above with regard to FIGS. 33A-33K. This also applies to procedures described with regard to FIGS. 32A-32E. This is a major factor in why general anesthesia is not required to perform the procedures, why insufflation is not required, and consequently why these procedures can be performed in a physician's exam room and are not required to be performed in an operating room Further, with regard to the procedures described with regard to FIGS. 33A-33K, no tissue dissection is required other than that to perform the single entry location through the skin and abdominal wall. The single access port procedures make this a very minimally invasive procedure. Also, in all procedures described, no stapling or attachment to the stomach is required. That is, the stomach 120 is not attached to device 10 in any way and is free to move relative to device 10 and to the other contents of the abdominal cavity, except for the constraints provided by the space occupied by device 10. This greatly minimizes, if not eliminates problems of erosion experienced by prior art solutions that do attach to the stomach or pierce through the stomach wall, as force concentrations, such as shear force concentration are not built up between device 10 and the stomach 120.

Figure 34:
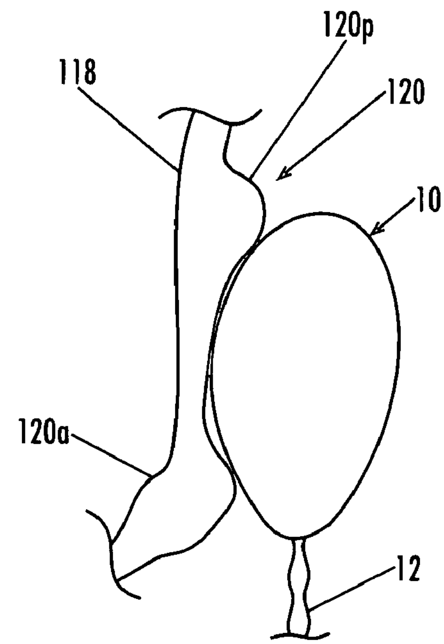
FIG. 34 illustrates restriction of the stomach from expanding to its post-prandial, expanded configuration.

FIG. 34 illustrates restriction of the stomach 120 from expanding to its post-prandial, expanded configuration by implantation of device 10. As can be seen the fundus is substantially restricted from where it would otherwise normally expand and the stomach is restrained to a shape resembling a tube, not dissimilar to a shape resulting from a sleeve gastrectomy, but, of course achieved in a very minimally invasive manner. At least a portion of the antrum 120*a* is left unrestrained to allow it to perform its normal functions, such as contractions to move food into the small intestines by ejecting it from the stomach 120 with muscular contractions. Additionally, a small pouch 120*p* may be left at the superior end portion of the stomach 120 that provides a small capacitance or chamber for receiving food and then signaling the patient that it is full when this small chamber is filled, similar to a functionality provided by a banding procedure, such as the LAPBAND™ procedure, for example. Under conditions where the stomach is empty (e.g., has substantially no food in it), device 10 may not exert any additional pressure (or only minimal additional pressure) to the stomach 120. That is the stomach 120 will experience substantially only "normal" abdominal pressures (i.e., close to the pressures that it would experience if there were no implant in the abdominal cavity). Thus, significant forces are only generated between device 10 and the stomach 120 when the patient eats.

Figure 35A:
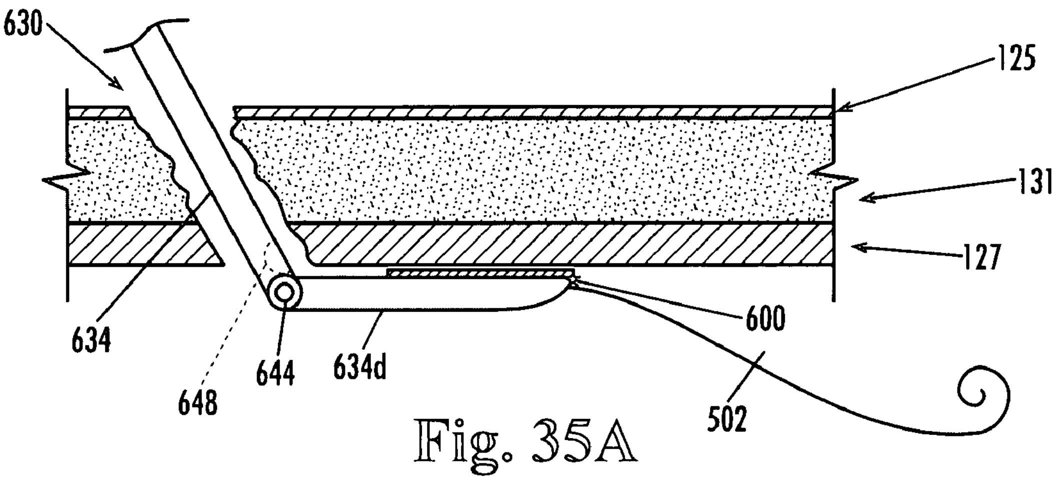
FIGS. 35A-35D illustrate and instrument and method for anchoring an anchoring frame to an internal abdominal structure.
Figure 35B:
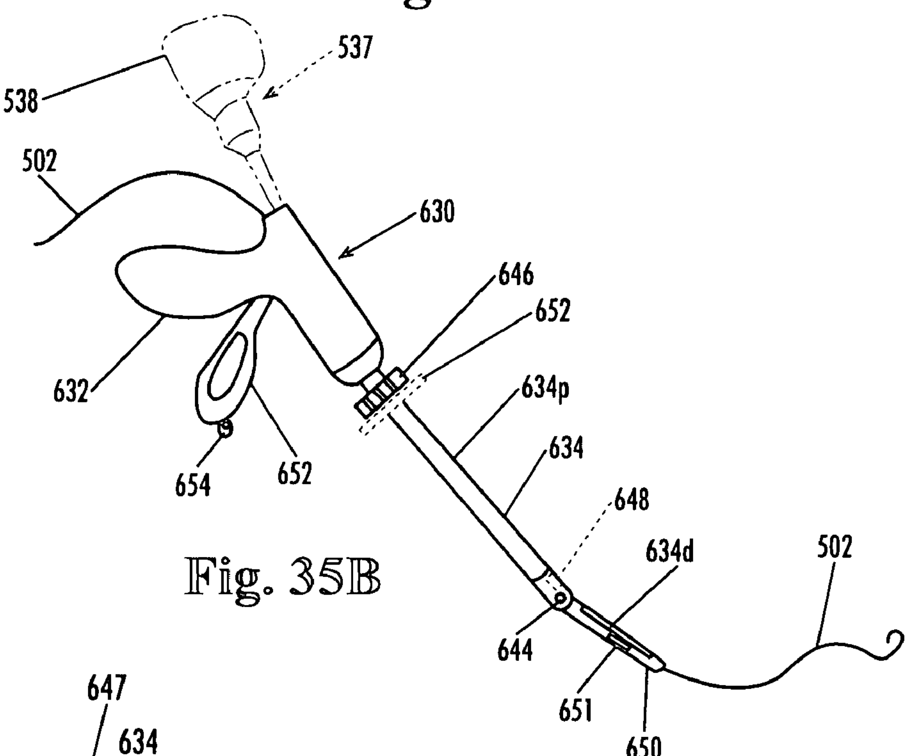

With regard to procedural embodiments involving the anchoring of anchoring frame 600 to an internal abdominal structure, FIGS. 35A-35D illustrate an alternative instrument and method to that described in application Ser. No. 11/716,985, e.g., see FIG. 18B and the description thereof in application Ser. No. 11/716,985. FIG. 35B illustrates a partial view of an anchoring frame deployment tool 630, showing a distal portion of shaft 634 with anchoring frame 600 mounted to distal end portion 634*d*.

Shaft 634 articulates, via one or more articulating joints 644 to move distal end portion 634*d* angularly relative to a portion of shaft 634 proximal of distal end portion 634*d*. An articulation actuator 646 (see FIG. 35B) is provided on or near handle 632 of tool 600 for operation by a user to control the articulation of distal portion 634*d* of shaft 634. In the example shown, articulation actuator 646 is a rotatable wheel that is rotatable in a first direction to articulate distal portion 634*d* in a first angular direction about joint 644, while rotation of actuator 646 in the opposite direction articulates distal portion 634*d* in the opposite direction. Articulation actuator 646 and/or articulation joint 644 provide frictional resistance, so that when actuator 646 is not being rotated, distal portion 634*d* is maintained in its orientation relative to proximal portion 634*p*. Alternatively, the straight shaft portion 6349 and articulation feature may be replaced by a curved shaft having no articulating feature 644.

Distal portion 634*d* includes a recess, cavity or slot 650 configured to receive anchoring frame 600 therein. Thus, recess, cavity or slot 650 is shaped and dimensioned to receive anchoring frame 600 therein and to confine anchoring frame 600 from movements axially with respect to the longitudinal axis of distal portion 634*d*. Frame 600 may be received in recess, cavity or slot 650 by friction fit and/or a releasable clamping mechanism 651 maybe optionally provided on opposite sides of slot, recess or cavity 650 for releasably clamping frame 600 wherein it is received therein, with clamping and releasing motions being controlled by clamp actuator 653.

In use, after insertion and placement of guidewire 502, such as in a procedure as described above, deployment tool 630 is passed over guidewire 502, with the proximal end of guidewire first being inserted into the distal end of shaft 634, through shaft 634 and handle 632 and proximally out of handle 632, as illustrated in FIG. 35B. By insertion of tool 630 into the abdominal cavity, the abdominal wall (e.g., the anterior abdominal wall can be accessed. This portion of the procedure, as well as other steps described below may be indirectly visualized using fluoroscopy and/or any of the other indirect visualization methods described above. Additionally, or alternatively, tool 630 may be configured to receive an endoscope 537 (shown in phantom in FIG. 35B) that can be used for direct viewing of the procedure. Thus, endoscope 537 can be used to directly view the placement of anchoring frame 600. A video camera 538 may be provided on endoscope 537 so as to monitor the visualization on a screen, or, optionally, viewing may be performed directly through an ocular.

A window or opening 648 may be provided proximally of articulating joint 644 to enable viewing through the distal end of endoscope 537 that is positioned in shaft 634 at the location of opening/window 648 when endoscope 537 is inserted into tool 630. Window/opening 648 may be an opening (e.g., cutout), or may be a window, e.g., a cutout that is sealed over with a transparent material.

Figure 35C:
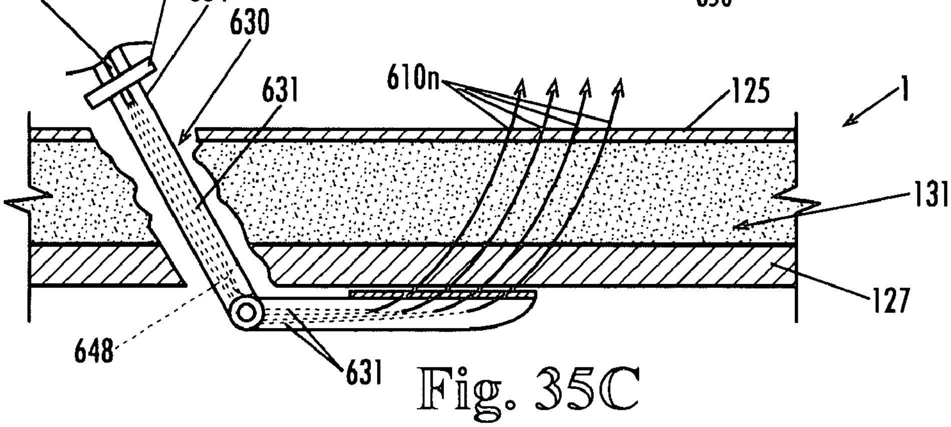
Figure 35D:
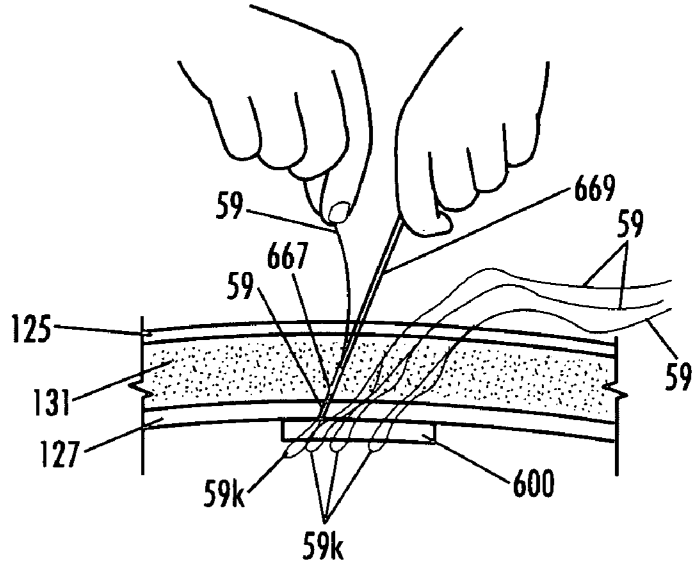

Visualization, whether indirect, direct, or indirect and direct, is performed to ensure that there is no tissue located between the anchoring site (e.g., anterior abdominal wall 127) and anchoring frame 600 (see FIG. 35A) prior to anchoring the frame 600 to the anchoring site. Once it has been visually confirmed that there is no tissue intervening between frame 600 and the anchoring site, actuator 646 is manipulated to rotate distal portion 634*d* up against the anchoring site, thereby contacting surface a contact surface of frame 600 to the anchoring site. Anchors 610 in the form of elongated flexible needles 610*n* having sutures 59 connected thereto and extending therefrom are next deployed through openings in the anchoring frame 600, through the internal abdominal structure to be anchored to (e.g., the anterior abdominal wall 127 in this case) through the subcutaneous fat layer 131 and the skin 125 and therefore out of the patient 1, as illustrated in FIG. 35C. This deployment may be actuated by an actuator 647. For example, actuator 647 may be connected to one or more push rods 631 that abut against ends of needles 610*n* to provide a driving force to push needles 610*n* through the internal abdominal anchoring site and other tissues noted above. Push rod(s) 631 may be flexible, but have sufficient column strength so that it/they do not buckle under the compression put on them by actuator 647 during deployment, but rather transfer the compression forces to needles 610*n* to move them out of the tool 630 (distal end portion 634*d*). Actuator 647 may be connected about shaft 634 for relative sliding with respect thereto via slot 647*s*. Needles 610*n* can be very thin, e.g., like acupuncture needles, and also have sufficient column strength to pass through the structures described without buckling.

Needles 610*n* are then disengaged from the needle delivery mechanism (e.g., push rods 631). Needles 601*n* can be directly attached to sutures that reside within the channels of the delivery device (not shown). The back end of the sutures can be looped and held on a hook attached to a handle on the device to allow retraction of the needles into the device if initial deployment was not satisfactory. This hook mechanism can be actuated to release the sutures via a button on the handle when the needle locations are determined to be acceptable, allowing the suture/needle units to be pulled by the operation outward until they engage the anchoring platform. There are many other alternative mechanisms, widely known in the art, to grasp and release a thread like a suture, including mechanisms that cut the sutures from a fixed location, mechanisms that open up a clamp that was holding the sutures in a fixed location, mechanisms for releasing a lock on a spool where sutures are wrapped and initially retained within the deployment device, etc.

Next, the surgeon, pulls the needles 610*n* the rest of the way out of the patient 1, and continues this retraction until knots or other anchors (e.g., T-bars, or the like) at the ends of sutures 59 are stopped against anchoring frame 600 Alternatively, sutures 59 may be looped 59*k* through anchoring frame 600, so that adjacent pairs of needles 610*n* are connected to opposite ends of a looped suture 59. The needles 610*n* are removed from the sutures 59, leaving organized sutures precisely delivered through anchoring frame and the internal anchoring structure, precisely deliver through key strategic locations through anchoring frame 600 designed to optimally secure the anchoring frame 600 to the internal abdominal structure. Alternative embodiments may replace the sutures with other flexible members. For example, polypropylene mesh ribbons may be substituted. Further alternatively, a combination of sutures and mesh ribbons may be used, where the flexible member 59 begins as a suture where it connects with the needle, and transitions into a ribbon. An advantage of a combination such as this is that the sutures are more easily delivered out through the abdominal wall, while the ribbons provide potentially better fixation to the abdominal wall.

Sutures 59 may be fixed externally of the abdominal cavity by tying them down, according to a procedure similar to that described above with regard to FIGS. 27-28 (e.g., by tying two suture ends together to form a loop), or a knot pusher tool 669 can be used to slide a self-locking clip 667 that can be advanced distally over suture 59 toward the abdominal wall 127, but which is configured to prevent backsliding in a proximal direction, over suture 59 and against the fascia or abdominal wall, or as close thereto as possible as there may be a small amount of fat 131 clamped between clip 667 and the fascia/abdominal wall 127, thereby securing a portion of anchoring frame 600 to the internal abdominal structure (in this case, the inner surface of the anterior abdominal wall 127) by the tension generated in suture 59. The distal end of knot pusher tool 669 may have a sharp edge portion that can be used to cut off the portion of suture 59 that extends proximally from the location of clip 667 in its fully advanced position. This cut off portion of the suture and the knot pusher tool 669 are then removed from the patient. Each remaining suture 59 is thereafter sequentially tied/clipped down to securely anchor the entire anchoring frame, thereby forming an array of distributed anchoring forces distributed over the anchoring frame 600.

Figure 35E:
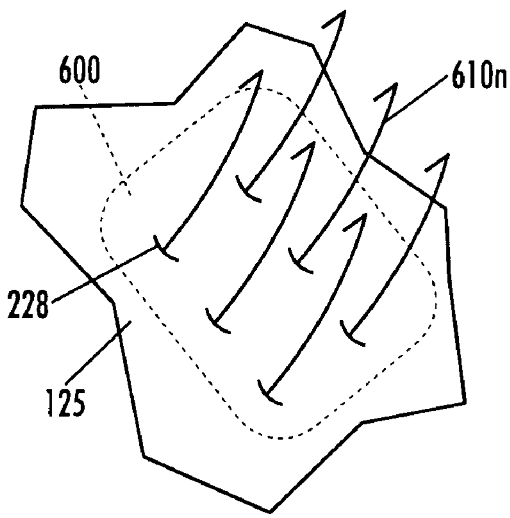
FIG. 35E illustrates a patient's skin with needles protruding therethrough.
Figure 35F:
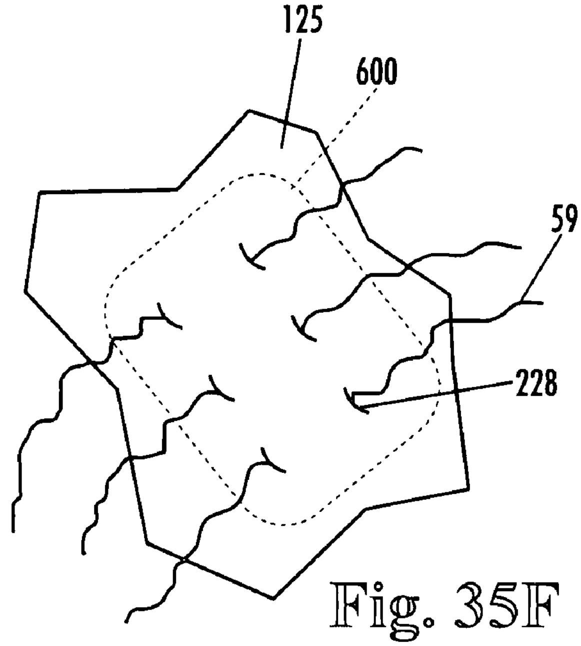
FIG. 35F illustrates sutures extending from openings through the skin of the patient after removal of the needles shown in FIG. 35E.

FIG. 35E is an illustration of the patient's skin 125 with needles 610*n* protruding through openings 228 formed by piercing the needles 610*n* therethrough during performance of the step described with regard to FIG. 26C above. Anchoring frame 600, which has been contacted against the anterior internal abdominal wall surface, is shown in phantom. FIG. 35F illustrates sutures 509 extending from openings 228 through the skin after removal of needles 610*n*.

Figure 35G:
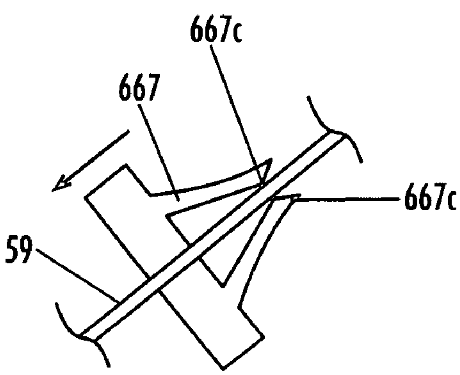
FIG. 35G illustrates one embodiment of a suture lock or clip installed over a suture.
Figure 35H:
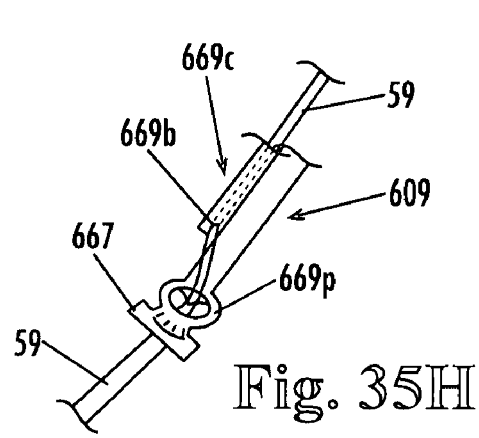
FIG. 35H illustrates a distal end portion or working end of a knot pusher tool being used to lock down a clip over a suture.

FIG. 35G illustrates one embodiment of a suture lock or clip 667 installed over a suture 59. Clip 667 can be freely advanced over suture 59 in the direction indicated by the arrow, but prevents sliding in the opposite direction, as teeth or cammed surfaces 667*t* bite into the suture 59 if clip is attempted to be slid in the opposite direction, thereby preventing backsliding of clip 667. FIG. 35H illustrates a distal end portion or working end of knot pusher tool 669 being used to lock down a clip 667 in a manner as described above. Tool 669 includes a distal end pusher 669*p* configured to interface with a proximal surface of clip 667 so as to form a secure engagement therewith as force is applied therethrough to push clip 667 along suture 59. Tool 669 further includes a cutter portion 669*c* proximal of pusher 669*p* and through which suture is threaded. Cutter portion 669*c* includes a sharp edge or blade 669*b* that can be actuated from a proximal end portion of tool 669 once clip has been advanced over suture 59 as far as it is going to be advance to engage the fascia, abdominal wall, or fat near the fascia/abdominal wall. Actuation of cutter edge 669*b* cuts through the suture 59 leaving a short proximal tail that extends from clip 667 by a length about equal to the distance between pusher 669*p* and cutting edge 669*b*.

Figure 35I:
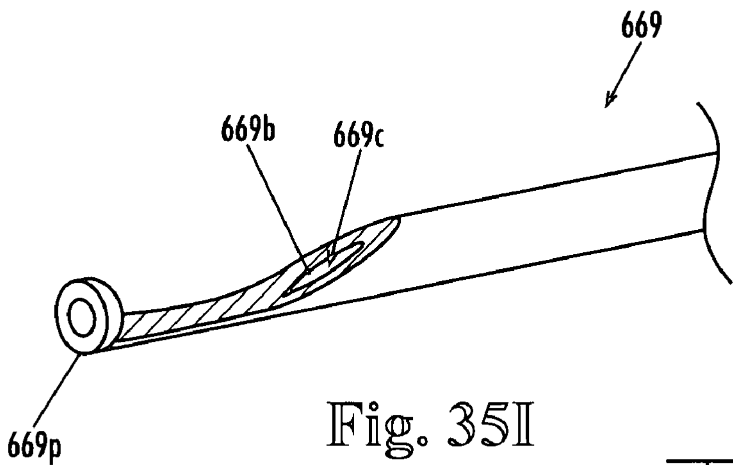
FIG. 35I illustrates another embodiment of a knot pusher tool.

FIG. 35I illustrates another embodiment of a knot pusher tool 669 wherein the cutter portion 669*c* is axially aligned with pusher 669*p*. Thus suture 59 extend straight through the opening in pusher 669*p* and the opening in cuter portion 669*c* out though the central lumen of tool 669. Cutter portion includes a V-shaped sharpened edge 669*b* that may be beveled on the underside, so that suture 59 freely passes over the edge 669*b* as tool 669 is being advanced distally over the suture 59. However, as soon as tool 669 is retracted proximally with respect to suture 59, the beveled side of sharpened edge 669*b* begins to bite into suture 59 and forces it into the wedge-shape toward the apex of the V-shaped edge, thereby cutting the suture and leaving a tail having a length about equal to the distance between pusher 669*p* and the apex of the V-shaped cutting edge 669*b*.

Figure 36A:
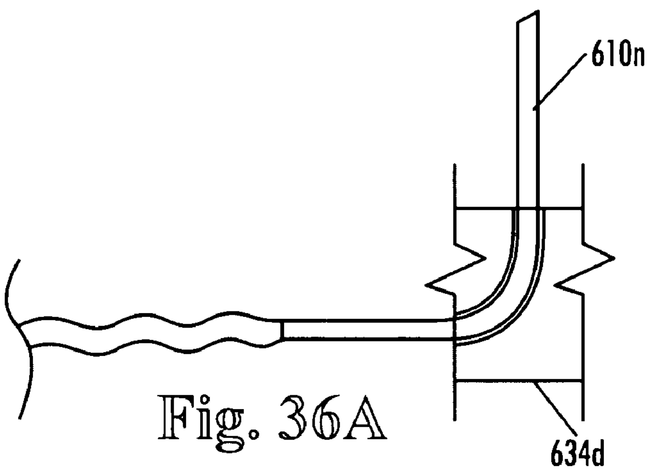
FIG. 36A illustrates an alternative arrangement of needle and anchoring member that can be used for anchoring an anchoring frame.

FIGS. 36A illustrates an alternative arrangement of needle 610*n* and anchoring member 59 that can be used for anchoring an anchoring frame 600 in a manner like that described above with regard to FIGS. 35A-35I with variations described hereafter. In order to deploy needles to extend out through the abdomen of a patient 1, needles 610*n* may need to be long enough to extend through the abdominal wall of an obese patient, e.g., on the order of about five inches to about eight inches, typically about seven inches. Accordingly as already noted, needles 610*n* typically require the ability to be bent without plastically deforming as they are redirected from extending in a direction along a length of a deployment instrument, to a direction substantially perpendicular thereto, to deliver needles 610*n* through the anchoring frame 600, the abdominal wall 127 and out of the patient 1. FIG. 36A shows only a portion of distal end portion 634*d* that contains a radiused portion of channel 634*c* having a controlled radius to redirect needle 610*n* through the anchoring frame 600 (not shown in FIG. 36A, for simplicity), without plastically deforming the needle 610*n*. For example, needle 610*n* may be formed of superelastic material, such as nickel-titanium alloy. Needle 610*n* may optionally include derailing feature 610*p* at or near the end opposite the sharp, leading end, that connects to the anchoring member and that, when contacting the radiused portion, does not enter the radiused portion, but "kicks out" sideways so that the anchoring portion 59 does not need to be drawn through the radiused portion. Alternatively, the anchoring portion 59 can be drawn through the radiused portion, following the needle 610*n*. The device that deploys the needles may have a mechanism for pushing the needles from a proximally locating starting position, where the starting positions of the needle tips are near the locations where they exit the device, and the needles, being quite long extend proximally along (within) the shaft of the device such that the proximal end of the needles having a starting location with the device shaft that is outside of the abdominal cavity. The mechanism pushes the needles along the device shaft to extend the needles outward to pierce through the abdominal wall. The needles have sufficient length so that they are still being pushed by the mechanism as the needle tips exit the skin of the patient. Once the needles are fully advanced, they are disengaged from the mechanical pushing mechanism. The user can then continue to draw the needles out of the patient and thereby draw the trailing suture./ribbon out through the abdominal wall. The mechanism for pushing the needles can be mechanical or pneumatic in nature, powered by energy inputted by the user, or by stored in energy in the mechanism, such as springs or compressed gas.

Needle 610*n* may be alternatively connected to a mesh ribbon 59*r*, as shown in FIG. 36A, rather than a suture 59. Mesh ribbon 59*r* may be made from polypropylene mesh, or the like, and may be made to be more durable than a suture 59, both during assembly of the deployment device, as well as during deployment of the needles 610*n* and ribbons 59*r*. Also ribbon 59*r* has lots of surface area, compared to a suture 59, any portion of which can be easily engaged by barbs. In at least one embodiment, ribbon 59*r* includes directional barbs 59*b* that point away from the end of the ribbon 59*r* being pulled through the skin of the patient 1. When ribbon 59*r* has been pulled sufficiently through the abdominal wall to draw anchoring frame 600 against the inner surface of the abdominal wall, release of tension on ribbon 59*r* causes barbs 59*b* outside of the abdominal wall 127 and nearest to the outer surface of the abdominal wall 127/fascia to catch against the abdominal wall 127/fascia, thereby piercing into the abdominal wall 127/fascia and flaring out radially somewhat, as illustrated in FIG. 36H. This securely anchors ribbon 59*r*, preventing it from backsliding through the abdominal wall, and maintaining tension on anchoring frame 600 to hold it against the abdominal wall. The barbs on the ribbons can be large features, or so small as to be a microscopic texture that achieves the same effect. The barbs can be utilized to engage into the tissue, or, alternatively, the large barbs can be used to lock into an externally loaded, washer-like implant that ratchets down the barbs and locks in place about the fascia, thereby preventing the ribbon and implant form moving away from the fascia. When deploying needles 610*n* having mesh ribbons 610*r* connected thereto through the internal abdominal structure to be anchored to (e.g., the anterior abdominal wall 127 in this case) through the fascia and subcutaneous fat layer 131 and the skin 125 and therefore out of the patient 1, after removing needles 610*n* from the mesh ribbon 59*r* portions extending out of the abdomen, mesh ribbons can be anchored externally of the abdominal cavity by tying them down, according to a procedure similar to that described above with regard to FIGS. 27-28 (e.g., by tying two mesh ribbons 59*r* together to form a loop, or suture(s) can be used to tie the ribbons 59*r* to the fascia wall, optionally using device aids to place sutures, or a knot pusher tool 669 can be used to slide a speed nut 667 that can be advanced distally over ribbon 59*r* toward the abdominal wall 127, but which is configured to prevent backsliding in a proximal direction, over ribbon 59*r*, similar to the method described with regard to FIGS. 35G-35I above. Speed nut 667 can be advanced against the fascia or abdominal wall, or as close thereto as possible as there may be a small amount of fat 131 clamped between speed nut 667 and the fascia/abdominal wall 127, thereby securing a portion of anchoring frame 600 to the internal abdominal structure (in this case, the inner surface of the anterior abdominal wall 127) by the tension generated in ribbon 59*r*.

Figure 36B:
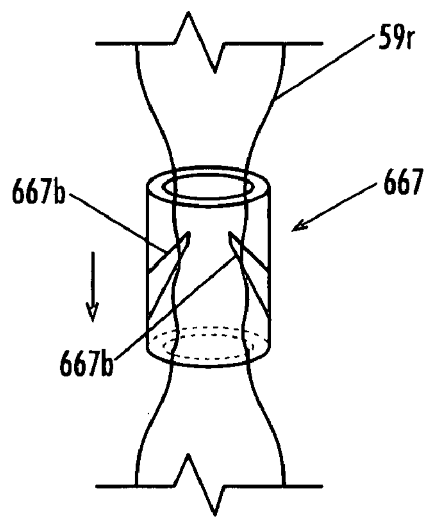
FIG. 36B illustrates an embodiment of a speed nut.
Figure 36C:
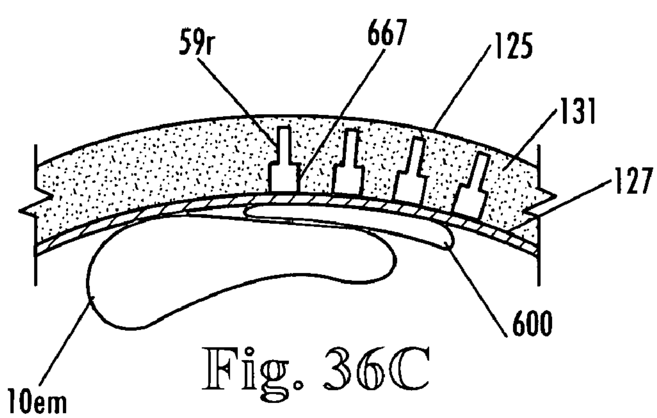
FIG. 36C illustrates a plurality of ribbons having been anchored by fixing speed nuts against the external surface of the abdominal wall/fascia.

FIG. 36B illustrates an embodiment of speed nut 667. Speed nut 667 may be made of metal, such as stainless steel, nickel-titanium alloy or the like, or rigid polymer, either resorbable or non-resorbable. Speed nut 667 may also be formed from a flexible plastic as long as the gripping features, such as barbs, spears or other gripping features are strong enough to maintain attachment of speed nut 667 to the ribbon or suture it is anchored to. Speed nut 667 is provided with barbs 667*b*, so that speed nut 667 can be passed freely over ribbon 59*r* in the direction of the arrow shown (e.g., toward the abdominal wall), but if an attempt is made to slide speed nut 667 in the opposite direction relative to ribbon 59*r*, barbs 667*b* engage in the ribbon 59*r*, through the holes already existing in the mesh ribbon, or by creating holes in a non-mesh ribbon, thereby stopping the motion and locking speed nut 667 relative to ribbon 59*r* with respect to motion in the reverse direction of the arrow shown. Such barbs can be designed as shown, or may have multiple teeth on the tip of each barb. FIG. 36C illustrates a plurality of ribbons 59*r* having been anchored by fixing speed nuts 667 against the external surface of the abdominal wall 127/fascia, optionally with a minimal amount of fat interposed, to distribute anchoring forces over anchoring frame 600 which is drawn against the internal surface of the abdominal wall.

Figure 36D:
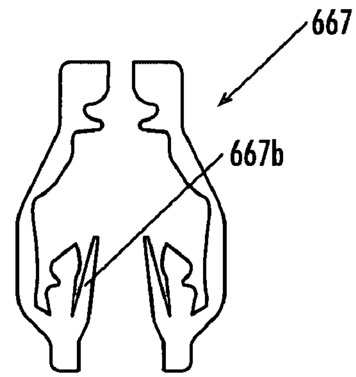
Figure 36H:
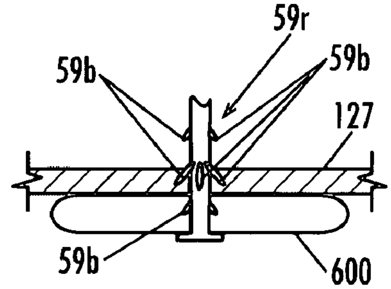
FIG. 36H illustrates a ribbon having barbs, with barbs catching against the abdominal wall/fascia, thereby piercing into the abdominal wall/fascia and flaring out radially somewhat.

FIGS. 36D-36E illustrate another embodiment of a speed nut 667 that is configured to assume undeployed (or extended) and deployed (or compressed) configurations or states. FIG. 36D shown the uncompressed or extended configuration. In this configuration, speed nut 667 can be freely slid over a ribbon 59*r* in both directions. Once speed nut 667 is slid to a desired location with respect to ribbon 59*r*, i.e., to a location where it is desired to lock speed nut 667 with respect to ribbon 59*r*, speed nut 667 is compressed or deployed to assume the compressed or deployed configuration shown in FIG. 36E. This compression can be performed, for example, using graspers or some other endoscopic clamping tool, or a knot pusher tool may be configured to perform the compression function. In the compressed configuration, barbs 667*b* are driven radially inwards, thereby piercing into the ribbon 59*r* to lock the position of speed nut 667 relative to ribbon 59*r*. At the same time, flanges 667*f* extend radially outwardly, thereby increasing the surface area against which the anchoring force is distributed, and functioning like a washer to reduce the risk of pull through of the speed nut through the abdominal wall. Additionally, locking features 667*l* engage one another, thereby locking speed nut 667 in the compressed/deployed configuration. FIGS. 36F-36G show side and perspective views of another embodiment of speed nut 667 having multiple barbs 667*b*. The distal end portion 667*d* has an enlarged face/surface area than the proximal end portion 667*p* to help distribute the anchoring forces. Design of any of these speed nuts attempts to keep the speed nut 667 to a minimum size to facilitate it's passage through the needle puncture in the skin, and facilitating passage through the fat layer, while making at least the distal end surface sufficiently large so that the speed nut 667 will not pull through the fascia or abdominal wall at the location where it is being anchored. In embodiments where the speed nut 667 is metal, there may not be a locking feature, as plastic deformation of the metal may be utilized instead to transform and hold the speed nut when driven from an undeployed to a deployed state. Further alternatively, speed nut 667, whether made of metal or polymer or some combination, may be provided with flange elements that extend substantially parallel to the ribbon when in an undeployed state, and, once the speed nut is located where it is to lock the ribbon in position relative to the fascia, the flanges can be folded proximally to provide a larger surface area to prevent movement of speed nut 667 through the fascia. Flanges may be bent until they collide with features on the speed nut that prevent further rotation thereof. This embodiment does not require locking mechanisms or plastic deformation to hold the flanges in their deployed configuration.

Figure 37A:
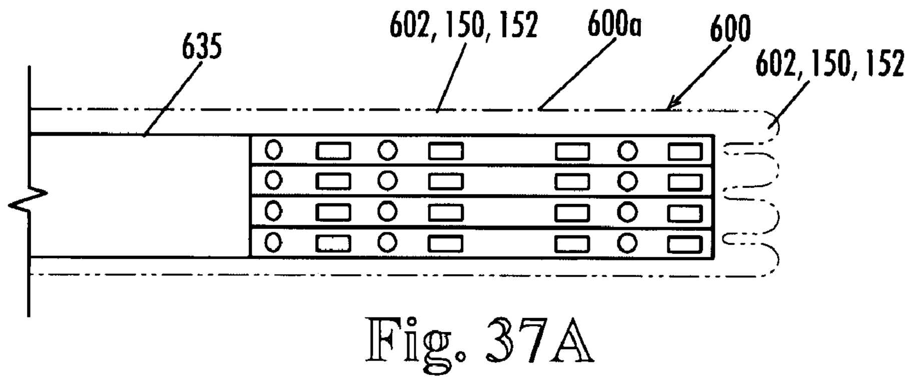
FIGS. 37A-37B illustrate an expandable anchoring frame.
Figure 37B:
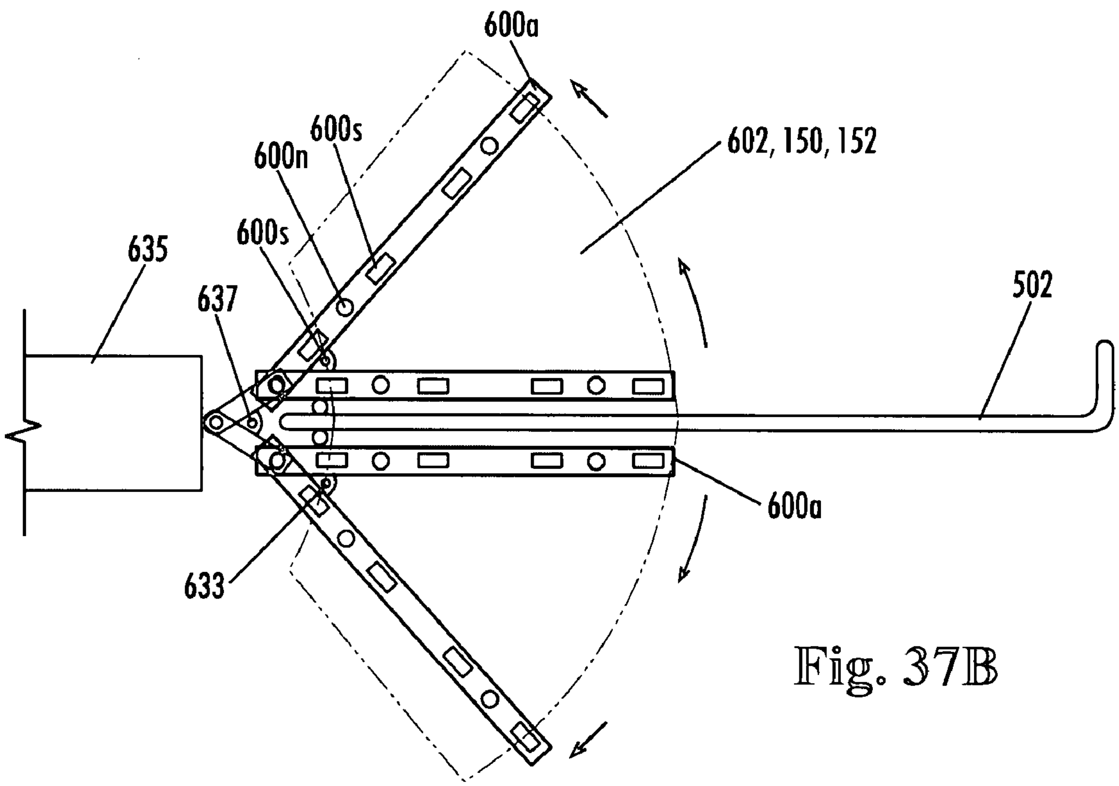

In order to provide a wider anchoring frame 600 platform that is not limited by the diameter of the opening through the patient through which the anchoring frame is delivered, anchoring frame 600 may be configured to be expandable, as illustrated in FIGS. 37A-37B. As shown, anchoring frame 600 includes four expandable arms or beams 600*a*. However, this embodiment is not limited to four beams 600*a* as two, three, or greater than four beams 600*a* may be employed and configured according to the following description to perform similar functions. FIG. 37A illustrates frame 600 in a collapsed configuration in which arms 600*a* are collapsed together to reduce the cross sectional dimensions thereof to dimensions small enough to be passed through the opening (e.g., 225 or 227) in the patient. Typically, a delivery tool having a tube or cannula 635 is provided through which the collapsed frame 600 can be slidingly passed for delivery of the frame 600 into the abdominal cavity. FIG. 37B shows frame 600 in an expanded configuration after delivery through tube 635 into the abdominal cavity, where arms or beams 600*a* spread apart from one another, or "fan out" to from the broad-based platform of anchoring frame 600. Beams or arms 600*a* may be pivotally 637 connected to one another via pivot joints 636 and may be spring-loaded 633 so as to spread apart (in the directions of the arrows in FIG. 37B) when a constraining force holding the arms or beams in the compact configuration of FIG. 37A is removed. Alternatively, arms 600*a* may be configured to unwind like a clock spring when compression forces of the deployment device are removed from holding the frame in a compact configuration. Further alternatively, arms or beams 600*a* maybe spread apart or radially expanded by plastic deformation to maintain an expanded configuration. For example, once the frame 600 has cleared the delivery tool distal end portion 635, arms or beams 600*a* may spread apart.

Arms or beams 600*a* are attached to a sheet of tissue ingrowth material 602 that folds up, as illustrated (in phantom) in FIG. 37A when beams or arms 600*a* are in the collapsed or contracted configuration, and which are extended into the sheet configuration when arms or beams are extended or fanned out, as illustrated (in phantom) in FIG. 37B. This tissue ingrowth material 602 is anchored between the beams or arms 600*a* and the internal abdominal body structure when anchoring frame is anchored thereto, such as in a manner described above with regard to FIGS. 35C-35H. Thus, needles and sutures are driven through each of the arms or beams 600*a* in a manner like that already described. Alternatively, the tissue ingrowth material may be the tabs 150 and tissue ingrowth patches 152 extending from an expandable member 10*em* of a device 10 as described above. In this alternative arrangement, expandable member 10*em* is inserted together with anchoring frame 600 and anchored directly to the internal abdominal body structure by suturing through the arms or beams 600*a* and the tabs 150/tissue ingrowth pads 152 to fix them directly to the internal abdominal structure.

Figure 37C:
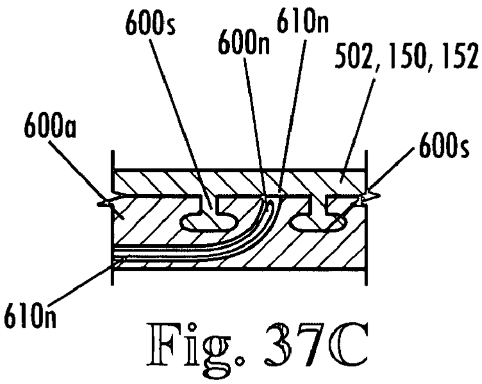
FIGS. 37C and 37D illustrate longitudinal sectional views of a portion of an arm or beam and ingrowth sheet, where
Figure 37D:
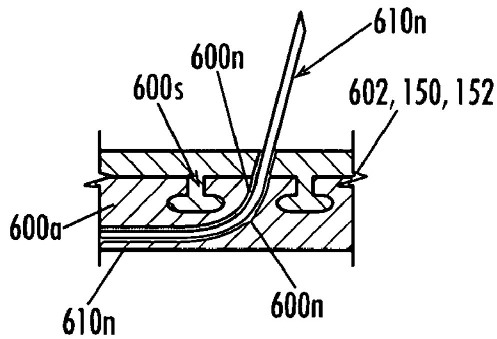

In either case, beams or arms 600*a* are attached to ingrowth material 602,150,152 such as by snaps 600*s*, or alternatively, by sutures, or other mechanical fixation means. Any of these connections may be supplemented using adhesives, or adhesives alone may be used to establish the connections. Although not required, it may be preferable to establish connections 600*s* on both sides of needle openings 600*n* through which the needles 610*n* pass when performing the anchoring steps. This is illustrated in the longitudinal sectional views of a portion of an arm or beam 600*a* and ingrowth sheet 602, 150,152 in FIGS. 37C and 37D, where FIG. 37C shows needle 610*n* in a retracted configuration, and FIG. 37D shows needle 610*n* protruding through arm or beam 600*a* and ingrowth sheet 602,150,152. Anchoring frame 600 may also include a central tube or lumen 600*c* (FIG. 37B) that slides over guidewire 502 to guide delivery of the assembly into the abdominal cavity and along the structure to which frame 600 is to be anchored. Alternatively, instead of a guidewire 502, a scope may be used such that the scope provides visualization and also provides the guiding utility while positioning the frame 600. Scope may also provide a semi-rigid guiding member for the delivery. Alternative to tube 635, tool 630 may be provided with a channel 650 sufficiently wide to receive the arms or beams 600*a* in the collapsed configuration. Upon pushing or otherwise sliding frame 600 out of channel 650, arms or beams 600*a* expand as already described. Expansion of arms or beams 600*a* may be limited by travel limits of the pivot joints 633, or may be limited when ingrowth material sheet 602,150,152 is fully extended, thereby ensuring that the ingrowth material sheet is maintained under tension to ensure it stays fully spread open.

Figure 38A:
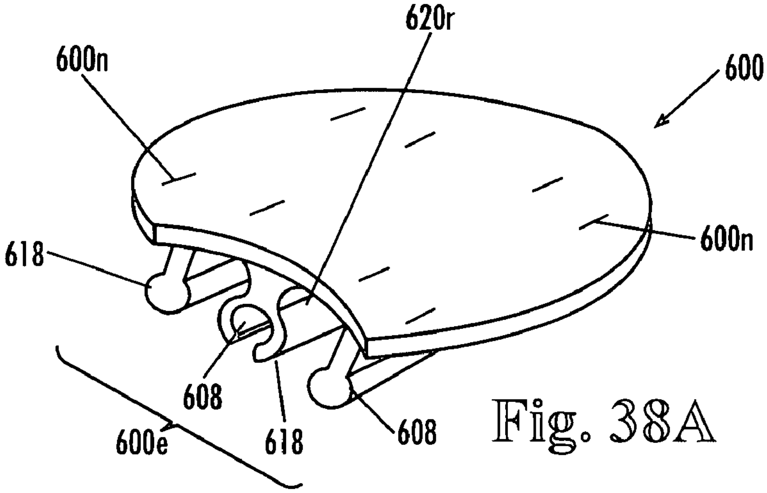
FIGS. 38A-38B illustrate mating engagement members that can be provided as part of any of the frames described herein and any of the expandable members described herein, respectively.
Figure 38B:
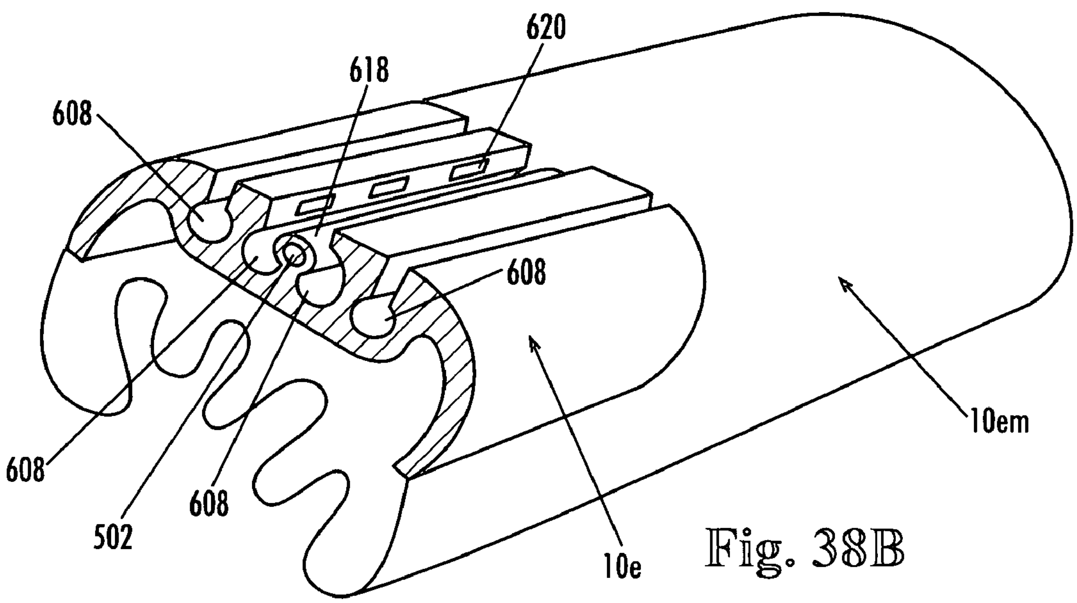

FIGS. 38A-38B illustrate mating engagement members 600*e*, 10*e* that can be provided as part of any of the frames 600 described herein and any of the expandable members 10*em* described herein, respectively, as well as any of the frames and expandable members described in application Ser. No. 11/716,985. Further alternatively, and of the frames 600 and expandable members 10*em* may be provided with any of the interengaging arrangements described in application Ser. No. 11/716,985, e.g. see FIGS. 13A, 13D, 14A-14C, 15A-15C and 19A-19B and the descriptions thereof. Engagement member 600*e* in FIG. 38A provides for multiple track tracking of expandable member 10*em*. Engagement member 600*e* includes a pair of rails 618 on opposite sides of a channel 608 within a rail 618, each of which extend substantially over the length of frame 600 (or a beam or arm 600*a* thereof). FIG. 38B shows engaging member 10*e* fixed to expandable member 10*em* where the engaging member 10*e* includes a pair of channels 608 on opposites sides of a rail 618 that extends from a channel 608, wherein these features are configured to mated with the rails 618 and channel 608 of engagement member 600*e* to be slidably received therein (or thereover, respectively) to interengage the expandable member 10*em* with the anchoring frame 600. Rail 610 of engagement member 10*e* includes a central lumen therethrough, so that it can be passed over guidewire 502 to guide engagement member 10*e* into alignment with engagement member 600*e* to slidingly engage the components together.

Engagement member 10*e* can be provided with locks 620 that automatically lock engagement member 10*e* to engagement member 600*e* thereby securing expandable member 10*em* in a rotationally and translationally stable position relative to frame 600. In the example shown, locks 620 are spring loaded and are substantially flush with the channel 608 at distal ends thereof, but have proximal ends that angle into the channel 608. The proximal ends are depressed to be substantially flush with the channel 608 surface as engagement member 10*e*, and particularly channel 608 is being slid over central rail 618 of engagement member 600*e*, as the proximal ends of the locks 620 are pressed against the rail 618 surface. As the component become fully engaged, they are stopped in the direction of relatively sliding to achieve this engagement by stops provided on engagement member 600*e*. Engagement member is locked and thereby prevented from sliding in the opposite direction when the proximal ends of locks 620 expand into mating recesses 620*r* formed in rail 618. The arrangement of locks 620 and recesses 620*r* can be reversed between the components 10*e* and 600*e*, as would be readily apparent to one of ordinary skill in the mechanical arts. FIG. 38C illustrates expandable member 10*em* in a compacted, low profile configuration for insertion into the abdominal cavity of a patient 1, with the central lumen of rail 618 having been threaded over guidewire 502 for sliding delivery and guidance of the device into the abdominal cavity. However, this is just a mock-up, as guidewire 502 is not shown installed into the abdominal cavity, and that would be performed prior to threading device 10*em* onto the guidewire 502. Alternatively, anchoring frame 600 may having buoyancy features integrated therein, which can be desirable to reduce the incision size made in the patient for insertion of the anchoring frame 600 as well as device 10, since this can reduce the overall volume of the implant 10 by moving some of the volume (e.g., the volume taken up by a buoyancy member 10*bm*) to the anchoring frame 600. Further alternatively, a smaller buoyancy member 10*bm* can be included in device 10, with a buoyancy member provided in or on anchoring frame 600 to provide combined buoyancy effects.

FIGS. 39A-39C illustrate another embodiment of mating engagement members 600*e*, 10*e* that can be provided as part of any of the frames 600 described herein and any of the expandable members 10*em* described herein, respectively, as well as any of the frames and expandable members described in application Ser. No. 11/716,985. In this arrangement, position adjusting features are provided so that the user/surgeon can select amount a range of locations for positioning expandable member 10*em* relative to anchoring frame 600. In FIG. 39A, the engagement member 10*e* comprises a spine or rail 618 that is received in a groove or channel 608 in anchoring member 600. However, these components could be reversed, with anchoring frame 600 having a spine or rail 618 over which a channel or groove, provided in expandable member 10*em*, can be passed.

An adjustable locking mechanism 20 in this embodiment includes detents 622 that are configured and dimensioned to be received in locking holes or openings 624. When detents 622 are positioned through a pair of openings 624, this prevents further relative sliding between rail 618 and channel 608. An actuator 626 may be provided on either the anchoring frame 600/channel 608, whichever includes the engagement member having the detents 622 to, in a first position, temporarily lock the detents in a retracted configuration so that they cannot release and extend through openings 624, and, when slid to a second position, release the detents, which are biased, such as by spring-loading for example, so that they deploy to pass into a pair of openings 624 that they are aligned with. If the openings 624 are not aligned with the detents, the expandable member 10*em* can be slid in one direction or the other, relative to anchoring frame 600 to engage the next adjacent pair of openings 624.

Alternatively, openings 624 may be beveled or tapered to that if detents 624 are only partially inserted into openings 624, as illustrated in FIG. 39C, Then rail can still be slid relative to channel 608, as detents ride in and out of the shallow, beveled portions of openings 624 as rail 618 is slid, since the detents 622 are prevented from passing deeper into holes 24 as long as guidewire or rod 501 is positioned through a lumen 623 provided through rail 618. Once the surgeon/user has positioned expandable member 10*em* is a desired location relative to the anchoring frame, as selected from a multiplicity of possible axial locations along the frame, made possible by the pairs of openings extending longitudinally over rail 618, guidewire or rod 502 is removed from its location with rail 618, allowing detents 622 to slide into locking positions through openings 624. In this arrangement, detents can be unlocked again by reinserting guidewire or rod 502 which pushes the detents back out to the configuration shown in FIG. 39C, allowing expandable member to be repositioned along the length of the engagement mechanism.

FIGS. 40A-40H illustrate various embodiments of buoyancy members 10*bm* that also function as anchoring frames 600. The embodiment of FIG. 40A includes a tubular foam member 10*bmt* which may be formed from silicone foam, or some other polymeric foam, for example. Mesh ribbons 170, which may be in the form of looped ribbons or single lengths of ribbons, may be tied around the tubular member 10*bmt*, or suture thereto, or both, or fixed using alternative mechanical fixation structures and/or adhesive. Ribbons (e.g., polypropylene or other polymer) 170 can be pulled through openings extending from the abdominal cavity of the patient, out through the skin of the patient, to draw buoyancy member/anchoring frame 10*bm*,600 against the internal surface of the abdominal wall, and ribbons can be anchored externally of the abdominal wall 127 in any of the manners already discussed previously above. An expandable member 10*em* of a device can then be passed over tube 10*bmt* and anchored thereto, wherein the buoyancy tube 10*bmt* performs the functions of a buoyancy member discussed above, as well as the functions of an anchoring frame 600 discussed above. Alternatively, expandable member may be anchored to tubular buoyancy member/anchoring frame 10*bm*,600 using a docking tether, as described in more detail below.

Figure 40A:
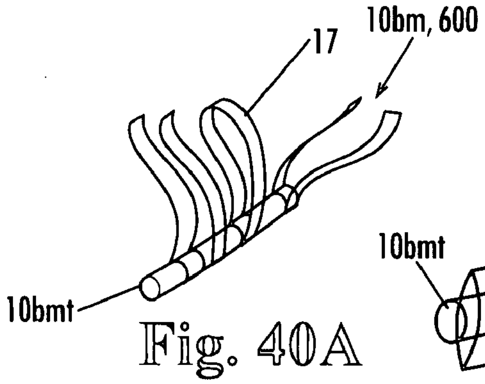
FIGS. 40A-40H illustrate various embodiments of buoyancy members that also function as anchoring frames.
Figure 40B:
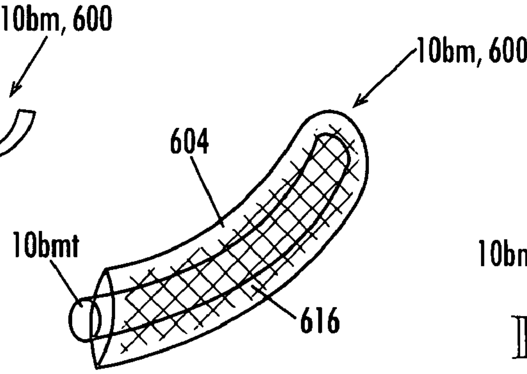
Figure 40C:
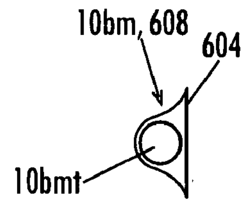
Figure 40D:
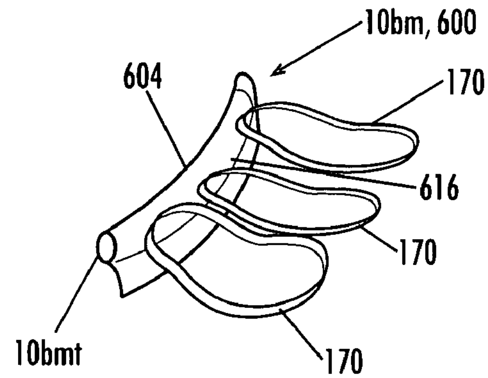

FIG. 40B illustrates an embodiment of buoyancy member/anchoring frame 10*bm*,600 provided with a contact surface 604 having tissue ingrowth-enhancing material 616 provided thereon for enhancing/encouraging tissue ingrowth therein from the internal structure of the abdominal cavity to which contact surface 604 is anchored to (e.g., internal surface of abdominal wall 127). FIG. 40C shows an end view of the buoyancy member/anchoring frame 10*bm*,600 of FIG. 40B. FIG. 40D illustrates ribbon loops 170 attached to tubular member 10*bmt* and extending through backing surface 604 and tissue ingrowth-enhancing material 616 in position to be pulled out of the patient to draw buoyancy member/anchoring frame 10*bm*,600 up against an internal body structure to be anchored there.

Figure 40E:
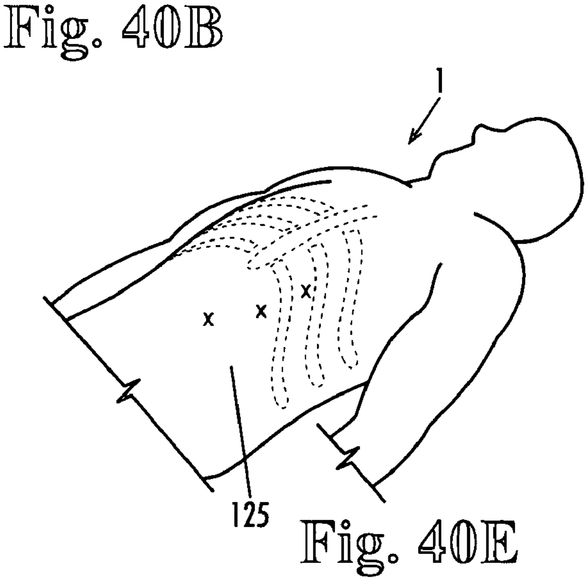

FIG. 40E is an illustration of a patient showing one example of where ribbons 170 can be pulled through the skin 125 of the patient to draw the buoyancy member/anchoring frame 10*bm*,600 up against the inner surface of the abdominal wall. The X's indicate locations where punctures can be made and a hooked tool or graspers can be inserted therethrough to retrieve ribbons 170 to pull them out of the patient 1, draw the buoyancy member/anchoring frame 10*bm*,600 up against the inner surface of the abdominal wall, and lock ribbons 170 down against an external surface of the abdominal wall/fascia. It is noted that optionally, at least one of the ribbons can be drawn though an intercostal space, as shown in FIG. 40E.

Figure 40F:
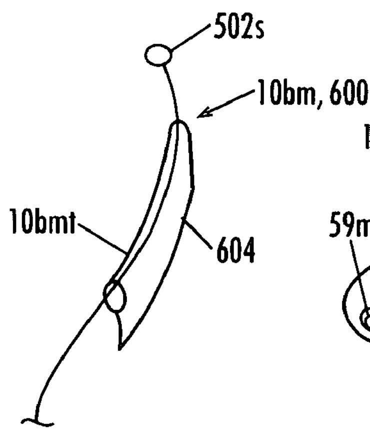
Figure 40G:
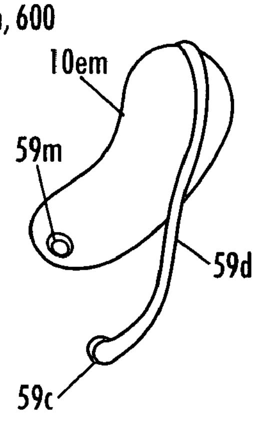

FIGS. 40F-40G illustrate features for anchoring the expandable member 10*em* to the buoyancy member/anchoring frame 10*bm*,600 according to one method embodiment. In this embodiment, buoyancy tube 10*bmt* is provided with an annular opening therethrough. After anchoring the buoyancy member/anchoring frame 10*bm*,600 to an internal abdominal structure, such as the abdominal wall, in a manner as described above, a guidewire 502 or snare catheter 502 can be inserted through the lumen of tube 10*bmt* as shown in FIG.

40F. The expandable member 10*em* of device 10 can be provided with a docking tether 59*d*, such as a braided mesh polymer tether, woven polymer tether or ribbon, for example. Docking tether 59*d* can be fixed to a superior portion of expandable member 10*em* and has a free opposite end having a docking connector 59*c*. An inferior portion of expandable member 10*em* is provided with a mating connector 59*m* that is mateable with docking connector 59*c* to form a locked connection. In the example shown, docking connector 59*c* comprises a male luer connector and mating connector 59*m* comprises a female luer connector. However, these could be reversed. Further alternatively, other types of mating, mechanically connectable members could be substituted.

Figure 40H:
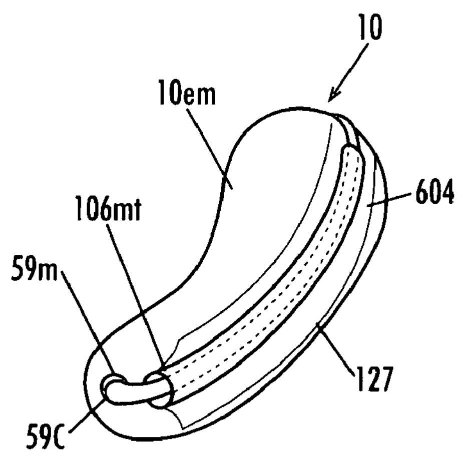

After placing expandable member 10*em* into the abdominal cavity (in a non-expanded configuration), guidewire 502 or snare catheter 502*s* is used to capture the free, proximal end of docking tether 59*d*. The captured free end is then into the distal end opening of tubular member 10*bmt*, through the annular space in tube 10*bmt* and out of the proximal opening. Connector 59*c* is then connected to mating connector 59*m*, thereby locking the free end of docking tether 59*d* to expandable member 10*em* and anchoring expandable member 10*em* to buoyancy member/anchoring frame 10*bm*,600 as illustrated in FIG. 40H.

On advantage of using a dual-function buoyancy member/anchoring frame 10*bm*,600 is that it is a low profile system, since the buoyancy member 10*bm* and expandable member 10*em* do not require simultaneous insertion into the abdominal cavity. Further, a dual-function buoyancy member/anchoring frame 10*bm*,600 is very lightweight and therefore may reduce potential complications during the tissue ingrowth period required for tissue for tissue from the anchored-to structure to grow into the anchoring frame. This can be particularly advantageous in situations where buoyancy member/anchoring frame 10*bm*,600 is anchored by itself and allowed a tissue ingrowth period before fixing an expandable member thereto, or in situations where the expandable member 10*em* is initially fixed to buoyancy member/anchoring frame 10*bm*,600, but is not inflated or only partially inflated with liquid during the tissue ingrowth period.

Figure 41:
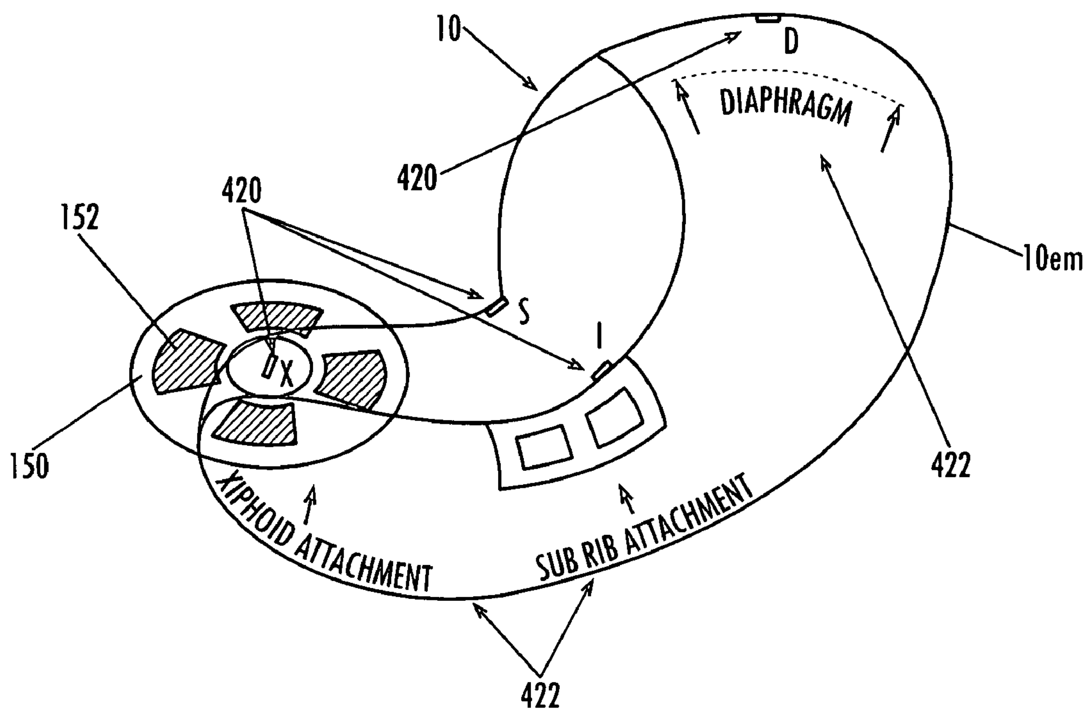
FIG. 41 shows examples of implant markers and sensors that may be included on a device.

FIG. 41 shows examples of implant markers and sensors that may be included on device 10. Any combination of implant markers and sensors shown, including a single marker or sensor, up to and including all markers and sensors shown, may be included on any of the devices described herein, in the locations shown (or corresponding locations for different embodiments of devices 10). Additionally, these features are not limited to the locations shown, but can be included at other locations, such as, but not limited to: anywhere along one or more conduits 12, attachment tab(s) 150, positioning loop(s) 170, any locations on anchoring frame 600 or corresponding components thereof, etc.

Markers 420 may be provided at various locations on device 10 that are trans-abdominally detectable, for example, using fluoroscopy (radiopaque markers), ultrasound (ultrasonically detectable markers), three-dimensional navigation (magnetic or RF sensors) for indirect visualization/tracking of device 10 during the implantation procedure, as well as after device 10 has been implanted and the procedure has been completed. These markers can be present on the surface of device 10 or may be embedded beneath one or more layers of material, or molded within a layer, for example. Additionally, or alternatively, visual indicators 422, such as text, arrows or other graphical markings or visually detectable indicators can be provided for direct viewing by laparoscopy, for example. Indicators 422 may also be provided with contrasting colors to make them easier to locate relative to the portion of device 10 that they are located on.

The material(s) making up all or a portion of device 10 may be doped with radiopaque material to facilitate identification thereof by indirect viewing such as fluoroscopy or other X-ray. Markers 420 and/or indicators 422 may also be used to assess function. For example, the markers 420 identified by "S" and "I" in FIG. 41 may be viewed and a distance therebetween measured to assess the amount of expansion/filling of expandable member 10*em* that has occurred. Markers 420 can additionally or alternatively be used as sensors to provide feedback to measure relative position of device 10, pressure within expandable member 10*em*, motility of device 10, volume occupied by device 10 or expandable member 10*em*, etc. Markers 420 may be detectable trans-abdominally using known sensing modalities such as magnetic, RF, X-ray, ultrasound or auditory signals. Markers 420 may also be configured to emit/transmit RF, ultrasound or auditory signals, for example. Thus, marker(s) 420 and/or indicator(s) 422 can be used to give the surgeon or other person feedback during, as well as after completion of the implantation procedure, as to location of device 10 and/or functionality thereof.

As one example of use of markers 420 for three-dimensional navigation of the delivery and placement of device 10 during an implantation procedure, a pre-existing "map" of the internal structures of a patient 1 may be provided in the way of a CT scan, for example, so that a surgeon can study this map prior to the procedure and identify the bony structures around the abdominal cavity, to be used as landmarks during the procedure to help in navigating/directing device 10 and associated tools to one or more desired target locations in the surgical site. Although soft tissues will be mobile, the surgeon can identify target locations relative to the bony landmarks.

At the beginning of the procedure, typically, prior to making an incision, the actual bony structures of the patient 1 (as visualized under fluoroscopy, for example, or palpation to identify pre-determined registration points) are registered to match the locations of the same structures on the pre-existing map, which can be displayed on a monitor, for example. During the procedure, the markers 420, whether detected by fluoroscopy, magnetic detection, RF detection, ultrasound detection, etc. are displayed on the monitor overlaid on the pre-existing map to which the bony structures of the patient 1 have been registered. Accordingly, the surgeon/user can view in real time, a three dimensional image of the location of markers 420 relative to the landmark bony structures, to guide the surgeon/user to deliver device 10 along a desired pathway and place and implant device 10 in the desired target location.

Not only can device 10 be navigated in this manner, but any other instruments or devices inserted into the patient 1 during the procedure, can also be navigated in similar fashion. For example, insertion and placement of guidewire 502, prior to insertion of device, can be guided and navigated by provided a distal tip or distal end portion of guidewire with a sensor 420. Other tools and devices can be navigated similarly.

Sensors 420 may be passive and/or active. For example, sensors 420 can simply be magnets or radiopaque markings, which are passive sensors that are detected by instrumentation outside of the body of the patient. Alternatively, sensors 420 may be active, such as sensors that transmit RF signals, or other electrical signals, for example. Further alternatively, sensors 420 may have both passive and active functions. A sensor may be "pinged" by instrumentation outside of the patient's body and reflected waves returned from the senor being pinged can be triangulated by feedback from external sensors to determine the location of sensor 420. Sensor 420 may include an antenna and processor that can instruct it to emit a signal when a particular instruction has been received by the antenna. Any of the sensing and/or navigation methods described above can optionally also reference the stomach 120, such as by fluoroscopy or X-ray when radiopaque contrast fluid is inputted into the stomach.

Figure 42:
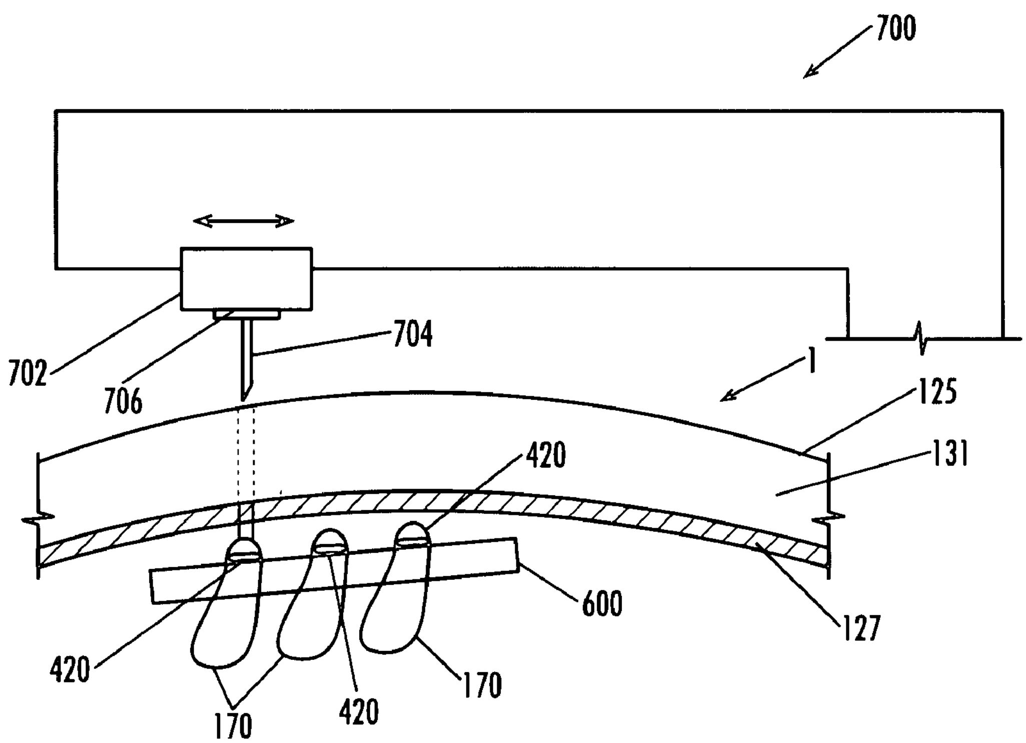
FIG. 42 illustrates a procedural step for anchoring an anchoring frame to an internal surface of an abdominal wall using ribbons.

One or more sensors 420 may also be used for the performance of one or more procedural steps robotically. As one non-limiting example of this, FIG. 42 illustrates a procedural step for anchoring frame 600 to an internal surface of abdominal wall 127 using ribbons 170. A robotic arm 700 having a controllable module 702 that is controllable to move a working tool 704 (in this case, a hooked needle) in three dimensions is provided over that patient 1. Module 702 is first moved in two dimensions parallel to the skin of the patient (i.e., in the dimensions of the arrows shown and the dimension into and out of the page) to align sensor 706 with a sensor 420 on anchoring frame 600 that is aligned with one of the ribbons 170. Once this alignment has been confirmed, tool 704 is then robotically driven into the patient 1 to pierce the skin 125 and to a depth to engage loop 170 with the hooked portion of the needle 704. Tool 704 is then retracted back out of the patient to pull a portion of the ribbon 170 out of the skin 125. Tensioning of the ribbon 170 and anchoring it to an external surface of the abdominal wall/fascia 127 can optionally also be performed robotically. It is noted that this is only an example of a robotic procedural step that can be performed, as virtually any and all procedural steps described herein can be performed robotically, using the sensing and control techniques described herein.

Figure 43:
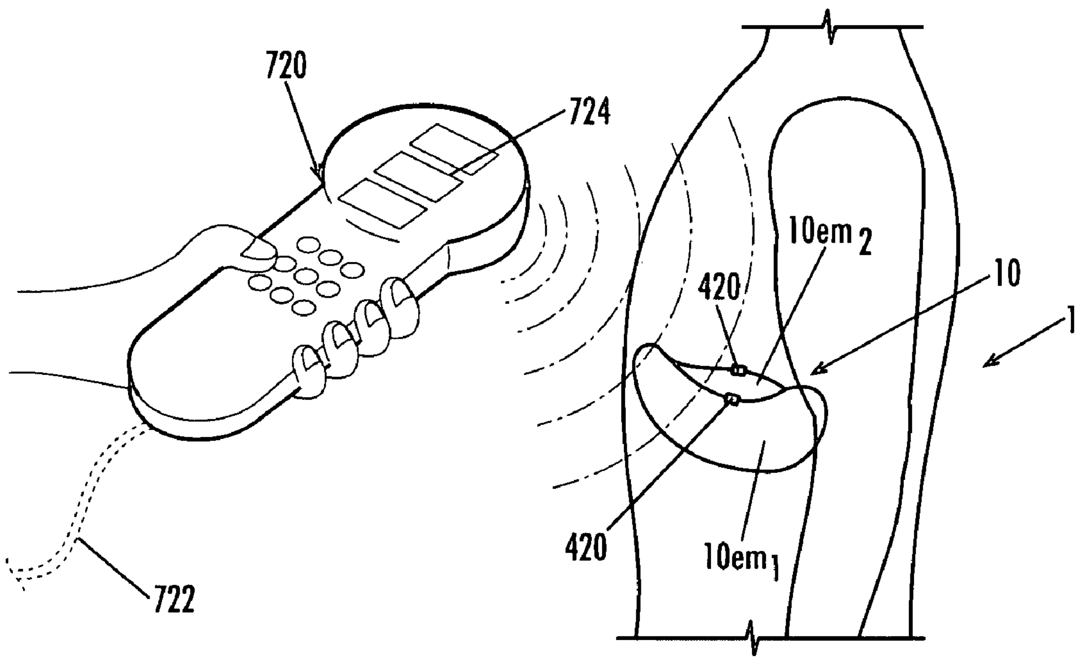
FIG. 43 illustrates a handheld device configured to communicate with one or more sensors located internally of a patient.

FIG. 43 illustrates a handheld device 720 configured to communicate with one or more sensors 420 located internally of the patient, such as on device 10 (and/or anchoring frame 600, conduit 12, etc.) Handheld device may be powered by a power cord 722 that plugs into an electrical outlet, or may be battery powered, and thus more portable. Device 720 may be operated by a treating physician, or by the patient himself, for example. In the example shown, device 10 includes two expandable members 10$em_1$ and 10$em_2$, each provided with a pressure sensor 420 configured to receive a wirelessly transmitted signal from handheld device 720, and, in response thereto, transmit a wireless signal (e.g., RF signal or the like) to handheld device to indicate the current pressure reading. Other sensing capabilities that may be provided include, but are not limited to: sensing of stomach motility via electrical signals or motion sensors or stretch detectors; pressure sensing; temperature sensing; oxygenation sensing; sensing of grehlin or other hunger or satiety markers. Upon reading the signals from sensors 420, device 720 displays the sensed pressures on display 724, for example. These readings can provide useful information to the patient 1 and /or physician as to whether an expandable member(s) has sufficient pressure or is over or under inflated, for example and thus whether a pressure adjustment needs to be made. Additionally, these readings can identify a leak in the device and alert the user thereto, without the need for initial checking by X-ray or more invasive means. Device 720 may also be connectable to the Internet, for example, by wireless communication, and may be programmed to email a physician when used by the patient 1 and when one or more readings is not within expected ranges, thereby alerting the physician that the patient needs to be seen in the physician's office to correct a problem with the device 10.

Figure 44:
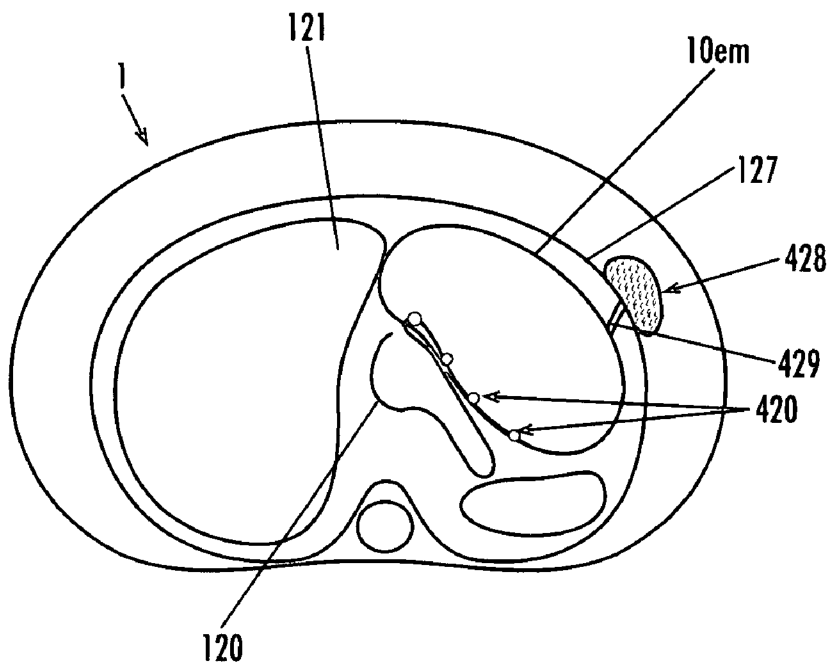
FIG. 44 illustrates an example where a surface of an expandable member is provided with sensors comprising electrodes that can be used to deliver pacing signals to the stomach.

FIG. 44 illustrates an example where a surface of expandable member 10*em* is provided with sensors 420 comprising electrodes that can be used to deliver pacing signals to the stomach from a subcutaneously placed pacer/stimulator 428 that communicates via wires 429 or wirelessly with electrodes of sensors 422. Sensors 422 may also function as pressure sensors and send signals representative of pressure readings to pacer/stimulator 428. Accordingly, when signals are received that correspond to pressures greater than a predetermined pressure level (e.g., indicative of food having been inputted to the stomach 120) this can initiate a pacing program in the pacer/stimulator to send coordinated stimulation signals to the electrodes 420 to increase or decrease motility caused by contraction of stomach muscles resulting from the pacing signals applied by the electrodes 420.

Figure 45:
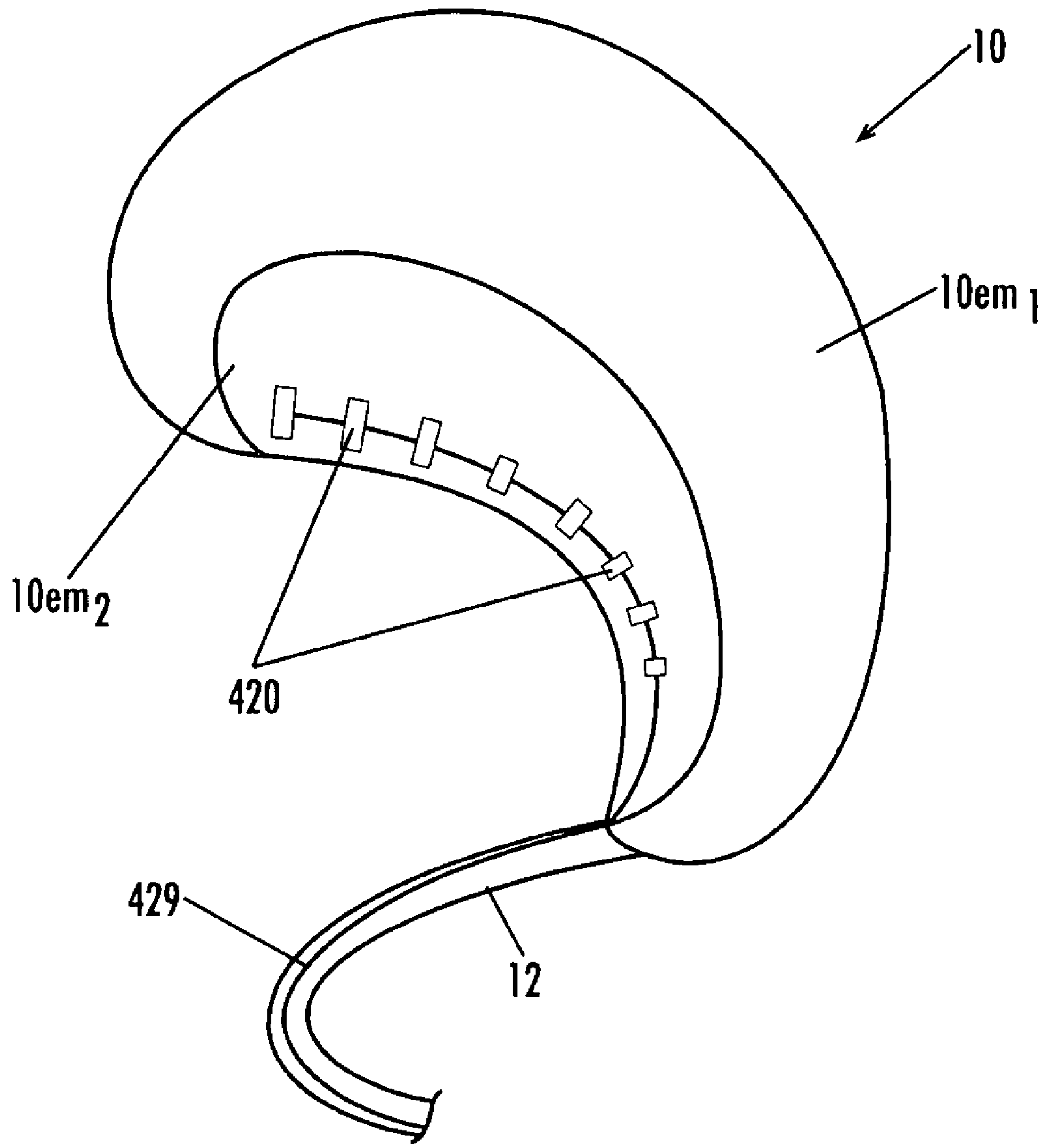
FIG. 45 illustrates another embodiment of a device 10 configured to pace the stomach.

FIG. 45 illustrates another embodiment of device 10 in which wiring 429 extends through conduit 12 to be connected to pacer/stimulator 428. In this case, pacer/stimulator 428 may be incorporated into access member 80 or subcutaneously implanted adjacent access member 80, for example. Although device 10 is shown to include two expandable members 10$em_1$, 10$em_2$, this arrangement may be applied equally as well to devices having a single expandable member 10*em* (with or without buoyancy member 10*bm*) or more than two expandable members. Further alternatively, sensors 420 in either FIG. 44 or FIG. 45 may not provide pressure sensing feedback, but may be only electrodes for applying the pacing signals. In such case, pacer/stimulator 428 may be controlled manually by the user or physician, either wirelessly, or by plugging a controller into a socket provided in access member 80, or on the skin 125 of the patient, for example, to apply pacing signals to the electrodes 420.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating a patient, said method comprising the steps of:

passing a device including an expandable member in a collapsed configuration and a buoyancy member into the abdominal cavity of the patient, outside of the stomach; and anchoring at least a portion of the expandable member, relative to at least one structure in the abdominal cavity;

wherein said expandable member has a first buoyancy characteristic in the abdominal cavity and said buoyancy member has a second buoyancy characteristic in the abdominal cavity, and wherein said second buoyancy characteristic is different from said first buoyancy characteristic.

2. The method of claim 1, further comprising expanding the expandable member to an expanded configuration in a space in the abdominal cavity to perform at least one of: prevention of expansion of the stomach of the patient into the space; and compression of a portion of the stomach.

3. The method of claim 1, wherein the buoyancy member and the expandable member are passed into the abdominal cavity together, in the same method step.

4. The method of claim 1, wherein the buoyancy member and the expandable member are passed into the abdominal cavity in separate passing steps.

5. The method of claim 1, wherein the steps are performed without direct visualization thereof.

6. The method of claim 1, wherein at least one of the steps is performed under direct visualization.

7. The method of claim 2, wherein the expandable member is expanded by inputting liquid therein, and wherein the second buoyancy characteristic of said buoyancy member has a degree of positive buoyancy, relative to the density of the surroundings of the device in the abdominal cavity, to offset the first buoyancy characteristic which is a negative buoyancy of the expandable member containing the liquid, to provide a combined buoyancy of the device so that the device is substantially neutrally buoyant relative to the surroundings.

8. The method of claim 1, wherein the buoyancy member is expandable, said method further comprising inputting gas into the buoyancy member to expand the buoyancy member.

9. The method of claim 8, further comprising adjusting buoyancy of the device by adjusting a degree of expansion of the buoyancy member by performing at least one of: inputting additional gas into the buoyancy member, or removing gas from the buoyancy member.

10. The method of claim 1, wherein the buoyancy member is provided in the shape of an elongated spine.

11. The method of claim 10, wherein the buoyancy member is fixed to an inner surface of the expandable member and rigidifies the expandable member against kinking.

12. The method of claim 1 comprising flattening or otherwise compressing the buoyancy member to a compressed configuration and maintaining the compressed configuration during said passing.

13. The method of claim 12, further comprising removing flattening or compression force from the buoyancy member once the buoyancy member has been placed in the abdominal cavity, wherein, upon removal of said flattening or compression force, the buoyancy member self-expands to a non-compressed configuration.

14. The method of claim 1, wherein said passing comprises passing the expandable member into the abdominal cavity prior to passing the buoyancy member into the abdominal cavity, and wherein the buoyancy member is passed into a chamber within the expandable member when passed into the abdominal cavity.

15. The method of claim 1, wherein said anchoring comprises anchoring at least one attachment tab, extending from the expandable member, to the at least one structure.

16. The method of claim 15, wherein said anchoring comprises anchoring at least one of said attachment tabs to an internal surface of the abdominal cavity.

17. The method of claim 16, wherein said anchoring comprises passing at least one suture through said at least one attachment tab and through the abdominal wall, and fixing said at least one suture externally of an external surface of the abdominal wall.

18. The method of claim 17, wherein said anchoring comprises puncturing through a location of the skin above a location of at least one said suture and inserting an instrument into the abdominal cavity; capturing the suture; and wherein said passing at least one suture through the abdominal wall comprises pulling a portion of the at least one suture through the abdominal wall; applying tension to the at least one suture to draw the at least one attachment tab against an internal surface of the abdominal wall; and fixing the at least one suture externally of the abdominal wall.

19. The method of claim 16, wherein said anchoring comprises passing at least one ribbon, attached to said at least one attachment tab, through the abdominal wall, and fixing said at least ribbon externally of an external surface of the abdominal wall.

20. The method of claim 16, wherein said anchoring comprises passing at least one Q-ring through said at least one attachment tab and through the abdominal wall, thereby fixing said at least one attachment tab to the abdominal wall.

21. The method of claim 15, wherein said anchoring comprises passing at least one Q-ring through said at least one attachment tab and through the at least one structure, thereby fixing said at least one attachment tab to the at least one structure.

22. The method of claim 1, further comprising repositioning the device in the abdominal cavity prior to said anchoring, wherein said repositioning comprises manipulating a positioning loop from outside the patient, the positioning loop being attached to the device.

23. The method of claim 1, further comprising repositioning the device in the abdominal cavity prior to said anchoring, wherein said repositioning comprises puncturing through a location of the skin of the patient and inserting an instrument into the abdominal cavity; capturing a positioning loop attached to the device; pulling a portion of the positioning loop through the abdominal wall; and applying tension to the positioning loop to move the device and draw a portion of the device up against an internal surface of the abdominal wall.

24. The method of claim 23, further comprising fixing a portion of the positioning loop externally of the abdominal wall to prevent it from passing back into the abdominal cavity.

25. A method of treating a patient, said method comprising the steps of:

passing a device into the abdominal cavity of the patient, wherein the device includes at least one attachment member extending from a main body portion thereof;

positioning an inferior portion of the device in the abdominal cavity;

orienting at least one attachment member relative to an inner surface of the abdominal wall; and anchoring the at least one attachment member to the inner surface of the abdominal wall;

wherein said method is performed without piercing the stomach wall;

wherein the device is configured to perform at least one of: prevention of expansion of the stomach of the patient into a space occupied by the device in the abdominal cavity; and compression of a portion of the stomach.

26. The method of claim 25, wherein the device includes an expandable member, the expandable member is in a compressed configuration during said passing of the device, and the method further comprises expanding the expandable member in a space in the abdominal cavity to perform at least one of: prevention of expansion of the stomach of the patient into the space; and compression of a portion of the stomach.

27. The method of claim 26, wherein the device further comprises a buoyancy member to increase an overall buoyancy of the device.

28. The method of claim 25, wherein said orienting comprises puncturing through a location of the skin of the patient and inserting an instrument into the abdominal cavity; capturing a positioning loop attached to the device; pulling a portion of the positioning loop through the abdominal wall; and applying tension to the positioning loop to move the device and draw a portion of the device up against an internal surface of the abdominal wall.

29. The method of claim 28, further comprising fixing a portion of the positioning loop externally of the abdominal wall to prevent it from passing back into the abdominal cavity.

30. The method of claim 25, wherein said positioning comprises grasping at least one positioning tab mounted to said device, and performing at least one of pushing, pulling or twisting forces on the at least one positioning tab to position or orient the device.

31. The method of claim 25, wherein said anchoring comprises passing at least one Q-ring through said at least one attachment member and through the abdominal wall, thereby fixing said at least one attachment member to the abdominal wall.

32. The method of claim 25, wherein said anchoring comprises puncturing through a location of the skin above a location of at least one suture, having been preinstalled through said at least one attachment member, and inserting an instrument into the abdominal cavity; capturing the at least one suture; pulling a portion of the at least one suture through the abdominal wall; applying tension to the at least one suture to draw the at least one attachment member against an internal surface of the abdominal wall; and fixing the at least one suture externally of the abdominal wall.

33. The method of claim 25, wherein said anchoring comprises puncturing through a location of the skin above a location of at least one ribbon attached to said at least one attachment member, and inserting an instrument into the abdominal cavity; capturing the at least one ribbon; pulling a portion of the at least one ribbon through the abdominal wall; applying tension to the at least one ribbon to draw the at least one attachment member against an internal surface of the abdominal wall; and fixing the at least one ribbon externally of the abdominal wall.

* * * * *